United States Patent
Crea et al.

(10) Patent No.: US 12,331,103 B2
(45) Date of Patent: Jun. 17, 2025

(54) FIBRONECTIN BINDING DOMAIN CHIMERIC ANTIGEN RECEPTORS AND METHODS OF USE THEREOF

(71) Applicant: PROTELICA, INC., Burlingame, CA (US)

(72) Inventors: Roberto Crea, Burlingame, CA (US); Jun Yoon, Burlingame, CA (US); Craig A. Hokanson, Pleasanton, CA (US); Emanuela Zacco, Burlingame, CA (US)

(73) Assignee: PROTELICA, INC., Burlingame, CA (US)

( * ) Notice: Subject to any disclaimer, the term of this patent is extended or adjusted under 35 U.S.C. 154(b) by 244 days.

(21) Appl. No.: 16/623,225

(22) PCT Filed: Jun. 15, 2018

(86) PCT No.: PCT/US2018/037945
§ 371 (c)(1),
(2) Date: Dec. 16, 2019

(87) PCT Pub. No.: WO2018/232372
PCT Pub. Date: Dec. 20, 2018

(65) Prior Publication Data
US 2022/0002384 A1    Jan. 6, 2022

Related U.S. Application Data

(60) Provisional application No. 62/521,095, filed on Jun. 16, 2017.

(51) Int. Cl.
*C07K 14/78* (2006.01)
*A61K 38/00* (2006.01)
*A61K 40/31* (2025.01)
*C07K 14/705* (2006.01)

(52) U.S. Cl.
CPC ........... *C07K 14/78* (2013.01); *A61K 40/31* (2025.01); *C07K 14/70517* (2013.01); *C07K 14/70521* (2013.01); *C07K 14/70578* (2013.01); *A61K 38/00* (2013.01); *C07K 2317/31* (2013.01); *C07K 2319/02* (2013.01); *C07K 2319/03* (2013.01); *C07K 2319/21* (2013.01); *C07K 2319/30* (2013.01); *C07K 2319/33* (2013.01); *C07K 2319/70* (2013.01)

(58) Field of Classification Search
CPC ........... C07K 14/78; C07K 14/70517; C07K 14/70521; C07K 14/70578; C07K 2317/31; C07K 2319/02; C07K 2319/03; C07K 2319/21; C07K 2319/30; C07K 2319/33; C07K 2319/70; A61K 38/00
See application file for complete search history.

(56) References Cited

U.S. PATENT DOCUMENTS

| | | | |
|---|---|---|---|
| 4,797,368 A | 1/1989 | Carter et al. | |
| 5,139,941 A | 8/1992 | Muzyczka et al. | |
| 5,858,358 A | 1/1999 | June et al. | |
| 5,883,223 A | 3/1999 | Gray | |
| 5,994,136 A | 11/1999 | Naldini et al. | |
| 6,013,516 A | 1/2000 | Verma et al. | |
| 6,352,694 B1 | 3/2002 | June et al. | |
| 6,354,055 B1 | 3/2002 | Shaw et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 8,680,019 B2 | 3/2014 | Cappuccilli et al. | |
| 2004/0131637 A1 | 7/2004 | Chatfield | |
| 2006/0121005 A1 | 6/2006 | Berenson et al. | |
| 2011/0021746 A1 | 1/2011 | Cappuccilli et al. | |
| 2014/0135474 A1* | 5/2014 | Cappuccilli | C12N 15/1044 530/324 |

(Continued)

FOREIGN PATENT DOCUMENTS

| | | |
|---|---|---|
| WO | WO 1993003769 A1 | 3/1993 |
| WO | WO 1993009239 A1 | 5/1993 |

(Continued)

OTHER PUBLICATIONS

Koide et al., J. Mol. Biol. 284:1141-1151 (1998) (Year: 1998).*

(Continued)

*Primary Examiner* — Thea D'Ambrosio
(74) *Attorney, Agent, or Firm* — LATHROP GPM LLP; Michael Spellberg

(57) ABSTRACT

Provided herein are chimeric antigen receptors (CARs) for binding with a target antigen, comprising at least one antigen specific targeting region comprising a fibronectin type 3 (FN3) domain polypeptide. Provided herein are multispecific chimeric antigen receptors for binding with two or more target antigens, comprising at least two antigen specific targeting regions comprising a fibronectin type 3 domain polypeptide. Also provided herein are compositions and methods of treatment relating to the use of subject CARs of the invention.

5 Claims, 12 Drawing Sheets

Specification includes a Sequence Listing.

(56) References Cited

U.S. PATENT DOCUMENTS

| | | | |
|---|---|---|---|
| 2016/0046729 A1* | 2/2016 | Schönfeld | C07K 14/70517 435/375 |
| 2017/0037131 A1 | 2/2017 | Bernett et al. | |

FOREIGN PATENT DOCUMENTS

| | | |
|---|---|---|
| WO | WO 1993019191 A1 | 9/1993 |
| WO | WO 1994012649 A3 | 6/1994 |
| WO | WO 1994028938 A1 | 12/1994 |
| WO | WO 1995000655 A1 | 1/1995 |
| WO | WO 1995011984 A2 | 5/1995 |
| WO | WO 1996017951 A3 | 6/1996 |
| WO | WO 2010/060095 A1 | 5/2010 |
| WO | WO 2014/145252 A2 | 9/2014 |
| WO | WO 2015063187 A | 5/2015 |
| WO | WO 2016019300 A1 | 2/2016 |
| WO | WO 2017034615 A1 | 3/2017 |
| WO | WO 2017/075537 A1 | 5/2017 |

OTHER PUBLICATIONS

Abken (2015) "Adoptive therapy with CAR redirected T cells: the challenges in targeting solid tumors." *Immunotherapy*, vol. 7, No. 5, pp. 535-544.

Ali, et al. (1998) "Adeno-associated virus gene transfer to mouse retina." *Human gene therapy*, vol. 9, No. 1, pp. 81-86.

Ali, et al. (1996) "Gene transfer into the mouse retina mediated by an adeno-associated viral vector." *Human molecular genetics*, vol. 5, No. 5, pp. 591-594.

Alpuche-Aranda, et al. (1992) "*Salmonella typhimurium* activates virulence gene transcription within acidified macrophage phagosomes." *Proceedings of the National Academy of Sciences of the United States of America*, vol. 89, No. 21, pp. 10079-10083.

Azhar et al., "Recent advances in the development of novel protein scaffolds based therapeutics", *Int. J. Biol. Macromol.*, vol. 102, pp. 630-641, Apr. 13, 2017.

Bennett, et al. (1997) "Real-time, noninvasive in vivo assessment of adeno-associated virus-mediated retinal transduction." *Investigative ophthalmology & visual science*, vol. 38, No. 13, pp. 2857-2863.

Berger, et al. (2009) "Adoptive transfer of virus-specific and tumor-specific T cell immunity." *Current opinion in immunology*, vol. 21, No. 2, pp. 224-232.

Borrás, et al. (1999) "Adenoviral reporter gene transfer to the human trabecular meshwork does not alter aqueous humor outflow. Relevance for potential gene therapy of glaucoma." *Gene therapy*, vol. 6, No. 4, pp. 515-524.

Caldwell (1987) "Temperature-Induced Protein Conformational Changes in Barley Root Plasma Membrane-Enriched Microsomes: II. Intrinsic Protein Fluorescence." *Plant physiology*, vol. 84, No. 3, pp. 924-929.

Cartellieri, et al. (2010) "Chimeric antigen receptor-engineered T cells for immunotherapy of cancer." *Journal of biomedicine & biotechnology*, vol. 2010, p. 956304.

Chatfield, et al. (1992) "Use of the nirB promoter to direct the stable expression of heterologous antigens in *Salmonella* oral vaccine strains: development of a single-dose oral tetanus vaccine." *Bio/technology (Nature Publishing Company)*, vol. 10, No. 8, pp. 888-892.

Chmielewski, et al. (2015) "TRUCKs: the fourth generation of CARs." *Expert opinion on biological therapy*, vol. 15, No. 8, pp. 1145-1154.

Danthinne, et al. (2000) "Production of first generation adenovirus vectors: a review." *Gene therapy*, vol. 7, No. 20, pp. 1707-1714.

De Boer, et al. (1983) "The tac promoter: a functional hybrid derived from the trp and lac promoters." *Proceedings of the National Academy of Sciences of the United States of America*, vol. 80, No. 1, pp. 21-25.

Di Russo, et al. (2012) "pH-Dependent conformational changes in proteins and their effect on experimental pK(a)s: the case of Nitrophorin 4." *PLoS computational biology*, vol. 8, No. 11, p. e1002761.

Dunstan, et al. (1999) "Use of in vivo-regulated promoters to deliver antigens from attenuated *Salmonella enterica* var. Typhimurium." *Infection and immunity*, vol. 67, No. 10, pp. 5133-5141.

Eckelhart, et al. (2011) "A novel Ncr1-Cre mouse reveals the essential role of STAT5 for NK-cell survival and development." *Blood*, vol. 117, No. 5, pp. 1565-1573.

Emanuel et al., "A fibronectin scaffold approach to bispecific inhibitors of epidermal growth factor receptor and insulin-like growth factor-I receptor", *MAbs*, vol. 3, pp. 38-48, Jan. 1, 2011.

Fesnak, et al. (2016) "Engineered T cells: the promise and challenges of cancer immunotherapy." *Nature reviews. Cancer*, vol. 16, No. 9, pp. 566-581.

Flannery, et al. (1997) "Efficient photoreceptor-targeted gene expression in vivo by recombinant adeno-associated virus." *Proceedings of the National Academy of Sciences of the United States of America*, vol. 94, No. 13, pp. 6916-6921.

Flotte, et al. (1993) "Stable in vivo expression of the cystic fibrosis transmembrane conductance regulator with an adeno-associated virus vector." *Proceedings of the National Academy of Sciences of the United States of America*, vol. 90, No. 22, pp. 10613-10617.

Fuhrmann-Benzakein, et al. (2000) "Inducible and irreversible control of gene expression using a single transgene." *Nucleic Acids Research*, vol. 28, Issue 23, pp. e99.

Gandhi (2002) "Effect of pH and temperature on conformational changes of a humanized monoclonal antibody." *Univeristy of Rhode Island Master's Thesis*. DOI: https://doi.org/10.23860/thesis-gandhi-sejal-2002.

Garland, et al. (1999) "The use of Teflon cell culture bags to expand functionally active CD8+ cytotoxic T lymphocytes." *Journal of immunological methods*, vol. 227, Nos. 1-2 pp. 53-63.

GenBank Accession No. AX798980, "Sequence 72 from Patent WO03054189", NCBI Nucleotide Database, Oct. 8, 2003.

GenBank Accession No. AX798961. "Sequence 53 from Patent WO03054189". NCBI Nucleotide Database, Oct. 8, 2003.

GenBank Accession No. AX798183, "Sequence 59 from Patent WO03054201", NCBI Nucleotide Database, Oct. 8, 2003.

Gillis, et al. (2014) "Contribution of Human FcγRs to Disease with Evidence from Human Polymorphisms and Transgenic Animal Studies." *Frontiers in immunology*, vol. 5, p. 254.

Glaser, et al. (2005) "Novel antibody hinge regions for efficient production of CH2 domain-deleted antibodies." *The Journal of biological chemistry*, vol. 280, No. 50, pp. 41494-41503.

Grada, et al. (2013) "TanCAR: A Novel Bispecific Chimeric Antigen Receptor for Cancer Immunotherapy." *Molecular therapy. Nucleic acids*, vol. 2, No. 7, p. e105.

Grindley, et al. (2006) "Mechanisms of site-specific recombination." *Annual review of biochemistry*, vol. 75, pp. 567-605.

Haanen, et al. (1999) "Selective expansion of cross-reactive CD8(+) memory T cells by viral variants." *The Journal of experimental medicine*, vol. 190, No. 9, pp. 1319-1328.

Han et al., "Adnectin-Based Design of Chimeric Antigen Receptor for T Cell Engineering", *Mol. Ther.*, vol. 25, pp. 2466-2476, Jul. 20, 2017.

Harborne, et al. (1992) "Transcriptional control, translation and function of the products of the five open reading frames of the *Escherichia coli* nir operon." *Molecular microbiology*, vol. 6, No. 19, pp. 2805-2813.

Hermanson, et al. (2015) "Utilizing chimeric antigen receptors to direct natural killer cell activity." *Frontiers in immunology*, vol. 6, p. 195.

Hillen, e al. (1989) In Saenger, W. and Heinemann, U. (eds), Topics in Molecular and Structural Biology, Protein-Nucleic Acid Interaction. Macmillan, London, UK, vol. 10, pp. 143-162.

Huck, et al. (1986) "Sequence of a human immunoglobulin gamma 3 heavy chain constant region gene: comparison with the other human C gamma genes." *Nucleic acids research*, vol. 14, No. 4, pp. 1779-1789.

(56) References Cited

OTHER PUBLICATIONS

Hudecek, et al. (2015) "The nonsignaling extracellular spacer domain of chimeric antigen receptors is decisive for in vivo antitumor activity." *Cancer immunology research*, vol. 3, No. 2, pp. 125-135.

International Search Report and Written Opinion for related PCT Application No. PCT/US2018/037945, mailed Oct. 3, 2018 (15 pages).

Jensen, et al. (2014) "Design and implementation of adoptive therapy with chimeric antigen receptor-modified T cells." *Immunological reviews*, vol. 257, No. 1, pp. 127-144.

Jomary, et al. (1997) "Rescue of photoreceptor function by AAV-mediated gene transfer in a mouse model of inherited retinal degeneration." *Gene therapy*, vol. 4, No. 7, pp. 683-690.

Kunii, et al. (2013) "Enhanced function of redirected human T cells expressing linker for activation of T cells that is resistant to ubiquitylation." *Human gene therapy*, vol. 24, No. 1, pp. 27-37.

Li, et al. (1994) "In vivo transfer of a reporter gene to the retina mediated by an adenoviral vector." *Investigative ophthalmology & visual science*, vol. 35, No. 5, pp. 2543-2549.

Li, et al. (1995) "Phenotype correction in retinal pigment epithelium in murine mucopolysaccharidosis VII by adenovirus-mediated gene transfer." *Proceedings of the National Academy of Sciences of the United States of America*, vol. 92, No. 17, pp. 7700-7704.

Ma, et al. (2016) "Versatile strategy for controlling the specificity and activity of engineered T cells." *Proceedings of the National Academy of Sciences of the United States of America*, vol. 113, No. 4, pp. E450-E458.

Marodon, et al. (2003) "Specific transgene expression in human and mouse CD4+ cells using lentiviral vectors with regulatory sequences from the CD4 gene." *Blood*, vol. 101, No. 9, pp. 3416-3423.

Matz, et al. (1999) "Fluorescent proteins from nonbioluminescent Anthozoa species." *Nature biotechnology*, vol. 17, No. 10, pp. 969-973.

McKelvie, et al. (2004) "Expression of heterologous antigens in *Salmonella typhimurium* vaccine vectors using the in vivo-inducible, SPI-2 promoter, ssaG." *Vaccine*, vol. 22, Nos. 25-26, pp. 3243-3255.

Melton, et al. (1984) "Efficient in vitro synthesis of biologically active RNA and RNA hybridization probes from plasmids containing a bacteriophage SP6 promoter." *Nucleic acids research*, vol. 12, No. 18, pp. 7035-7056.

Mendelson, et al. (1988) "Expression and rescue of a nonselected marker from an integrated AAV vector." *Virology*, vol. 166, No. 1, pp. 154-165.

Miyoshi, et al. (1997) "Stable and efficient gene transfer into the retina using an HIV-based lentiviral vector." *Proceedings of the National Academy of Sciences of the United States of America*, vol. 94, No. 19, pp. 10319-10323.

Park, et al. (2015) "Are all chimeric antigen receptors created equal?" *Journal of clinical oncology: official journal of the American Society of Clinical Oncology*, vol. 33, No. 6, pp. 651-653.

Pulkkinen, et al. (1991) "A *Salmonella typhimurium* virulence protein is similar to a Yersinia enterocolitica invasion protein and a bacteriophage lambda outer membrane protein." *Journal of bacteriology*, vol. 173, No. 1, pp. 86-93.

Rolling, et al. (1999) "Evaluation of adeno-associated virus-mediated gene transfer into the rat retina by clinical fluorescence photography." *Human gene therapy*, vol. 10, No. 4 pp. 641-648.

Rothe, et al. (2015) "A phase 1 study of the bispecific anti-CD30/CD16A antibody construct AFM13 in patients with relapsed or refractory Hodgkin lymphoma." *Blood*, vol. 125, No. 26, pp. 4024-4031.

Sakamoto, et al. (1998) "A vitrectomy improves the transfection efficiency of adenoviral vector-mediated gene transfer to Müller cells." *Gene therapy*, vol. 5, No. 8, pp. 1088-1097.

Salmon, et al. (1993) "Characterization of the human CD4 gene promoter: transcription from the CD4 gene core promoter is tissue-specific and is activated by Ets proteins." *Proceedings of the National Academy of Sciences of the United States of America*, vol. 90, No. 16, pp. 7739-7743.

Samulski, et al. (1989) "Helper-free stocks of recombinant adeno-associated viruses: normal integration does not require viral gene expression." *Journal of virology*, vol. 63, No. 9, pp. 3822-3828.

Scheraga (1992) "Predicting Three-Dimensional Structures of Oligopeptides", in *Reviews in Computational Chemistry*, K. B. Lipkowitz and D. B. Boyd, Editors, vol. 3, pp. 73-142, VCH Publishers, New York.

Shaner, et al. (2005) "A guide to choosing fluorescent proteins." *Nature methods*, vol. 2, No. 12, pp. 905-909.

Shetron-Rama, et al. (2002) "Intracellular induction of Listeria monocytogenes actA expression." *Infection and immunity*, vol. 70, No. 3, pp. 1087-1096.

Takahashi, et al. (1999) "Rescue from photoreceptor degeneration in the rd mouse by human immunodeficiency virus vector-mediated gene transfer." *Journal of virology*, vol. 73, No. 9, pp. 7812-7816.

Tan, et al. (1990) "Influence of the hinge region on complement activation, C1q binding, and segmental flexibility in chimeric human immunoglobulins." *Proceedings of the National Academy of Sciences of the United States of America*, vol. 87, No. 1, pp. 162-166.

Ten Berge, et al. (1998) "Selective expansion of a peripheral blood CD8+ memory T cell subset expressing both granzyme B and L-selectin during primary viral infection in renal allograft recipients." *Transplantation proceedings*, vol. 30, No. 8, pp. 3975-3977.

Töpfer, et al. (2015) "DAP12-based activating chimeric antigen receptor for NK cell tumor immunotherapy." *Journal of immunology (Baltimore, Md.: 1950)*, vol. 194, No. 7, pp. 3201-3212.

Turtle, et al. (2016) "CD19 CAR-T cells of defined CD4+:CD8+ composition in adult B cell ALL patients." *The Journal of clinical investigation*, vol. 126, No. 6, pp. 2123-2138.

Valdivia, et al. (1996) "Bacterial genetics by flow cytometry: rapid isolation of *Salmonella typhimurium* acid-inducible promoters by differential fluorescence induction." *Molecular microbiology*, vol. 22, No. 2, pp. 367-378.

Yan, et al. (2012) "Engineering upper hinge improves stability and effector function of a human IgG1." *The Journal of biological chemistry*, vol. 287, No. 8, pp. 5891-5897.

Zhang, et al. (2012). An NKp30-based chimeric antigen receptor promotes T cell effector functions and antitumor efficacy in vivo. *Journal of immunology (Baltimore, Md.: 1950)*, vol. 189, No. 5, pp. 2290-2299.

Zhao, et al. (2010) "Multiple injections of electroporated autologous T cells expressing a chimeric antigen receptor mediate regression of human disseminated tumor." *Cancer research*, vol. 70, No. 22, pp. 9053-9061.

European Office Action for European Patent Application No. 18818842.9, dated Jan. 22, 2024.

Extended European Search Report for European Patent Application No. 18818842.9, dated May 26, 2021.

Gorackov et al., "FnCARs: A Platform Expanding the Repertoire of Proteins Targetable with Chimeric Antigen Receptors", Molecular Therapy, Nov. 2017, 25(5S1): 272.

Kulemzin et al., "Modular lentiviral vector system for chimeric antigen receptor design optimization", Russian Journal of Bioorganic Chemistry, Apr. 19, 2017, 43(2): 107-114.

Partial European Search Report for European Patent Application No. 18818842.9, dated Feb. 22, 2021.

\* cited by examiner

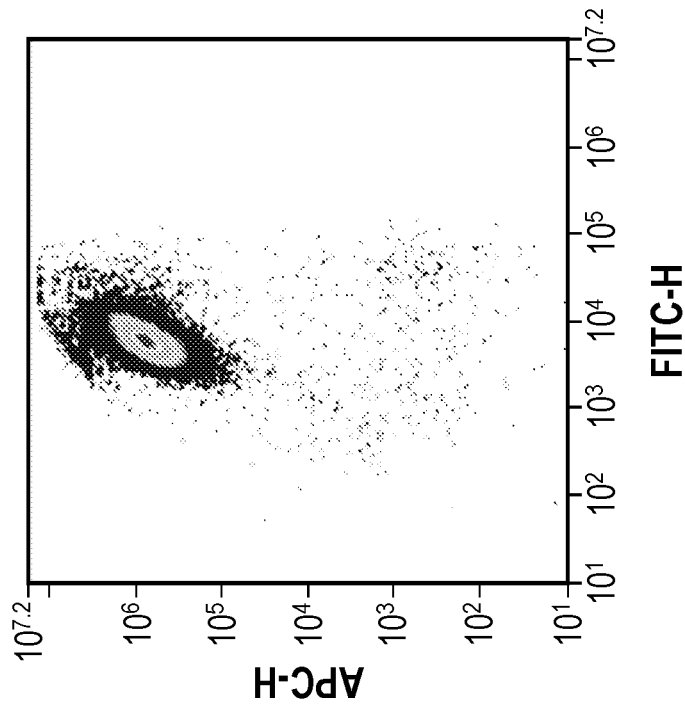
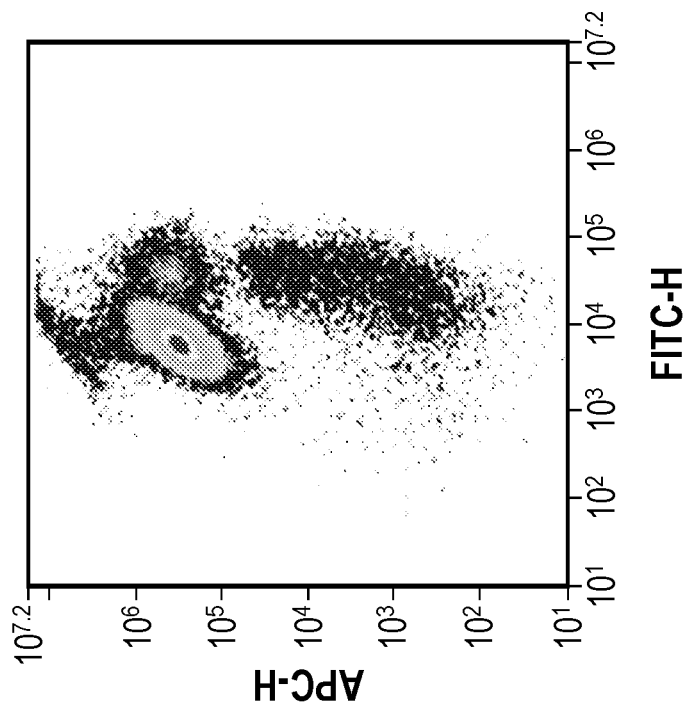
Fig. 5

| FN3 DOMAIN | KD | FN3 DOMAIN | KD | FN3 DOMAIN | KD | FN3 DOMAIN | KD |
|---|---|---|---|---|---|---|---|
| >AXL_R3_2H11 | 12 nM | >D-AXL_R2_L2_B7 | 50 nM | >AXL_R2_1A11 | 33 nM | 43 | 18 nM |
| >AXL_R2_1E5 | 14 nM | >D-AXL_R2_L2_A5 | 28 nM | >AXL_R2_4D2 | 23 nM | 44 | 4 nM |
| >AXL_R2_4A7 | 8 nM | >AXL_R3_2A11 | 29 nM | 33-X | 9 nM | 46 | 6 nM |
| >D-AXL_R2_L3_H8 | 53 nM | >D-AXL_R2_L3_B7 | 532 nM | 34-X | 7 nM | 56 | 12 nM |
| >AXL_R2_L3_G1 | 45 nM | >AXL_R3_2A6 | 79 nM | 35-X | 22 nM | 68 | 5 nM |
| >AXL_R2_4O5 | 8 nM | >D-AXL_R2_L2_C11 | 23 nM | 36-X | 11 nM | 93 | 20 nM |
| >D-AXL_R2_L3_D1 | 62 nM | >AXL_R2_3H1 | 25 nM | 37-X | 13 nM | 113 | 11 nM |
| >AXL_R2_2G2 | 200 nM | >AXL_L3_R2_C8 | 8 nM | 38-X | 28 nM | 126 | 30 nM |
| >AXL_R2_3H7 | 38 nM | >AXL_R2_L1_A6 | 17 nM | 39-X | 101 nM | 133 | 8 nM |
| >AXL_R2_L1_E8 | 20 nM | >AXL_R2_1G5 | 27 nM | 7 | 18 nM | 143 | 45 nM |
| >AXL_R2_4H3 | 33 nM | >D-AXL_R2_L1_F6 | 16 nM | 15 | ND | 155 | 12 nM |
| >AXL_R2_4B6 | 50 nM | >AXL_R2_3A4 | 13 nM | 16 | 92 nM | 175 | 7 nM |
| >D-AXL_R2_L4_B8 | 22 nM | >AXL_R2_3C8 | 24 nM | 28 | 15 nM | 176 | 2 nM |
| >AXL_R2_3G11 | 20 nM | >D-AXL_R2_L3_C1 | 9 nM | 31 | 6 nM | 179 | ND |
| >D-AXL_R2_L2_H4 | 37 nM | >AXL_R2_3A2 | 20 nM | 42 | 20 nM | | |

*Fig. 6*

FIBRONECTIN BINDING DOMAIN CHIMERIC ANTIGEN RECEPTORS AND METHODS OF USE THEREOF

RELATED APPLICATIONS

This application is a 35 U.S.C. § 371 filing of International Patent Application No. PCT/US2018/037945, filed Jun. 15, 2018, which claims priority to U.S. Provisional Patent Application Ser. No. 62/521,095, filed Jun. 16, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 22, 2022, is named 619595_PTI-009US_ST25.txt and is 31,688 bytes in size.

BACKGROUND

Scaffold based binding proteins are legitimate alternatives to antibodies in their ability to bind specific ligand targets. Scaffold based binding proteins include those that are derived from intact human Fibronectin Type III (FN3) domains. The FN3 domain was first identified as one of the repeating domains in the fibronectin protein. The FN3 domain constitutes a small (~94 amino acids), monomeric β-sandwich protein made up of seven β strands with three connecting loops. The three loops near the N-terminus of FN3 are functionally analogous to the complementarity-determining regions of immunoglobulin domains. Scaffold based binding proteins derived from intact human FN3 domains are small ($\frac{1}{15}^{th}$ the size of a conventional monoclonal antibody), have high stability, and have high affinity and selectivity to a target antigen. See, e.g., Cappuccilli et al. (U.S. Pat. No. 8,680,019).

Chimeric antigen receptors (CARs) have been widely investigated for use in treating a variety of cancers. Immunotherapy using cells expressing a CAR (e.g., CAR-T cells) is a very promising therapeutic approach with the potential to eradicate tumor cells. Such therapy may be suitable for any medical condition, although in specific embodiments the cell therapy is for cancer, including cancers involving solid tumors and hematological malignancies. Current CAR molecules are based on the use of scFvs, which are large proteins with immunogenicity issues. In addition, the use of scFvs is associated with aberrant signaling due to instability and flexibility of the scFv structure, the potential for VH/VL domain swapping and multimer formation through framework region interactions, incorrect folding issues, and issues arising from aggregation. As such, current CAR-T strategies suffer from concerns such as significant patient side effects and poor durability of response. For example, the failure of certain clinical trials that use CAR-based immunotherapy has been attributed to scFv immunogenicity, see, e.g., Turtle et al., *J. Clin. Invest.* (2016) 126 (6): 2134-2138.

Accordingly, there remains a need for versatile CAR molecules that have high stability, affinity, and selectivity, and CAR-T cancer therapies that are potent, robust and less toxic, resulting in less patient side effects and higher durability of response.

SUMMARY

In one aspect of the invention, a chimeric antigen receptor (CAR) for binding with a target antigen, comprising: i) at least one antigen specific targeting region comprising a fibronectin type 3 (FN3) domain polypeptide; ii) a transmembrane domain; and iii) an intracellular signaling domain, is provided.

In certain exemplary embodiments, the FN3 domain polypeptide comprises: a) regions A, AB, B, C, CD, D, E, EF, F, and G having wild type amino acid sequences of a selected native fibronectin type 3 polypeptide, and b) loop regions BC, DE, and FG having selected amino acid lengths.

In certain exemplary embodiments, the BC loop length is 11, 14, or 15 amino acids.

In certain exemplary embodiments, the DE loop length is 6 amino acids.

In certain exemplary embodiments, the FG loop length is 8, or 11 amino acids.

In certain exemplary embodiments, the FN3 domain polypeptide comprises the $14^{th}$ fibronectin type 3 module of human fibronectin.

In certain exemplary embodiments, the FN3 domain polypeptide comprises the $10^{th}$ fibronectin type 3 module of human fibronectin.

In certain exemplary embodiments, the CAR further comprises an extracellular spacer domain.

In certain exemplary embodiments, the extracellular spacer domain is selected from the group consisting of an Fc fragment of an antibody, a hinge region of an antibody, a CH2 region of an antibody, a CH3 region of an antibody, an artificial spacer sequence, a hinge comprising an amino acid sequence of CD8, and any combination thereof.

In certain exemplary embodiments, the at least one antigen specific targeting region is evolved from a wild-type antigen specific targeting region and has at least one of: a) a decrease in binding activity to the target antigen in an assay at a normal physiological condition compared to the wild-type antigen specific targeting region; and b) an increase in binding activity to the target antigen in an assay at an aberrant physiological condition compared to the wild-type antigen specific targeting region.

In certain exemplary embodiments, the at least one antigen specific targeting region has a decrease in binding activity to the target antigen in an assay at a normal physiological condition compared to the wild-type antigen specific targeting region.

In certain exemplary embodiments, the at least one antigen specific targeting region has an increase in binding activity to the target antigen in an assay at an aberrant physiological condition compared to the wild-type antigen specific targeting region.

In certain exemplary embodiments, the at least one antigen specific targeting region has both a) a decrease in binding activity to the target antigen in an assay at a normal physiological condition compared to the wild-type antigen specific targeting region, and b) an increase in binding activity to the target antigen in an assay at an aberrant physiological condition compared to the wild-type antigen specific targeting region.

In certain exemplary embodiments, the chimeric antigen receptor has an increase in expression level compared to an identical chimeric antigen receptor comprising the wild-type antigen specific targeting region.

In certain exemplary embodiments, the extracellular spacer domain has an enhanced ubiquitylation-resistance level at an aberrant physiological condition compared to at a normal physiological condition.

In certain exemplary embodiments, the physiological condition is selected from the group consisting of: temperature; pH; osmotic pressure; osmolality; oxidative stress; an electrolyte concentration; a concentration of glucose, lactic acid, pyruvate, nutrient components, metabolites, oxygen, carbonate, phosphate, or carbon dioxide; a cell type; and nutrient availability.

In certain exemplary embodiments, the physiological condition is temperature, and wherein the antigen specific targeting region is substantially inactive at a normal physiological temperature, and is active at an aberrant physiological temperature less than the normal physiological temperature.

In certain exemplary embodiments, the transmembrane domain is selected from the group consisting of an artificial hydrophobic sequence and transmembrane domains of a type I transmembrane protein, an alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, and CD154.

In certain exemplary embodiments, the CAR further comprises at least one co-stimulatory domain.

In certain exemplary embodiments, the at least one co-stimulatory domain is selected from the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3.

In certain exemplary embodiments, the intracellular signaling domain is selected from the group consisting of cytoplasmic signaling domains of a human CD3 zeta chain, FcγRIII, FcεRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

In certain exemplary embodiments, the at least one antigen specific targeting region binds a target antigen selected from the group consisting of AGR2, AIG1, AKAP1, AKAP2, ANGPT1, ANGPT2, ANGPTL3, ANGPTL4, ANPEP, APC, APOC1, AR, AZGP1 (zinc-α-glycoprotein), BAD, BAG1, BAI1, BCL2, BMP6, BPAG1, BRC1A, BRCA1, CANT1, CAV1, CCL11, CCL2, CCNA1, CCNA2, CCND1, CCNE1, CCNE2, CD138, CD164, CD19, CD20, CD22, CD3, CD4, CD44, CD52, CD8, CDH1 (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21$^{Wap1/Cip1}$), CDKN1B (p27$^{Kip1}$), CDKN1C, CDKN2A (p16$^{INK4A}$), CDKN2B, CDKN2C, CDKN3, CEA, CHGA, CHGB, CLDN3, CLDN7 (claudin-7), CLN3, CLU (clusterin), COL18A1, COL1A1, COL4A3, COL6A1, CTNNB1 (β-catenin), CTSB (cathepsin), CXCL1, CXCL10, CXCL3, CXCL5, CXCL6, CXCL9, CYB5, CYC1, DAP2IP, DES, DNCL1, E2F1, ECGF1, EDG1, EFNA1, EFNA3, EFNB2, EGF, EGFR, EGFRvIII, ELAC2, ENG, ENO1, ENO2, ENO3, EPHB4, ERBB2 (Her-2), EREG, ERK8, ESR1, ESR2, F3 (TF), FAP, FASN, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR3, FIGF, FLJ12584, FLJ25530, FLRT1 (fibronectin), FLT1, FOSL1 (FRA-1), GABRP (GABA-A), GAGEB1, GAGEC1, GATA3, GD2, GGT1, GNAS1, GNRH1, GPC3, GRP, GSN (Gelsolin), GSTP1, HGF, HGFR (MET), HIP1, HUMCYT2A, ID2, IFNA1, IFNB1, IFNG, IGF1, IGF1R, IGF2, IGFBP2, IGFBP3, IGFBP6, Igκ light chain, IL12A, IL13RA2, IL1A, IL1B, IL2, IL24, IL29, IL2RA, IL3RA (CD123), IL6, IL6R, IL6ST (glycoprotein 130), IL8, ILK, INHA, INSL3, INSL4, ITGA1, ITGA6 (α6 integrin), ITGAV, ITGB3, ITGB4 (β4 integrin), JAG1, JUN, K6HF, KAII, KDR, KLF5 (GC Box BP), KLK10, KLK12, KLK13, KLK14, KLK15, KLK3, KLK4, KLK5, KLK6, KLK9, KRT1, KRT19, KRT2A, KRTHB6 (hair-specific type II keratin), LAMA5, Lewis-Y, MACMARCKS, MAP2K7 (c-Jun), MDK, MIB1, MKI67 (Ki-67), MMP2, MMP9, MSLN (mesothelin), MSMB, MT3 (metallothionein-3), MTSS1, MUC1 (mucin), MUC16, MYC, NGFB (NGF), NGFR, a NKG2D ligand, NME1 (NM23A), NOX5, NR0B1, NR0B2, NR1D1, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NTN4, ODZ1, P1AS2, P1K3CG, PAP, PART1, PATE, PAWR, PCA3, PCNA, PDGFA, PECAM1, PF4, PGF, PGR, PLAU (UPA), Plectin, PLG, PLXDC1, PPID, PR1, PRKCQ, PRKD1, PRL, PROK2, PSAP, PSCA, PSMA, PTEN, PTGS2 (COX-2), RAC2 (p21-Rac2), RARB, ROBO2, ROR-1, S100A2, SCGB1D2 (lipophilin B), SCGB2A1 (mammaglobin-2), SCGB2A2 (mammaglobin-1), SERPINA3, SERPINB5 (maspin), SERPINE1 (PAI-1), SERPINF1, SHBG, SHBQ, SLC2A2, SLC33A1, SLC43A1, SPRR1B (Spr1), STAB1, STEAP, STEAP2, TEK, TGFA, TGFB1, TGFB1I1, TGFB1I1, TGFB2, TGFB3, TGFBR1, TGRA, THBS1 (thrombospondin-1), THBS2, THBS4, TIE (Tie-1), TIMP3, TNF, TNFAIP2 (B94), TNFRSF6 (Fas), TNFRSF7 (BCMA), TNFRSF8 (CD30), TNFSF10, TNFSF6 (FasL), TOP2A (topoisomerase-2α), TP53, TPM1, TPM2, TRPC6, VEGF, VEGFC, and any combination thereof.

In certain exemplary embodiments, the at least one antigen specific targeting region binds a target antigen selected from the group consisting of CD19, CD20, CD22, Igκ light chain, TNFRSF8 (CD30), CD138, TNFRSF7 (BCMA), CD33, IL3RA (CD123), a NKG2D ligand, ROR1, EGFR, EGFRvIII, GD2, IL13RA2, ERBB2 (Her-2), MSLN (Mesothelin), PSMA, FAP, GPC3, HGFR (MET), MUC16, CEA, Lewis-Y, MUC1, and any combination thereof.

In another aspect of the invention, a multispecific chimeric antigen receptor (CAR) for binding with a target antigen, comprising: i) at least two antigen specific targeting regions, wherein one or more of the antigen specific targeting regions comprises an FN3 domain polypeptide; ii) a transmembrane domain; and iii) an intracellular signaling domain, is provided.

In certain exemplary embodiments, each FN3 domain polypeptide comprises: a) regions A, AB, B, C, CD, D, E, EF, F, and G having wild type amino acid sequences of a selected native fibronectin type 3 polypeptide, and b) loop regions BC, DE, and FG having selected amino acid lengths.

In certain exemplary embodiments, the BC loop length of each FN3 domain polypeptide is 11, 14, or 15 amino acids.

In certain exemplary embodiments, the DE loop length of each FN3 domain polypeptide is 6 amino acids.

In certain exemplary embodiments, the FG loop length of each FN3 domain polypeptide is 8, or 11 amino acids.

In certain exemplary embodiments, the FN3 domain polypeptide comprises the 14$^{th}$ fibronectin type 3 module of human fibronectin.

In certain exemplary embodiments, the FN3 domain polypeptide comprises the 10$^{th}$ fibronectin type 3 module of human fibronectin.

In certain exemplary embodiments, the multispecific CAR further comprises an extracellular spacer domain.

In certain exemplary embodiments, the extracellular spacer domain has an enhanced ubiquitylation-resistance level at an aberrant physiological condition compared to at a normal physiological condition.

In certain exemplary embodiments, the at least two antigen specific targeting regions are connected by a linker.

In certain exemplary embodiments, the linker is a conditional linker having a first conformation at an aberrant physiological condition for the at least two antigen specific targeting regions to bind to the target antigen at a higher binding activity than a binding activity of a second conformation of the conditional linker at a normal physiological condition.

In certain exemplary embodiments, at least one of the at least two antigen specific targeting regions is evolved from a wild-type antigen specific targeting region and has at least one of: a) a decrease in binding activity to the target antigen in an assay at a normal physiological condition compared to the wild-type antigen specific targeting region; and b) an increase in binding activity to the target antigen in an assay at an aberrant physiological condition compared to the wild-type antigen specific targeting region.

In certain exemplary embodiments, at least one of the at least two antigen specific targeting regions has a decrease in binding activity to the target antigen in an assay at a normal physiological condition compared to the wild-type antigen specific targeting region.

In certain exemplary embodiments, at least one of the at least two antigen specific targeting regions has an increase in binding activity to the target antigen in an assay at an aberrant physiological condition compared to the wild-type antigen specific targeting region.

In certain exemplary embodiments, at least one of the at least two antigen specific targeting regions has both a) a decrease in binding activity to the target antigen in an assay at a normal physiological condition compared to the wild-type antigen specific targeting region, and b) an increase in binding activity to the target antigen in an assay at an aberrant physiological condition compared to the wild-type antigen specific targeting region.

In certain exemplary embodiments, the multispecific chimeric antigen receptor has an increase in expression level compared to an identical multispecific chimeric antigen receptor comprising the wild-type antigen specific targeting region.

In certain exemplary embodiments, the physiological condition is selected from the group consisting of: temperature; pH; osmotic pressure; osmolality; oxidative stress; an electrolyte concentration; a concentration of glucose, lactic acid, pyruvate, nutrient components, metabolites, oxygen, carbonate, phosphate, or carbon dioxide; a cell type; and nutrient availability.

In certain exemplary embodiments, the physiological condition is temperature, and wherein the antigen specific targeting region is substantially inactive at a normal physiological temperature, and is active at an aberrant physiological temperature less than the normal physiological temperature.

In certain exemplary embodiments, the intracellular signaling domain is selected from the group consisting of cytoplasmic signaling domains of a human CD3 zeta chain, FcγRIII, FcεRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

In certain exemplary embodiments, the at least one antigen specific targeting region binds a target antigen selected from the group consisting of AGR2, AIG1, AKAP1, AKAP2, ANGPT1, ANGPT2, ANGPTL3, ANGPTL4, ANPEP, APC, APOC1, AR, AZGP1 (zinc-α-glycoprotein), BAD, BAG1, BAI1, BCL2, BMP6, BPAG1, BRC1A, BRCA1, CANT1, CAV1, CCL11, CCL2, CCNA1, CCNA2, CCND1, CCNE1, CCNE2, CD138, CD164, CD19, CD20, CD22, CD3, CD4, CD44, CD52, CD8, CDH1 (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21$^{Wap1/Cip1}$), CDKN1B (p27$^{Kip1}$), CDKN1C, CDKN2A (p16$^{INK4A}$), CDKN2B, CDKN2C, CDKN3, CEA, CHGA, CHGB, CLDN3, CLDN7 (claudin-7), CLN3, CLU (clusterin), COL18A1, COL1A1, COL4A3, COL6A1, CTNNB1 (β-catenin), CTSB (cathepsin), CXCL1, CXCL10, CXCL3, CXCL5, CXCL6, CXCL9, CYB5, CYC1, DAP2IP, DES, DNCL1, E2F1, ECGF1, EDG1, EFNA1, EFNA3, EFNB2, EGF, EGFR, EGFRvIII, ELAC2, ENG, ENO1, ENO2, ENO3, EPHB4, ERBB2 (Her-2), EREG, ERK8, ESR1, ESR2, F3 (TF), FAP, FASN, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR3, FIGF, FLJ12584, FLJ25530, FLRT1 (fibronectin), FLT1, FOSL1 (FRA-1), GABRP (GABA-A), GAGEB1, GAGEC1, GATA3, GD2, GGT1, GNAS1, GNRH1, GPC3, GRP, GSN (Gelsolin), GSTP1, HGF, HGFR (MET), HIP1, HUMCYT2A, ID2, IFNA1, IFNB1, IFNG, IGF1, IGF1R, IGF2, IGFBP2, IGFBP3, IGFBP6, Igκ light chain, IL12A, IL13RA2, IL1A, IL1B, IL2, IL24, IL29, IL2RA, IL3RA (CD123), IL6, IL6R, IL6ST (glycoprotein 130), IL8, ILK, INHA, INSL3, INSL4, ITGA1, ITGA6 (a6 integrin), ITGAV, ITGB3, ITGB4 (84 integrin), JAG1, JUN, K6HF, KAII, KDR, KLF5 (GC Box BP), KLK10, KLK12, KLK13, KLK14, KLK15, KLK3, KLK4, KLK5, KLK6, KLK9, KRT1, KRT19, KRT2A, KRTHB6 (hair-specific type II keratin), LAMA5, Lewis-Y, MACMARCKS, MAP2K7 (c-Jun), MDK, MIB1, MKI67 (Ki-67), MMP2, MMP9, MSLN (mesothelin), MSMB, MT3 (metallothionein-3), MTSS1, MUC1 (mucin), MUC16, MYC, NGFB (NGF), NGFR, a NKG2D ligand, NME1 (NM23A), NOX5, NR0B1, NR0B2, NR1D1, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NTN4, ODZ1, P1AS2, P1K3CG, PAP, PART1, PATE, PAWR, PCA3, PCNA, PDGFA, PECAM1, PF4, PGF, PGR, PLAU (UPA), Plectin, PLG, PLXDC1, PPID, PR1, PRKCQ, PRKD1, PRL, PROK2, PSAP, PSCA, PSMA, PTEN, PTGS2 (COX-2), RAC2 (p21-Rac2), RARB, ROBO2, ROR-1, S100A2, SCGB1D2 (lipophilin B), SCGB2A1 (mammaglobin-2), SCGB2A2 (mammaglobin-1), SERPINA3, SERPINB5 (maspin), SERPINE1 (PAI-1), SERPINF1, SHBG, SHBQ, SLC2A2, SLC33A1, SLC43A1, SPRR1B (Spr1), STAB1, STEAP, STEAP2, TEK, TGFA, TGFB1, TGFB1I1, TGFB1I1, TGFB2, TGFB3, TGFBR1, TGRA, THBS1 (thrombospondin-1), THBS2, THBS4, TIE (Tie-1), TIMP3, TNF, TNFAIP2 (B94), TNFRSF6 (Fas), TNFRSF7 (BCMA), TNFRSF8 (CD30), TNFSF10, TNFSF6 (FasL), TOP2A (topoisomerase-2α), TP53, TPM1, TPM2, TRPC6, VEGF, VEGFC, and any combination thereof.

In certain exemplary embodiments, the one or more antigens are different.

In certain exemplary embodiments, the one or more antigens are on the same cell.

In certain exemplary embodiments, the one or more antigens are on at least two cells.

In certain exemplary embodiments, each of the at least two cells are of the same cell type.

In certain exemplary embodiments, each of the at least two cells are of a different cell type.

In certain exemplary embodiments, the cell type is selected from the group consisting of a cytotoxic cell and a cancer cell.

In certain exemplary embodiments, the cytotoxic cell is a T cell selected from the group consisting of a naïve T cell, a central memory T cell, and an effector memory T cell.

In certain exemplary embodiments, the cytotoxic cell is selected from the group consisting of a natural killer (NK) cell, an activated NK cell, a neutrophil, an eosinophil, a basophil, a B-cell, a macrophage, and a lymphokine-activated killer cell.

In certain exemplary embodiments, one of the at least two cells is a cancer cell.

In another aspect, a nucleic acid sequence encoding a CAR or multispecific CAR of the present disclosure is provided.

In certain exemplary embodiments, an expression vector comprises the nucleic acid sequence.

In certain exemplary embodiments, the expression vector further comprising a nucleic acid sequence encoding a cytokine operably linked to a T-cell activation responsive promoter.

In certain exemplary embodiments, the cytokine is IL-12.

In certain exemplary embodiments, the expression vector is selected from the group consisting of a lentivirus vector, a gamma retrovirus vector, a foamy virus vector, an adeno-associated virus vector, an adenovirus vector, a pox virus vector, a herpes virus vector, an engineered hybrid virus vector, and a transposon mediated vector.

In another aspect, a method of producing an engineered cell comprising introducing an expression vector of the present disclosure into a cell to produce the engineered cell, is provided.

In another aspect, an engineered cell comprising a nucleic acid sequence of the present disclosure, or an expression vector of the present disclosure, is provided.

In certain exemplary embodiments, the cell is a T cell.

In certain exemplary embodiments, the T cell is selected from the group consisting of a naïve T cell, a central memory T cell, and an effector memory T cell.

In certain exemplary embodiments, the cell is selected from the group consisting of a natural killer (NK) cell, an activated NK cell, a neutrophil, an eosinophil, a basophil, a B-cell, a macrophage, and a lymphokine-activated killer cell.

In certain exemplary embodiments, the nucleic acid sequence is integrated into the genome of the cell.

In certain exemplary embodiments, the engineered cell produces the CAR or multispecific CAR in a sufficient amount for therapeutic use.

In another aspect, a pharmaceutical composition, comprising: i) one or more CAR or multispecific CAR of the present disclosure, an expression vector of the present disclosure, or an engineered cell of the present disclosure; and ii) a pharmaceutically acceptable carrier or excipient, is provided.

In another aspect, a method of treating cancer in a subject in need thereof, the method comprising: i) introducing a CAR or multispecific CAR of the present disclosure, or introducing an expression vector of the present disclosure, into a cell obtained from the subject to produce an engineered cell; and ii) administering the engineered cell to the subject, thereby treating the cancer, is provided.

In certain exemplary embodiments, the expression vector is selected from the group consisting of a lentivirus vector, a gamma retrovirus vector, a foamy virus vector, an adeno-associated virus vector, an adenovirus vector, a pox virus vector, a herpes virus vector, an engineered hybrid virus vector, and a transposon mediated vector.

In certain exemplary embodiments, the cell is a T cell selected from the group consisting of a naïve T cell, a central memory T cell, and an effector memory T cell.

In certain exemplary embodiments, the cell is selected from the group consisting of a natural killer (NK) cell, an activated NK cell, a neutrophil, an eosinophil, a basophil, a B-cell, a macrophage, and a lymphokine-activated killer cell.

In certain exemplary embodiments, the nucleic acid sequence is integrated into the genome of the cell.

In certain exemplary embodiments, the engineered cell produces the CAR or multispecific CAR in a sufficient amount for therapeutic use.

In certain exemplary embodiments, the cancer is a solid tumor or a hematological tumor.

In certain exemplary embodiments, the solid tumor is selected from the group consisting of a fibrosarcoma, a myxosarcoma, a liposarcoma, a chondrosarcoma, an osteosarcoma, and other sarcomas, a synovioma, a mesothelioma, an Ewing's tumor, a leiomyosarcoma, a rhabdomyosarcoma, a colon carcinoma, a lymphoid malignancy, a pancreatic cancer, a breast cancer, a lung cancer, an ovarian cancer, a prostate cancer, a hepatocellular carcinoma, a squamous cell carcinoma, a basal cell carcinoma, an adenocarcinoma, a sweat gland carcinoma, a medullary thyroid carcinoma, a papillary thyroid carcinoma, a pheochromocytomas sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a Wilms' tumor, a cervical cancer, a testicular tumor, a seminoma, a bladder carcinoma, a melanoma, a glioma, a glioblastoma, an astrocytoma, a CNS lymphoma, a germinoma, a medulloblastoma, a Schwannoma craniopharyogioma, an ependymoma, a pinealoma, a hemangioblastoma, an acoustic neuroma, an oligodendroglioma, a menangioma, a neuroblastoma, a retinoblastoma, and a brain metastasis.

In certain exemplary embodiments, the hematologic tumor is selected from the group consisting of a leukemia, a polycythemia vera, a lymphoma, a Hodgkin's lymphoma, a non-Hodgkin's lymphoma, a multiple myeloma, a Waldenstrom's macroglobulinemia, a heavy chain disease related tumor, a myelodysplastic syndrome related tumor, a hairy cell leukemia, and a myelodysplasia.

In another aspect, a T cell activating bispecific antigen binding molecule comprising an FN3 domain containing polypeptide fused to a single chain Fv (scFv), wherein the FN3 domain polypeptide is capable of specific binding to a target antigen and the scFv is capable of specific binding to an activating T cell antigen is provided.

In certain exemplary embodiments, the FN3 domain containing polypeptide comprises an FN3 domain comprising:
  a) regions A, AB, B, C, CD, D, E, EF, F, and G having wild type amino acid sequences of a selected native fibronectin type 3 polypeptide, and
  b) loop regions BC, DE, and FG having selected amino acid lengths.

In certain exemplary embodiments, the BC loop length is 11, 14, or 15 amino acids.

In certain exemplary embodiments, the DE loop length is 6 amino acids.

In certain exemplary embodiments, the FG loop length is 8, or 11 amino acids.

In certain exemplary embodiments, the FN3 domain polypeptide comprises the 14$^{th}$ fibronectin type 3 module of human fibronectin.

In certain exemplary embodiments, the FN3 domain polypeptide comprises the 10$^{th}$ fibronectin type 3 module of human fibronectin.

In certain exemplary embodiments, the Fc domain is an IgG, specifically an IgG1 or IgG4, Fc domain.

In certain exemplary embodiments, the Fc domain is a human Fc domain.

In certain exemplary embodiments, the Fc domain exhibits reduced binding affinity to an Fc receptor and/or reduced effector function, as compared to a native IgG1 Fc domain.

In certain exemplary embodiments, the Fc domain comprises one or more amino acid substitution that reduces binding to an Fc receptor and/or effector function.

In certain exemplary embodiments, not more than one antigen binding moiety capable of specific binding to an activating T cell antigen is present.

In certain exemplary embodiments, the FN3 domain containing polypeptide comprises one or more FN3 domain monomers.

In certain exemplary embodiments, the FN3 domain containing polypeptide comprises two FN3 domain monomers.

In certain exemplary embodiments, the FN3 domain containing polypeptide comprises three FN3 domain monomers.

In certain exemplary embodiments, each of the one or more FN3 domain monomers are linked together by a linker sequence.

In certain exemplary embodiments, the one or more FN3 domain monomers are each capable of specific binding to a distinct epitope of the target antigen.

In certain exemplary embodiments, the one or more FN3 domain monomers are each capable of specific binding to an overlapping epitope of the target antigen.

In certain exemplary embodiments, the target antigen is AXL.

In certain exemplary embodiments, the activating T cell antigen is CD3.

In certain exemplary embodiments, the FN3 domain containing polypeptide capable of binding to AXL comprises an amino acid sequence selected from the group consisting of SEQ ID NOs: 33-36.

In certain exemplary embodiments, the binding molecule comprises an amino acid sequence selected from the group consisting of SEQ ID NOs: 37-39.

In certain exemplary embodiments, a nucleic acid sequence encoding the T cell activating bispecific antigen binding molecule of any of the above aspects is provided.

In certain exemplary embodiments, an expression vector, comprising the nucleic acid sequence of any of the above aspect is provided.

In certain exemplary embodiments, a host cell comprising the nucleic acid of any of the above aspects is provided.

In another aspect, a method of producing the T cell activating bispecific antigen binding molecule of any of the above aspects, comprising the steps of a) culturing the host cell of claim of any of the above aspects under conditions suitable for the expression of the T cell activating bispecific antigen binding molecule and b) recovering the T cell activating bispecific antigen binding molecule.

In certain exemplary embodiments, a T cell activating bispecific antigen binding molecule produced by the method of any of the above aspects is provided.

In certain exemplary embodiments, a pharmaceutical composition comprising the T cell activating bispecific antigen binding molecule of any of the above aspects, and a pharmaceutically acceptable carrier, is provided.

In certain exemplary embodiments, the T cell activating bispecific antigen binding molecule of any of the above aspects, or the pharmaceutical composition of any of the above aspects, for use as a medicament, is provided.

In certain exemplary embodiments, the T cell activating bispecific antigen binding molecule of any of the above aspects, or the pharmaceutical composition of any of the above aspects, for use in the treatment of a disease in an individual in need thereof, is provided.

In certain exemplary embodiments, the disease is cancer.

In certain exemplary embodiments, a method for inducing lysis of a target cell, comprising contacting a target cell with the T cell activating bispecific antigen binding molecule of any of the above aspects, or the pharmaceutical composition of any of the above aspects, in the presence of a T cell, is provided.

In another aspect, a T cell activating bispecific antigen binding molecule comprising an FN3 domain containing polypeptide fused to a single chain Fv (scFv), wherein the FN3 domain containing polypeptide is capable of specific binding to AXL, and the scFv is capable of specific binding to CD3, is provided.

In certain exemplary embodiments, the T cell activating bispecific antigen binding molecule comprises an amino acid sequence set forth in any one of SEQ ID NOs: 37-39.

In another aspect, a T cell activating bispecific antigen binding molecule comprising an FN3 domain containing polypeptide fused to a single chain Fv (scFv), wherein the FN3 domain containing polypeptide comprises a dimer of FN3 domain monomers each capable of specific binding to AXL, and wherein the scFv is capable of specific binding to CD3, is provided.

In certain exemplary embodiments, the T cell activating bispecific antigen binding molecule comprises an amino acid sequence set forth in SEQ ID NO:40.

In another aspect, a T cell activating bispecific antigen binding molecule comprising an FN3 domain containing polypeptide fused to a single chain Fv (scFv), wherein the FN3 domain containing polypeptide comprises a trimer of FN3 domain monomers each capable of specific binding to AXL, and wherein the scFv is capable of specific binding to CD3, is provided.

In certain exemplary embodiments, the T cell activating bispecific antigen binding molecule comprises an amino acid sequence set forth in SEQ ID NO:41.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 5 depicts FACS analysis of specificity screening.

FIG. 6 depicts a table of binding affinities measured by Bio-Layer Interferometry (BLI) for various AXL-specific FN3 binders.

DETAILED DESCRIPTION

Figure 1:
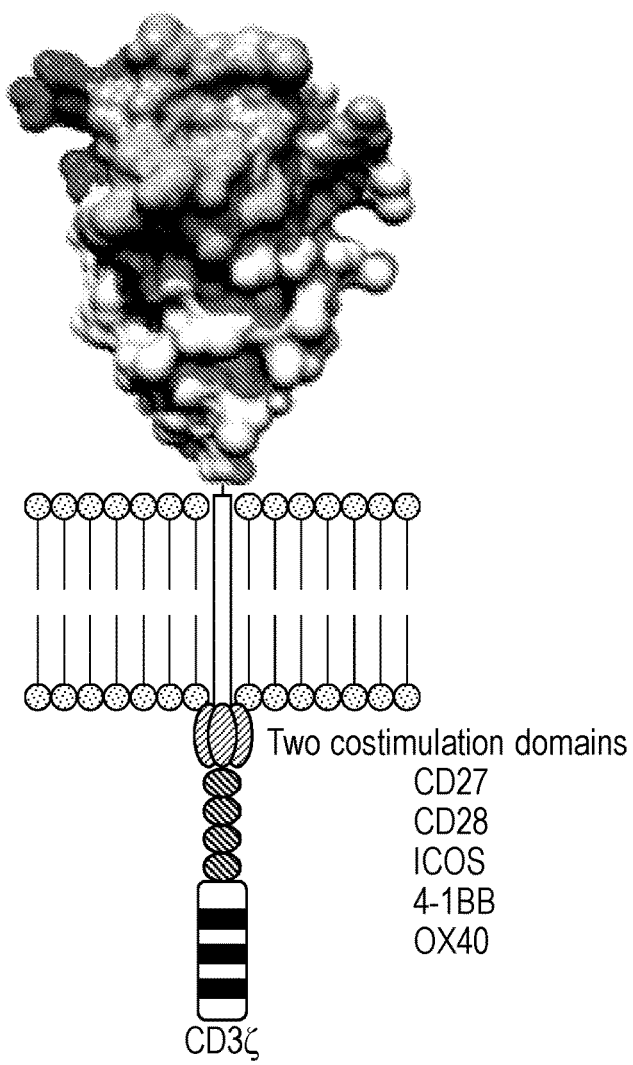
FIG. 1 depicts a schematic of a subject FN3 CAR of the present disclosure, comprising two costimulation domains.

The present disclosure provides CARs for binding with a target antigen, comprising at least one antigen specific targeting region comprising an FN3 domain polypeptide. The present disclosure also provides multispecific FN3 CARs for binding with two or more target antigens, comprising at least one or more antigen specific targeting regions comprising an FN3 domain polypeptide. The present disclosure also provides compositions and methods of treatment relating to the use of the subject FN3 CARs of the invention. Suitable diseases that may be addressed by the present invention include, without limitation, various solid tumors and hematological cancers.

The invention described herein is largely based on the need for improving on the limitations of current CARs which comprise single-chain variable fragments (scFvs). Such limitations include, e.g., that scFvs are large proteins with immunogenicity issues, the association of current CARs with tonic signaling due to instability and flexibility of their structures, the potential for VH/VL domain swapping and multimer formation through framework region interactions, the potential for incorrect folding, the potential for aggregation, and the potential for depletion of CAR-T cells.

It is to be understood that the compositions and methods described in this disclosure are not limited to the particular compositions, methods, or experimental conditions disclosed herein, as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, $2^{nd}$ edition).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics, and protein and nucleic acid chemistry described herein are those well-known and commonly used in the art. The methods and techniques provided herein are generally performed according to conventional methods well known in the art and as described in various general and more specific references that are cited and discussed throughout the present specification unless otherwise indicated. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

So that the invention may be more readily understood, certain terms are first defined. It is to be understood that the terminology used herein is for the purpose of describing particular embodiments only, and is not intended to be limiting, The term "amino acid" or "amino acid residue" typically refers to an amino acid having its art recognized definition such as an amino acid selected from the group consisting of: alanine (Ala, A); arginine (Arg, R); asparagine (Asn, N); aspartic acid (Asp, D); cysteine (Cys, C); glutamine (Gln, Q); glutamic acid (Glu, E); glycine (Gly, G); histidine (His, H); isoleucine (Ile, I): leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V) although modified, synthetic, or rare amino acids may be used as desired.

"Chemically equivalent amino acids" refer to amino acids that have similar steric, charge, and solubility properties. One common scheme groups amino acids in the following way: (1) glycine, having a hydrogen side chain; (2) alanine (Ala, A), valine (Val, V), leucine (Leu, L), and isoleucine (Iso, I), having hydrogen or an unsubstituted aliphatic side chain; (3) serine (Ser, S) and threonine (Thr, T), having an aliphatic side chain bearing a hydroxyl group; (4) aspartic (Asp, D) and glutamic acid (Glu, E), having a carboxyl containing side chain; (5) asparagine (Asn, N) and glutamine (Glu, Q), having an aliphatic side chain terminating in an amide group; (6) arginine (Arg, R) lysine (Lys, L) and histidine (His, H), having an aliphatic side chain terminating in a basic amino group; (7) cysteine (Cys, C) and methionine (Met, M), having a sulfur containing aliphatic side chain; (8) tyrosine (Tyr, Y) and phenylalanine (Phe, F), having an aromatic side chain; and (9) tryptophan (Trp, W), praline (Pro, P), and histidine (His, H), having a heterocyclic side chain.

The term "conserved amino acid residue" or "fixed amino acid" refers to an amino acid residue determined to occur with a frequency that is high, typically at least 50% or more (e.g., at about 60%, 70%, 80%, 90%, 95%, or 100%), for a given residue position. When a given residue is determined to occur at such a high frequency, i.e., above a threshold of about 50%, it may be determined to be conserved and thus represented in the libraries of the invention as a "fixed" or "constant" residue, at least for that amino acid residue position in the loop region being analyzed.

"Fibronectin type 3 (FN3) proteins" refer to a group of proteins composed of monomeric subunits having Fibronectin type 3 (FN3) structure or motif made up of seven β-strands with three connecting loops. β-strands A, B, and E form one half R-sandwich and β-strands C, D, F, and G form the other half, and having molecular weights of about 94 amino acids and molecular weights of about 10 kDa. The overall fold of the FN3 domain is closely related to that of the immunoglobulin domains, and the three loops near the N-terminus of FN3, named BC, DE, and FG, can be considered structurally analogous to the antibody variable heavy (VH) domain complementarity-determining regions, CDR1, CDR2, and CDR3, respectively. Fibronectin itself is composed of 16 different modules or domains. A given module of an FN3 protein is identified by module number and protein name, for example, the $14^{th}$ FN3 module of human fibronectin (14/FN or 14/FN3), the $10^{th}$ FN3 module of human fibronectin (10/FN or 10/FN3), the $1^{st}$ FN3 module of tenascin (1/tenascin), and so forth.

"Fibronectin type 3 (FN3) domain polypeptides" or "FN3 polypeptides" refer to polypeptides having the Fibronectin type 3 domain or module discussed herein, where one or more modules will make up a fibronectin-type protein (FN3 protein), such as the sixteen different FN3 modules making up human fibronectin (FN), and the 15 different FN3 modules making up tenascin. Individual FN3 domain polypeptides are referred to by module number and protein name, e.g., the $10^{th}$ or $14^{th}$ module of human fibronectin (10/FN or 14/FN) or the $1^{st}$ module of tenascin (1/tenascin).

The term "framework region" refers to the art recognized portions of a fibronectin beta-strand scaffold that exist between the more divergent loop regions. Such framework regions are typically referred to the beta strands A through G that collectively provide a scaffold for where the six defined loops can extend to form a ligand contact surface(s). In fibronectin, the seven beta-strands orient themselves as two beta-pleats to form a beta sandwich. The framework region may also include loops AB, CD, and EF between strands A and B, C and D, and E and F, respectively.

The term "loop region" refers to a peptide sequence not assigned to the beta-strand pleats. In the fibronectin binding scaffold there are six loop regions, three of which are known to be involved in binding domains of the scaffold (BC, DE, and FG), and three of which are located on the opposite sided of the polypeptide (AB, EF, and CD). In the present invention, sequence diversity is built into one or more of the BC, DE, and FG loops, whereas the AB, CD, and EF loops are generally assigned the wildtype amino sequences of the FN3 polypeptide from which other framework regions of the polypeptide are derived.

A "consensus" amino acid in a BC, DE, or FG loop of an FN3 polypeptide is a conserved amino acid or a selected one of a semi-conserved amino acids.

The term "ligand" or "antigen" refers to compounds which are structurally/chemically similar in terms of their basic composition. Typical ligand classes are proteins (polypeptides), peptides, polysaccharides, polynucleotides, and small molecules. Ligand can be equivalent to "antigens" when recognized by specific antibodies.

The term "antigen" or "Ag" as used herein is defined as a molecule that provokes an immune response. This immune response may involve either antibody production, or the activation of specific immunologically-competent cells, or both. A person skilled in the art will understand that any macromolecule, including virtually all proteins or peptides, can serve as an antigen. Furthermore, antigens can be derived from recombinant or genomic DNA. A person skilled in the art will understand that any DNA, which includes a nucleotide sequence or a partial nucleotide sequence encoding a protein that elicits an immune response, therefore encodes an "antigen" as that term is used herein. Furthermore, one skilled in the art will understand that an antigen need not be encoded solely by a full length nucleotide sequence of a gene. Moreover, a skilled person will understand that an antigen need not be encoded by a "gene" at all. It is readily apparent that an antigen can be generated, synthesized or can be derived from a biological sample. Such a biological sample can include, but is not limited to a tissue sample, a tumor sample, a cell or a biological fluid.

The term "antibody" as used herein refers to intact immunoglobulin molecules, as well as fragments of immunoglobulin molecules that are capable of binding to an epitope of an antigen.

The term "chimeric antigen receptor (CAR)" refers to a protein comprising an extracellular domain capable of binding to an antigen, a transmembrane domain derived from a polypeptide different from a polypeptide from which the extracellular domain is derived, and at least one intracellular domain. The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

The term "conditionally active chimeric antigen receptor" refers to a variant, or mutant, of a wild-type protein which is more or less active than the parent wild-type protein under one or more normal physiological conditions. This conditionally active protein also exhibits activity in selected regions of the body and/or exhibits increased or decreased activity under aberrant, or permissive, physiological conditions.

The term "normal physiological condition" as used herein refers to one of temperature, pH, osmotic pressure, osmolality, oxidative stress, electrolyte concentration, a concentration of a small organic molecule such as glucose, lactic acid, pyruvate, nutrient components, other metabolites, and the like, a concentration of another molecule such as oxygen, carbonate, phosphate, and carbon dioxide, as well as cell types, and nutrient availability, which would be considered within a normal range at the site of administration, or at the tissue or organ at the site of action, to a subject.

The term "about" or "approximately" means within 20%, such as within 10%, within 5%, or within 1% or less of a given value or range.

As used herein, "administer" or "administration" refers to the act of injecting or otherwise physically delivering a substance as it exists outside the body into a patient, such as by, but not limited to, pulmonary, mucosal, intradermal, intravenous, intramuscular delivery and/or any other method of physical delivery described herein or known in the art. When a disease, or a symptom thereof, is being managed or treated, administration of the substance typically occurs after the onset of the disease or symptoms thereof.

As used herein, the term "composition" is intended to encompass a product containing the specified ingredients in, optionally, the specified amounts, as well as any product which results, directly or indirectly, from combination of the specified ingredients in, optionally, the specified amounts.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sports animals, and pets. In one embodiment, the subject is a mammal, such as a human, having a disease (e.g., a solid tumor, or a hematological cancer).

As used herein, the term "therapy" refers to any protocol, method and/or agent that can be used in the prevention, management, treatment and/or amelioration of a disease or a symptom related thereto, such as a solid tumor or a hematological cancer. In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as a solid tumor or a hematological cancer known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, such as a solid tumor or a hematological cancer, resulting from the administration of one or more therapies (including, but not limited to, the administration of one or more prophylactic or therapeutic agents, such a composition provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Fibronectin Type 3 Domain Polypeptides

Fibronectin type proteins refer to a group of proteins composed of monomeric subunits having FN3 structure or motif made up of seven β-strands with three connecting loops. β-strands A, B, and E form one half R-sandwich and β-strands C, D, F, and G form the other half, and having molecular weights of about 94 amino acids and molecular weights of about 10 kDa. The overall fold of the FN3 domain is closely related to that of the immunoglobulin domains, and the three loops near the N-terminus of FN3, named BC, DE, and FG, can be considered structurally analogous to the antibody variable heavy (VH) domain complementarity-determining regions, CDR1, CDR2, and CDR3, respectively.

Representative FN3 proteins include, angiopoietin 1 receptor, contacting protein, cytokine receptor common β chain, Down syndrome cell adhesion protein, fibronectin, and others that are known in the art. Fibronectin itself is composed of 16 different modules or domains. A given module of an FN3 protein is identified by module number and protein name, for example, the $14^{th}$ FN3 module of human fibronectin (14/FN or 14/FN3), the $10^{th}$ FN3 module of human fibronectin (10/FN or 10/FN3), the $1^{st}$ FN3 module of tenascin (1/tenascin), and so forth.

Fibronectin is involved in many cellular processes, including tissue repair, embryogenesis, and blood clotting, by serving as a general cell adhesion molecule anchoring cells to integrin, collagen or other proteoglycan substrates. In addition, fibronectin can serve to organize the extracellular matrix binding to different components, such as heparin, to membrane-bound receptors on cell surfaces. The amino acid sequence of fibronectin reveals three types of internally homologous repeats or modules separated by (usually) short connecting sequences. There are 12 type I, 2 type II and 16 type III modules, and referred to as FN I (FN1), FN II (FN2) and FN III (FN3) respectively. Each FN module constitutes an independently folded unit, often referred to as a domain. As noted above, modules homologous to those in fibronectin are also found in other proteins, especially the FN3 motif which is one of the most ubiquitous of all modules, being found in extracellular receptor kinases, phosphatases, tenascin and others. Since its discovery, this FN3 domain has been found in many animal proteins and is estimated to occur in 2% of the proteins sequenced to date. Within fibronectin itself, there are sixteen FN3 domains that have remarkably similar tertiary structures. While FN3 conformation are highly conserved, the similarity between different modules of the same type within a given fibronectin protein is quite low typically less than 20%. In contrast, the amino acid sequence homology for the same FN3 modules across multiple species is notably higher, approximately 80%-90%.

Fibronectin modules fold independently and thus can exist in isolation from their neighbors. The three dimensional structures of several examples of each type of fibronectin module have been determined. As expected from the well-known relationship between amino acid sequence and 3D structure, modules of the same type have similar folds. All three types of modules are composed almost exclusively of antiparallel R sheets and turns, with little or no alpha helix. In FN3 modules, the top sheet contains four antiparallel beta strands and the bottom sheet is three-stranded. Disulfide bridges do not stabilize FN3 structure. Instead, this occurs solely through hydrophobic interactions in the module core.

The present invention provides a CAR for binding with a target antigen, comprising at least one antigen specific targeting region comprising an FN3 domain polypeptide.

In one embodiment, the FN3 domain polypeptide is generated by walk-through mutagenesis, as described in U.S. Pat. No. 8,680,019, and incorporated herein by reference in its entirety.

In another embodiment, the FN3 domain polypeptides is selected from a natural variant combinatorial library of FN3 domain polypeptides, further described in U.S. Pat. No. 8,680,019.

In some embodiments, each FN3 domain polypeptide may be specific for an antigen. In some embodiments, each FN3 domain polypeptide may be specific for a different antigen. In some embodiments, an FN3 domain containing polypeptide is specific for a single antigen. In some embodiments, an FN3 domain containing polypeptide comprises two or more FN3 domains each specific for an antigen. In some embodiments, a bispecific FN3 domain containing polypeptide comprises two FN3 domains, wherein the first FN3 domain is specific for an antigen, and wherein the second FN3 domain is specific for a different antigen. In some embodiments, a multispecific FN3 domain containing polypeptide comprises two or more FN3 domains, wherein the first FN3 domain is specific for an antigen, wherein the second FN3 domain is specific for a different antigen, and wherein subsequent FN3 domains are specific for subsequent antigens.

In some embodiments, one or more FN3 domain polypeptides may have overlapping specificity for an antigen. For example, an FN3 domain containing polypeptide may comprise a dimer of FN3 domains, each of which binds to the same antigen (e.g., different epitopes of the same antigen). In some embodiments, an FN3 domain containing polypeptide may comprise a trimer of FN3 domains, each of which binds to the same antigen (e.g., different epitopes of the same antigen).

In some embodiments, an FN3 domain containing polypeptide may further comprise a single-chain variable fragment (scFv), referred to herein as an FN3 domain-scFv fusion. As used herein, an "FN3 domain-scFv fusion" refers to a polypeptide comprising an FN3 domain polypeptide specific for an antigen, and an scFv specific for an antigen. In some embodiments, an FN3 domain-scFv fusion of the present disclosure comprises one or more FN3 domains specific for one or more target antigens, and one or more scFvs specific for one or more target antigens. For example, an AXL-CD3 FN3 domain-scFv fusion comprises one or more FN3 domains specific for the tyrosine-protein kinase AXL, and comprises one or more scFvs specific for the cell-surface CD3 protein. In such an embodiment, the AXL-CD3 FN3 domain-scFV fusion may also be referred to as an AXL-CD3 FN3 domain-scFv bispecific T cell engager (BiTE). In such an embodiment, an AXL-CD3 FN3 domain-scFv fusion comprises binding affinity for AXL (e.g., through the AXL specific FN3 domains) and binding affinity for CD3 (e.g., through the CD3 specific scFv). For FN3 domain-scFv fusions that comprise binding affinity for a T cell receptor component (e.g., CD3), those FN3 domain-scFv fusions may be referred to as FN3 domain-scFv T cell engagers.

In some cases, the FN3 domain portion of the FN3 domain-scFv fusion may comprise a monomer of a target specific FN3 domain. In some embodiments, the FN3 domain portion may comprise a dimer, a trimer, or more monomers of a target specific FN3 domain. In one embodiment, each monomer in the dimer, or trimer, etc., can be specific for a single antigen (e.g., different epitopes of the same antigen). For example, an AXL-CD3 FN3 domain-scFv fusion may comprise a dimer of FN3 domains each specific for AXL (e.g., different epitopes of AXL), and further comprises an scFv specific for CD3. In another example, an AXL-CD3 FN3 domain-scFv fusion may comprise a trimer of FN3 domains each specific for AXL (e.g., different epitopes of AXL), and further comprises an scFv specific for CD3. In one embodiment, each monomer in the dimer, or trimer, etc., can be specific for different antigens.

The antigens targeted by an FN3 domain of the present disclosure are present on the surface or inside of cells in a tissue that targeted for removal, such as tumors, glandular (e.g. prostate) hyperplasia, and hematological malignancies. While the surface antigens are more efficiently recognized and bound by the one or more FN3 domains, intracellular antigens may also be targeted by the FN3 domains. In some embodiments, the target antigens are preferably specific for cancer. Examples of target antigens include antigens expressed by various immune cells, carcinomas, sarcomas, lymphomas, leukemia, germ cell tumors, blastomas, and cells associated with various hematologic diseases.

Antigens specific for cancer which may be targeted by the one or more FN3 domains include one or more of 4-1BB, 5T4, adenocarcinoma antigen, alpha-fetoprotein, BAFF, β-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-IC, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

Antigens specific for inflammatory diseases which may be targeted by the one or more FN3 domains include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-a, IFN-γ, IgE, IgE Fc region, IL-1, IL-12, IL-23, IL-13, IL-17, IL-17A, IL-22, IL-4, IL-5, IL-5, IL-6, IL-6 receptor, integrin a4, integrin α4β7, LFA-1 (CD11a), MEDI-528, myostatin, OX-40, rhuMAb β7, scleroscin, SOST, TGF beta 1, TNF-a or VEGF-A.

Antigens specific for cancer include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

In one embodiment, the FN3 domains may target antigens that engage cancer-treating cells, such as NK cells and other cells mentioned herein, to activate the cancer-treating cells by acting as immune effector cells. One example of this is an FN3 domain that targets the CD16A antigen to engage NK cells to fight CD30-expressing malignancies. The bispecific, tetravalent AFM13 antibody is an example of an antibody that can deliver this effect. Further details of this type of embodiment can be found, for example, in Rothe et al., Blood (2015) 125 (26): 4024-4031.

In one embodiment, the FN3 domains may target antigens such as AXL receptor tyrosine kinase (AXL), MER receptor tyrosine kinase (MER), B-cell maturation protein (BCMA; also known as TNF receptor superfamily member 17 (TNFRSF17)), programmed cell death 1 ligand 1 (PDL1; also known as CD274), programmed cell death protein 1 (PD-1; also known as CD279), the CD3 T cell co-receptor (CD3), cytotoxic T-lymphocyte-associated protein 4 (CTLA-4; also known as CD152), vascular endothelial growth factor receptor 2 (VEGFR2), frizzled class receptor 2 (FZD2), frizzled class receptor 4 (FZD4), epithelial cell adhesion molecule (EPCAM), Siglec-3 (also known as CD33), prostate-specific membrane antigen (PSMA), cluster of differentiation 28 (CD28), 4-1BB (also known as CD137, or tumor necrosis factor receptor superfamily member 9 (TNFRSF9)), Fc-gamma receptor IIIa (CD16a), the inhibitor NK cell receptor CD94/NKG2A, MHC class I chain-related protein A (MICA), MHC class I chain-related protein B (MICB), cluster of differentiation 38 (CD38; also known as cyclic ADP ribose hydrolase), and activating receptor NKp46 (also known as CD335).

Accordingly, various types of walk-through mutagenesis and natural-variant combinatorial FN3 domain polypeptide libraries can be generated, and such libraries would be useful in screening for the presence of one or more FN3 domain polypeptides having a selected binding or enzymatic activity.

For example, a library of FN3 domain polypeptides can include (a) regions A, AB, B, C, CD, D, E, EF, F, and G having wild type amino acid sequences of a selected native FN3 domain polypeptide, and (b) loop regions BC, DE, and FG having selected lengths. At least one selected loop region of a selected length contains a library of natural-variant combinatorial sequences or walk-through mutagenesis sequences encoded by a library of coding sequences that encode at each loop position, a conserved or selected semi-conserved consensus amino acid, and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

In some embodiments, an FN3 domain polypeptide of the present invention includes loop regions BC, DE, and FG having selected lengths. The selected loop lengths of a FN3 domain polypeptide of the invention includes BC having a loop length of 11 amino acids, BC having a loop length of 14 amino acids, BC having a loop length of 15 amino acids, DE having a loop length of 6 amino acids, FG having a loop length of 8 amino acids, and/or FG having a loop length of 11 amino acids.

In some embodiments, an FN3 domain polypeptide of the present invention includes regions A, AB, B, C, CD, D, E, EF, F, and G having wild type amino acid sequences of a selected native FN3 domain polypeptide. In one embodiment, the selected native FN3 domain polypeptide is a $14^{th}$ FN3 module of human fibronectin. In one embodiment, the selected native FN3 domain polypeptide is a $10^{th}$ FN3 module of human fibronectin.

In certain embodiments, a library of FN3 domain polypeptides is screened for one or more FN3 domain polypeptides having a selected binding or enzymatic activity. The screening may involve, for example, contacting a library of FN3 domain polypeptides with a target antigen/substrate, wherein each FN3 domain polypeptide comprises a fibronectin binding domain, and identifying the FN3 domain polypeptide comprising the fibronectin binding domain that binds the target antigen/substrate. The screening may be performed by, for example, positive physical clone selection by FACS, phage panning, or selective ligand retention.

In some embodiments, upon identifying a target specific FN3 domain polypeptide, a chimeric antigen receptor may be assembled by ligating the target specific FN3 domain polypeptide sequence together with sequences encoding the individual domains of a chimeric antigen receptor.

Chimeric Antigen Receptors

The present invention provides a CAR for binding with a target antigen, comprising at least one antigen specific targeting region comprising an FN3 domain polypeptide, i.e., an "FN3 CAR." In some embodiments, the FN3 CAR is a multispecific CAR comprising at least two antigen specific targeting regions, wherein one or more of the antigen specific targeting regions comprise a FN3 domain polypeptide. In one embodiment, the FN3 CAR is a multi-specific CAR comprising at least two antigen specific targeting regions, wherein each of the antigen specific targeting regions comprise an FN3 domain polypeptide. In some embodiments, once a target specific FN3 domain polypeptide is identified, a chimeric antigen receptor may be assembled by ligating the target specific FN3 domain polypeptide sequence together with sequences encoding the individual domains of a chimeric antigen receptor.

In some embodiments, a chimeric antigen receptor of the present invention is a chimeric artificial protein including at least one antigen specific targeting region (ASTR), a transmembrane domain (TM), and an intracellular signaling domain (ISD). In some embodiments, the FN3 CAR may further include an extracellular spacer domain (ESD) and/or a co-stimulatory domain (CSD).

The ASTR is an extracellular region of the CAR for binding to a specific target antigen including proteins, carbohydrates, and glycolipids. In some embodiments, the ASTR comprises a FN3 domain polypeptide having a target specific fibronectin binding domain. The ASTR may also include another protein functional domain to recognize and bind to the target antigen. Because the target antigen may have other biological functions, such as acting as a receptor or a ligand, the ASTR may alternatively include a functional domain for specifically binding with the antigen. Some examples of proteins with functional domains include linked cytokines (which leads to recognition of cells bearing the cytokine receptor), affibodies, ligand binding domains from naturally occurring receptors, soluble protein/peptide ligands for a receptor, for example on a tumor cell. Almost any molecule that is capable of binding to a given antigen with high affinity can be used in the ASTR, as will be appreciated by those skilled in the art.

In one embodiment, the FN3 CAR of the invention includes at least two ASTRs which target at least two different antigens or two epitopes on the same antigen. In an embodiment, the FN3 CAR includes three or more ASTRs which target at least three or more different antigens or epitopes. When a plurality of ASTRs is present in an FN3 CAR, the ASTRs may be arranged in tandem and may be separated by linker peptides. When two or more ASTRs are present in an FN3 CAR, the ASTRs are connected to each other covalently on a single polypeptide chain, through an oligo- or polypeptide linker, an Fc hinge or a membrane hinge region. In one embodiment, the linker connecting the two or more ASTRs is an oligopeptide linker. In one embodiment, the linker connecting the two or more ASTRs is an Fc hinge region. In one embodiment, the linker connecting the two or more ASTRs is a membrane hinge region.

In some embodiments, the transmembrane domain (TM) of the FN3 CAR is a region that is capable of spanning the plasma membrane of a cell (e.g., a cytotoxic cell). The transmembrane domain is for insertion into a cell membrane, e.g., a eukaryotic cell membrane. In some embodiments, the transmembrane domain is interposed between the one or more ASTRs and the intracellular portion of the FN3 CAR. The transmembrane domain can be selected from a transmembrane region of a transmembrane protein such as, for example, the transmembrane region of a Type I transmembrane protein, an artificial hydrophobic sequence or a combination thereof. Examples of the transmembrane domain include, without limitation, the transmembrane regions of the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137, CD154. In some embodiments, synthetic transmembrane domains may include a triplet of phenylalanine, tryptophan and valine. In some embodiments, a short oligo- or polypeptide linker, preferably between 2 and 10 amino acids in length, may form the linkage between the transmembrane domain and the intracellular signaling domain of the FN3 CAR. A glycine-serine doublet provides a particularly suitable linker between the transmembrane domain and the intracellular signaling domain of the FN3 CAR.

The FN3 CAR of the invention also includes an intracellular signaling domain. The intracellular signaling domain transduces the effector function signal and directs the cell (e.g., cytotoxic cell) to perform its specialized function, e.g., harming and/or destroying a target cell. Examples of the intracellular signaling domain include, without limitation, the ζ chain of the T cell receptor complex or any of its homologs, e.g., η chain, FcεRIγ and β chains, MB 1 (Igα) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcεRI, cytoplasmic tails of Fc receptors, an immunoreceptor tyrosine-based activation motif (ITAM) bearing cytoplasmic receptors, and combinations thereof.

In some embodiments, the intracellular signaling domains used in the FN3 CAR may include intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, *J. Clin. Oncol.* (2015) 33 (6): 651-653). Additionally, intracellular signaling domains include signaling domains used by NK and NKT cells (see, e.g., Hermanson and Kaufman, *Front. Immunol.* (2015) 6:195) such as signaling domains of NKp30 (B7-H6) (see, e.g., Zhang et al., *J. Immunol.* (2012) 189 (5): 2290-2299), and DAP 12 (see, e.g., Topfer et al., *J. Immunol.* (2015) 194 (7): 3201-3212), NKG2D, NKp44, NKp46, DAP10, and CD3z.

Intracellular signaling domains suitable for use in an FN3 CAR of the present disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound FN3 CAR, but is instead diffused in the cytoplasm.

Intracellular signaling domains suitable for use in an FN3 CAR of the present disclosure include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject FN3 CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., *Front. Immunol.* (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the FN3 CAR includes a cytoplasmic signaling domain of human CD3 zeta.

The FN3 CAR of the present invention may include a co-stimulatory domain, which has the function of enhancing cell proliferation, cell survival and development of memory cells for the cytotoxic cells that express the FN3 CAR. The FN3 CAR of the invention may include one or more co-stimulatory domains selected from co-stimulatory domains of proteins in the TNFR superfamily, CD28, CD137 (4-1BB), CD134 (OX40), Dap10, CD27, CD2, CD7, CD5, ICAM-1, LFA-1 (CD11a/CD18), Lck, TNFR-I, PD-1, TNFR-II, Fas, CD30, CD40, ICOS LIGHT, NKG2C, B7-H3, or any combinations thereof. If the FN3 CAR includes more than one co-stimulatory domain, these domains may be arranged in tandem, optionally separated by a linker. The co-stimulatory domain is an intracellular domain that may be located between the transmembrane domain and the intracellular signaling domain in the FN3 CAR.

Co-stimulatory domains suitable for use in a FN3 CAR of the present disclosure are generally polypeptides derived from receptors. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD28, ICOS, OX-40, BTLA, CD27, CD30, GITR, and HVEM.

In one embodiment, the co-stimulatory domain is derived from an intracellular portion of the transmembrane protein 4-1BB (also known as TNFRSF9; CD137; 4-1BB; CDw137; ILA; etc.). In one embodiment, the co-stimulatory domain is derived from an intracellular portion of the transmembrane protein CD28 (also known as Tp44). In one embodiment, the co-stimulatory domain is derived from an intracellular portion of the transmembrane protein ICOS (also known as AILIM, CD278, and CVID1). In one embodiment, the co-stimulatory domain is derived from an intracellular portion of the transmembrane protein OX-40 (also known as TNFRSF4, RP5-902P8.3, ACT35, CD134, OX40, TXGP1L). In one embodiment, the co-stimulatory domain is derived from an intracellular portion of the transmembrane protein BTLA (also known as BTLA1 and CD272). In one embodiment, the co-stimulatory domain is derived from an intracellular portion of the transmembrane protein CD27 (also known as S152, T14, TNFRSF7, and Tp55). In one embodiment, the co-stimulatory domain is derived from an intracellular portion of the transmembrane protein CD30 (also known as TNFRSF8, D1S166E, and Ki-1). In one embodiment, the co-stimulatory domain is derived from an intracellular portion of the transmembrane protein GITR (also known as TNFRSF18, RP5-902P8.2, AITR, CD357, and GITR-D). In one embodiment, the co-stimulatory domain derived from an intracellular portion of the transmembrane protein HVEM (also known as TNFRSF14, RP3-395M20.6, ATAR, CD270, HVEA, HVEM, LIGHTR, and TR2).

The extracellular spacer domain of the FN3 CAR is a hydrophilic region which is located between the ASTR and the transmembrane domain. In some embodiments, this domain facilitates proper protein folding for the FN3 CAR. The extracellular spacer domain is an optional component for the FN3 CAR. The extracellular spacer domain may include a domain selected from Fc fragments of antibodies, hinge regions of antibodies, CH2 regions of antibodies, CH3 regions of antibodies, artificial spacer sequences or combinations thereof. Examples of extracellular spacer domains include CD8a hinge, artificial spacers made of polypeptides which may be as small as, three glycines (Gly), as well as CH1 and CH3 domains of IgGs (such as human IgG4).

In some embodiments, an FN3 CAR molecule of the present disclosure includes an extracellular spacer domain that connects the two antigen specific targeting regions with the transmembrane domain, which, in turn, connects to the co-stimulatory domain and the intracellular signaling domain inside of the T cells. The extracellular spacer domain is preferably capable of supporting the antigen specific targeting regions to recognize and bind to the target antigen on the target cells (Hudecek et al., *Cancer Immunol. Res.* (2015) 3 (2): 125-135). In some embodiments, the extracellular spacer domain is a flexible domain, thus allowing the antigen specific targeting regions to have a structure to optimally recognize the specific structure and density of the target antigens on a cell such as tumor cell (Hudecek et al., supra). The flexibility of the extracellular spacer domain permits the extracellular spacer domain to adopt many different conformations.

In some embodiments, the extracellular spacer domain is an immunoglobulin heavy chain hinge region. In some embodiments, the extracellular spacer domain is a hinge region polypeptide derived from a receptor (e.g., a CD8-derived hinge region).

The extracellular spacer domain can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable extracellular spacer domains can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, extracellular spacer domains include glycine polymers (G)$_n$, glycine-serine polymers (including, for example, (GS)$_n$, (GSGGS)$_n$ (SEQ ID NO:1) and (GGGS)$_n$ (SEQ ID NO: 2), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2:73-142). Exemplary spacers can comprise amino acid sequences including, but not limited to, GGSG (SEQ ID NO:3), GGSGG (SEQ ID NO: 4), GSGSG (SEQ ID NO:5), GSGGG (SEQ ID NO:6), GGGSG (SEQ ID NO:7), GSSSG (SEQ ID NO:8), and the like.

In some embodiments, the extracellular spacer domain is an immunoglobulin heavy chain hinge region. Immunoglobulin hinge region amino acid sequences are known in the art; see, e.g., Tan et al., *Proc. Natl. Acad. Sci. USA* (1990) 87 (1): 162-166; and Huck et al., *Nucleic Acids Res.* (1986) 14 (4): 1779-1789. As non-limiting examples, an immunoglobulin hinge region can include one of the following amino acid sequences: DKTHT (SEQ ID NO:9); CPPC (SEQ ID NO:10); CPEPKSCDTPPPCPR (SEQ ID NO:11) (see, e.g., Glaser et al., *J. Biol. Chem.* (2005) 280:41494-41503); ELKTPLGDTTHT (SEQ ID NO:12); KSCDKTH-TCP (SEQ ID NO: 13); KCCVDCP (SEQ ID NO:14); KYGPPCP (SEQ ID NO:15); EPKSCDKTHTCPPCP (SEQ ID NO:16) (human IgG1 hinge); ERKCCVECPPCP (SEQ ID NO:17) (human IgG2 hinge); ELKTPLGDTTHTCPRCP (SEQ ID NO:18) (human IgG3 hinge); SPNMVPHAHHAQ (SEQ ID NO:19) (human IgG4 hinge); and the like.

The extracellular spacer domain can comprise an amino acid sequence of a human IgG1, IgG2, IgG3, or IgG4, hinge region. In one embodiment, the extracellular spacer domain can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:20); see, e.g., Yan et al., *J. Biol. Chem.* (2012) 287:5891-5897. In one embodiment, the extracellular spacer domain can comprise an amino acid sequence derived from human CD8, or a variant thereof.

The antigens targeted by the FN3 CAR are present on the surface or inside of cells in a tissue that targeted for removal, such as tumors, glandular (e.g. prostate) hyperplasia, and hematological malignancies. While the surface antigens are more efficiently recognized and bound by the one or more ASTRs of a subject FN3 CAR, intracellular antigens may also be targeted by the FN3 CARs. In some embodiments, the target antigens are preferably specific for cancer. Examples of target antigens include antigens expressed by various immune cells, carcinomas, sarcomas, lymphomas, leukemia, germ cell tumors, blastomas, and cells associated with various hematologic diseases.

Antigens specific for cancer which may be targeted by the one or more ASTRs of a subject FN3 CAR include one or more of 4-IBB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-IC, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

Antigens specific for inflammatory diseases which may be targeted by the one or more ASTRs of a subject FN3 CAR include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-a, IFN-γ, IgE, IgE Fc region, IL-1, IL-12, IL-23, IL-13, IL-17, IL-17A, IL-22, IL-4, IL-5, IL-5, IL-6, IL-6 receptor, integrin a4, integrin α4β7, LFA-1 (CD11a), MEDI-528, myostatin, OX-40, rhuMAb β7, scleroscin, SOST, TGF beta 1, TNF-a or VEGF-A.

Antigens specific for cancer include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

In one embodiment, the FN3 CAR may target antigens that engage cancer-treating cells, such as NK cells and other cells mentioned herein, to activate the cancer-treating cells by acting as immune effector cells. One example of this is an FN3 CAR that targets the CD16A antigen to engage NK cells to fight CD30-expressing malignancies. The bispecific, tetravalent AFM13 antibody is an example of an antibody that can deliver this effect. Further details of this type of embodiment can be found, for example, in Rothe et al., *Blood* (2015) 125 (26): 4024-4031.

In one embodiment, the FN3 CAR may target antigens such as AXL receptor tyrosine kinase (AXL), MER receptor tyrosine kinase (MER), B-cell maturation protein (BCMA; also known as TNF receptor superfamily member 17 (TNFRSF17)), programmed cell death 1 ligand 1 (PDL1; also known as CD274), programmed cell death protein 1 (PD-1; also known as CD279), the CD3 T cell co-receptor (CD3), cytotoxic T-lymphocyte-associated protein 4 (CTLA-4; also known as CD152), vascular endothelial growth factor receptor 2 (VEGFR2), frizzled class receptor 2 (FZD2), frizzled class receptor 4 (FZD4), epithelial cell adhesion molecule (EPCAM), Siglec-3 (also known as CD33), prostate-specific membrane antigen (PSMA), cluster of differentiation 28 (CD28), 4-1BB (also known as CD137, or tumor necrosis factor receptor superfamily member 9 (TNFRSF9)), Fc-gamma receptor IIIa (CD16a), the inhibitor NK cell receptor CD94/NKG2A, MHC class I chain-related protein A (MICA), MHC class I chain-related protein B (MICB), cluster of differentiation 38 (CD38; also known as cyclic ADP ribose hydrolase), and activating receptor NKp46 (also known as CD335).

In some embodiments, an FN3 CAR of the present disclosure is a multispecific FN3 CAR. The multispecific FN3 CAR comprises two or more, e.g., three or more, four or more, five or more, six or more, etc., ASTRs, each of which bind two or more, e.g., three or more, four or more, five or more, six or more, etc., target antigens. In one embodiment, the two or more target antigens are different epitopes of the same target antigen. In one embodiment, the two or more target antigens are different.

In some embodiments, a multispecific FN3 CAR of the present disclosure comprises two or more ASTRs that bind two or more target antigens, wherein the two or more target antigens are on the same cell. In one embodiment, the two or more target antigens are on at least two cells. In one embodiment, the two or more target antigens are on at least two cells, wherein each of the at least two cells are of the same cell type. In one embodiment, the two or more target antigens are on at least two cells, wherein each of the at least two cells are of a different cell type. For example, at least one of the two or more target antigens can be on a cancer cell, while another of the two or more target antigens can be on a cytotoxic cell (e.g., T cell).

In some embodiments, the two or more ASTRs can function independently, e.g., a molecule comprising two or more FN3 domain polypeptides, and no other additional components (e.g., CAR components), to bind two or more target antigens. In one embodiment, the two or more target antigens are on the same cell. In one embodiment, the two or more target antigens are on at least two cells. In one embodiment, the two or more target antigens are on at least two cells, wherein each of the at least two cells are of the same cell type. In one embodiment, the two or more target antigens are on at least two cells, wherein each of the at least two cells are of a different cell type. For example, at least one of the two or more target antigens can be on a cancer cell, while another of the two or more target antigens can be on a cytotoxic cell (e.g., T cell).

In some embodiments, the two or more ASTRs are connected by a linker. A linker of the present disclosure that may be used to connect two or more ASTRs can be of any length, e.g., 2 or more aa, 3 or more aa, 4 or more aa, 5 or more aa, 6 or more aa, 7 or more aa, 8 or more aa, 9 or more aa, 10 or more aa, 11 or more aa, 12 or more aa, 13 or more aa, 14 or more aa, 15 or more aa, 16 or more aa, 17 or more aa, 18 or more aa, 19 or more aa, 20 or more aa, 21 or more aa, 22 or more aa, 23 or more aa, 24 or more aa, 25 or more aa, etc. In one embodiment, the linker is a linker having a length of 20 amino acids (aa). In one embodiment, the linker is a linker having a length of 14 aa. In one embodiment, the linker is derived from a natural fibronectin sequence. In one embodiment, the natural fibronectin sequence is a sequence between the end of the 14$^{th}$ FN3 domain and the BC loop of the 15$^{th}$ FN3 domain of a natural fibronectin, e.g., human fibronectin. In one embodiment, the linker comprises the sequence AIDAPSNLRFLATTPNSLLV (SEQ ID NO:21). In one embodiment, the linker is a linker having a length of 20 aa derived from a sequence between the end of the 14$^{th}$ FN3 domain and the BC loop of the 15$^{th}$ FN3 domain, e.g., a linker having the sequence AIDAPSNLRFLATTPNSLLV (SEQ ID NO:21). In one embodiment, the linker comprises the sequence AIDAPSNLRFLATT (SEQ ID NO:22). In one embodiment, the linker is a linker having a length of 14 aa derived from a sequence between the end of the 14$^{th}$ FN3 domain and the BC loop of the 15$^{th}$ FN3 domain, e.g., a linker having the sequence AIDAPSNLRFLATT (SEQ ID NO:22). An exemplary sequence that is between the 14$^{th}$ FN3 domain and 15$^{th}$ FN3 domain of a natural fibronectin is shown below: NVSPPRRARVTDATETTITISWRTK-TETITGFQVDAVPANGQTPIQRTIKPDVRSYTITGL QPGTDYKIYLYTLNDNARSSPVVIDASTAIDAPSNLR-FLATTPNSLLVSWQPPRARITGYII KYEKPGSPPRE-VVPRPRPGVTEATITGLEPGTEYTIYVI-ALKNNQKSEPLIGRKKT (SEQ ID NO: 23)

Additional examples of target antigens include, without limitation, AGR2, AIG1, AKAP1, AKAP2, ANGPT1, ANGPT2, ANGPTL3, ANGPTL4, ANPEP, APC, APOC1, AR, AZGP1 (zinc-α-glycoprotein), BAD, BAG1, BAI1, BCL2, BMP6, BPAG1, BRC1A, BRCA1, CANT1, CAV1, CCL11, CCL2, CCNA1, CCNA2, CCND1, CCNE1, CCNE2, CD138, CD164, CD19, CD20, CD22, CD3, CD4, CD44, CD52, CD8, CDH1 (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21$^{Wap1/Cip1}$), CDKN1B (p27$^{Kip1}$), CDKN1C, CDKN2A (p16$^{INK4A}$), CDKN2B, CDKN2C, CDKN3, CEA, CHGA, CHGB, CLDN3, CLDN7 (claudin-7), CLN3, CLU (clusterin), COL18A1, COL1A1, COL4A3, COL6A1, CTNNB1 (β-catenin), CTSB (cathepsin), CXCL1, CXCL10, CXCL3, CXCL5, CXCL6, CXCL9, CYB5, CYC1, DAP2IP, DES, DNCL1, E2F1, ECGF1, EDG1, EFNA1, EFNA3, EFNB2, EGF, EGFR, EGFRvIII, ELAC2, ENG, ENO1, ENO2, ENO3, EPHB4, ERBB2 (Her-2), EREG, ERK8, ESR1, ESR2, F3 (TF), FAP, FASN, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR3, FIGF, FLJ12584, FLJ25530, FLRT1 (fibronectin), FLT1, FOSL1 (FRA-1), GABRP (GABA-A), GAGEB1, GAGEC1, GATA3, GD2, GGT1, GNAS1, GNRH1, GPC3, GRP, GSN (Gelsolin), GSTP1, HGF, HGFR (MET), HIP1, HUMCYT2A, ID2, IFNA1, IFNB1, IFNG, IGF1, IGF1R, IGF2, IGFBP2, IGFBP3, IGFBP6, Igκ light chain, IL12A, IL13RA2, ILIA, IL1B, IL2, IL24, IL29, IL2RA, IL3RA (CD123), IL6, IL6R, IL6ST (glycoprotein 130), IL8, ILK, INHA, INSL3, INSL4, ITGA1, ITGA6 (a6 integrin), ITGAV, ITGB3, ITGB4 (β4 integrin), JAG1, JUN, K6HF, KAII, KDR, KLF5 (GC Box BP), KLK10, KLK12, KLK13, KLK14, KLK15, KLK3, KLK4, KLK5, KLK6, KLK9, KRT1, KRT19, KRT2A, KRTHB6 (hair-specific type II keratin), LAMA5, Lewis-Y, MACMARCKS, MAP2K7 (c-Jun), MDK, MIB1, MKI67 (Ki-67), MMP2, MMP9, MSLN (mesothelin), MSMB, MT3 (metallothionein-3), MTSS1, MUC1 (mucin), MUC16, MYC, NGFB (NGF), NGFR, a NKG2D ligand, NME1 (NM23A), NOX5, NR0B1, NR0B2, NR1D1, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NTN4, ODZ1, P1AS2, P1K3CG, PAP, PART1, PATE, PAWR, PCA3, PCNA, PDGFA, PECAM1, PF4, PGF, PGR, PLAU (UPA), Plectin, PLG, PLXDC1, PPID, PR1, PRKCQ, PRKD1, PRL, PROK2, PSAP, PSCA, PSMA, PTEN, PTGS2 (COX-2), RAC2 (p21-Rac2), RARB, ROBO2, ROR-1, S100A2, SCGB1D2 (lipophilin B), SCGB2A1 (mammaglobin-2), SCGB2A2 (mammaglobin-1), SER-PINA3, SERPINB5 (maspin), SERPINE1 (PAI-1), SER-PINF1, SHBG, SHBQ, SLC2A2, SLC33A1, SLC43A1, SPRR1B (Spr1), STAB1, STEAP, STEAP2, TEK, TGFA, TGFB1, TGFB111, TGFB111, TGFB2, TGFB3, TGFBR1, TGRA, THBS1 (thrombospondin-1), THBS2, THBS4, TIE (Tie-1), TIMP3, TNF, TNFAIP2 (B94), TNFRSF6 (Fas), TNFRSF7 (BCMA), TNFRSF8 (CD30), TNFSF10, TNFSF6 (FasL), TOP2A (topoisomerase-2α), TP53, TPM1, TPM2, TRPC6, VEGF, and VEGFC.

Conditionally Active Chimeric Antigen Receptors

The present invention provides a conditionally active FN3 CAR for binding with a target antigen, comprising at least one antigen specific targeting region comprising an FN3 domain polypeptide, wherein the at least one antigen specific targeting region is evolved from a wild-type protein or a domain thereof and having at least one of: (a) a decrease in activity in the assay at the normal physiological condition compared to the antigen specific targeting region of the wild-type protein or a domain thereof, and (b) an increase in activity in the assay under the aberrant condition compared to the antigen specific targeting region of the wild-type protein or a domain thereof. In some embodiments, a chimeric antigen receptor of the present invention further comprises a transmembrane domain (TM), and an intracellular signaling domain (ISD). In some embodiments, the FN3 CAR may further include an extracellular spacer domain (ESD) and/or a co-stimulatory domain (CSD). Non-ASTR components of an FN3 CAR of the present invention are described herein.

The conditionally active FN3 CARs of the present invention have at least one of (1) their affinity to the target antigen reversibly or irreversibly reduced at the normal physiological condition, and (2) an increased affinity, in comparison with the same FN3 CAR without the conditionally active antigen specific targeting region. These conditionally active FN3 CARs can, e.g., direct cytotoxic cells to a disease site where an aberrant condition is present, such as a tumor microenvironment or synovial fluid. As a result of these properties, the conditionally active FN3 CARs can preferentially direct the cytotoxic cells to a disease site while because of their low affinity for normal tissue. Such conditionally active FN3 CARs can dramatically reduce side-effects and allow higher doses of therapeutics to be used to increase therapeutic efficacy. The conditionally active FN3 CARs of the present disclosure are particularly valuable for development of novel therapeutics that are required for short or limited periods of time within a subject. Examples of beneficial applications include systemic treatments at high dosages, as well as localized treatments at high concentrations.

In one embodiment, the conditionally active chimeric antigen receptor may include an antigen specific targeting region that has a decrease in a binding affinity to the target antigen at a normal physiological condition compared to the antigen specific targeting region of the wild-type protein or the domain thereof.

In one embodiment, the conditionally active chimeric antigen receptor may include an antigen specific targeting region that has an increase in activity in the assay under the aberrant condition compared to the antigen specific targeting region of the wild-type protein or a domain thereof and a decrease in a binding affinity to the target antigen at a normal physiological condition compared to the antigen specific targeting region of the wild-type protein or the domain thereof.

In some embodiments, the conditionally active chimeric antigen receptor may comprise an antigen specific targeting region that has an increase in selectivity in the assay under the aberrant condition compared to the antigen specific targeting region of the wild-type protein or a domain thereof.

In some embodiments, a conditionally active FN3 CAR of the present disclosure includes a linker to connect the one or more antigen specific targeting regions. The linker orients the two antigen specific targeting regions in such a way that the two antigen specific targeting regions on the FN3 CAR exhibit improved or optimal activity in binding to the target antigen (Jensen and Riddell, *Immunol. Rev.* (2014) 257 (1): 127-144). The linker is thus capable of adopting a specific conformation which enables improved or optimal binding of the two antigen specific targeting regions to the target antigen, thereby increasing the effectiveness of FN3 CAR-T cells.

In some embodiments, the linker may be Gly-Ser tandem repeats in a length of 18-25 amino acids (Grada et al., *Mol. Ther. Nucleic Acids* (2013) 2: e105). This flexible linker is capable of adopting many different conformations for improved or optimal presentation of two antigen specific targeting regions for binding to the target antigen.

In some embodiments, the linker is capable of adopting different conformations at a normal physiological condition and an aberrant condition. Particularly, the linker has a first conformation at the aberrant condition which is improved or optimal for presentation of two antigen specific targeting regions for binding to the target antigen, while the same linker has a second conformation at the normal physiological condition which is less effective for presentation of two antigen specific targeting regions for binding to the target antigen than the first conformation of the linker under the aberrant condition. Such a linker may be called a "conditional linker" that allows the two antigen specific targeting regions to bind to the target antigen at a higher binding activity at an aberrant condition than at a normal physiological condition. Therefore, FN3 CAR-T cells including such a conditional linker are more active at an aberrant condition than the same FN3 CAR-T cells at a normal physiological condition.

Proteins that change conformation at different pH are known in the art, for example, see, Di Russo et al., *PLoS Comput. Biol.* (2012) 8 (11): e1002761. Proteins with different conformations at different temperatures are known in the art, see, e.g., Caldwell, *Plant Physiol.* (1987) 84 (3): 924-929. The conformation of antibodies being influenced by pH and/or temperature has been discussed in, e.g., Gandhi, University of Rhode Island Master's Thesis, U.S. (2002).

In some embodiments, a conditional linker is selected to be used in a conditionally active CAR molecule of the present disclosure. The conditional linker can adopt a first conformation at an aberrant condition, which is improved or optimal for presenting the one or more antigen specific targeting regions for binding to the target antigen, and adopt a second conformation at a normal physiological condition, which is suboptimal for presenting the one or more antigen specific targeting regions for binding to the target antigen. In some embodiments, the suboptimal conformation of the linker at the normal physiological condition produces a conditionally active FN3 CAR molecule having a binding activity to the target antigen that is less than about 90%, or about 80%, or about 70%, or about 60%, or about 50%, or about 40%, or about 30%, or about 20%, or about 10%, or about 5% of the binding activity of the conditionally active FN3 CAR molecule with the improved or optimal conformation of the linker at the aberrant condition.

The conditional linker may be generated from a starting linker selected from 2A linkers, 2A-like linkers, picornaviral 2A-like linkers, a 2A peptide of porcine teschovirus (P2A), and a 2A peptide of thosea asigna virus (T2A), as well as variants and functional equivalents thereof. The starting linker is evolved to produce mutant proteins; the mutant proteins are then subjected to an assay at a normal physiological condition and an assay at an aberrant condition.

Proteins having a conditional linker are selected from the mutant proteins on the basis that the selected proteins exhibit (a) a conditional linker having a first conformation at the aberrant condition, which is improved or optimal for presenting the two antigen specific targeting regions for binding to the target antigen, and (b) a second conformation of the conditional linker at the normal physiological condition, which is suboptimal for presenting the two antigen specific targeting regions for binding to the target antigen.

In some embodiments, the extracellular spacer domain is capable of adopting different conformations at a normal physiological condition and an aberrant condition. Particularly, the extracellular spacer domain has a first conformation at the aberrant condition which is improved or optimal for presentation of the one or more antigen specific targeting regions for binding to the target antigen, while the same extracellular spacer domain has a second conformation at the normal physiological condition which is suboptimal for presentation of the one or more antigen specific targeting regions for binding to the target antigen. Such an extracellular spacer domain may be called a "conditional extracellular spacer domain" since it enables the one or more antigen specific targeting regions to bind to the target antigen at a higher binding activity at the aberrant condition than at the normal physiological condition. Therefore, with the conditional extracellular spacer domain, FN3 CAR-T cells may be more active at the aberrant condition than the same FN3 CAR-T cells at the normal physiological condition.

In some embodiments, a conditional extracellular spacer domain is selected to be used in the conditionally active FN3 CAR molecule of the present disclosure. In some embodiments, the suboptimal conformation of the extracellular spacer domain at the normal physiological condition produces a conditionally active FN3 CAR molecule having a binding activity to the target antigen that is less than about 90%, or about 80%, or about 70%, or about 60%, or about 50%, or about 40%, or about 30%, or about 20%, or about 10%, or about 5% of the FN3 CAR molecule with the optimal conformation for the same extracellular spacer domain at the aberrant condition.

It has been discovered that the ubiquitylation-resistant form for the region including the extracellular spacer domain and the transmembrane domain can enhance FN3 CAR-T cell signaling and thus augment antitumor activity (see, e.g., Kunii et al., *Hum. Gene Ther.* (2013) 24 (1): 27-37). Within this region, the extracellular spacer domain is outside of the FN3 CAR-T cells, and thus is exposed to different conditions and can potentially be made conditionally ubiquitylation-resistant. In some embodiments, the extracellular spacer domain is conditionally ubiquitylation-resistant. In one embodiment, the extracellular spacer domain of the conditionally active FN3 CAR molecule of the present disclosure is more ubiquitylation-resistant at an aberrant condition than at a normal physiological condition. Therefore, the FN3 CAR-T cells having the conditionally ubiquitylation-resistant extracellular spacer domain will have enhanced cytotoxicity at the aberrant condition, relative to their cytotoxicity at the normal physiological condition.

The conditionally ubiquitylation-resistant extracellular spacer domain may be selected to be more ubiquitylation-resistant at an aberrant pH or aberrant temperature, and less ubiquitylation-resistant at a normal physiological pH or normal physiological temperature. In one embodiment, the conditionally ubiquitylation-resistant extracellular spacer domain is more ubiquitylation-resistant at a pH of a tumor microenvironment, and less ubiquitylation-resistant at a normal physiological pH, such as the pH in human blood plasma at pH 7.2-7.6.

To produce a conditional extracellular spacer domain, a starting protein fragment selected from an Fc fragment of an antibody, a hinge region of an antibody, a CH2 region of an antibody, and a CH3 region of an antibody, is evolved to produce mutant proteins. The mutant proteins are subjected to an assay at a normal physiological condition and an assay at an aberrant condition. The conditional extracellular spacer domain is selected from the mutant proteins that exhibit (a) a conditional extracellular spacer domain that has a first conformation at the aberrant condition for the antigen specific targeting region to bind to the target antigen at a higher binding activity and a second conformation of the conditional extracellular binding domain at the normal physiological condition for the antigen specific targeting region to bind to the target antigen at a lower binding activity than at the aberrant condition, or proteins that are (b) more ubiquitylation-resistant at the aberrant condition than at the normal physiological condition. See, e.g., PCT Publication No. WO2017034615A1, incorporated herein by reference in its entirety.

In addition, a chimeric antigen receptor of the present disclosure may be configured such that a protein containing the antigen receptor has an increase in expression level compared to the wild-type protein or a domain thereof.

In one embodiment, the present invention provides a chimeric antigen receptor for binding with a target antigen, including at least one antigen specific targeting region evolved from a wild-type protein or a domain thereof and having an increase in selectivity in the assay under the aberrant condition compared to the antigen specific targeting region of the wild-type protein or a domain thereof; a transmembrane domain; and an intracellular signaling domain. In some embodiments, the chimeric antigen receptor further includes an extracellular spacer domain or at least one co-stimulatory domain.

The present disclosure is also directed to methods of evolving a wild-type protein or a domain thereof (e.g., a fibronectin type 3 domain polypeptide) to generate a conditionally active protein that has at least one of: (a) a decrease in activity in the assay at the normal physiological condition compared to the antigen specific targeting region of the wild-type protein or a domain thereof, and (b) an increase in activity in the assay under the aberrant condition compared to the antigen specific targeting region of the wild-type protein or a domain thereof. The conditionally active protein (e.g., conditionally active fibronectin type 3 domain polypeptide) may be engineered into a CAR.

The chimeric antigen receptor produced by the method may include at least one antigen specific targeting region that has a decrease in a binding affinity to the target antigen at a normal physiological condition compared to the antigen specific targeting region of the wild-type protein or the domain thereof.

The chimeric antigen receptor produced by the method may include an antigen specific targeting region that has an increase in activity in the assay under the aberrant condition compared to the antigen specific targeting region of the wild-type protein or a domain thereof and a decrease in a binding affinity to the target antigen at a normal physiological condition compared to the antigen specific targeting region of the wild-type protein or the domain thereof.

In any of the chimeric antigen receptors produced by the method, the antigen specific targeting region may also have an increase in selectivity in the assay under the aberrant condition compared to the antigen specific targeting region of the wild-type protein or a domain thereof.

In any of the chimeric antigen receptors produced by the method, the FN3 CAR may be configured such that a protein containing the antigen receptor has an increase in expression level compared to the wild-type protein or a domain thereof.

In one embodiment, the chimeric antigen receptor produced by the method, for binding with a target antigen, includes at least one antigen specific targeting region evolved from a wild-type protein or a domain thereof and having an increase in selectivity in the assay under the aberrant condition compared to the antigen specific targeting region of the wild-type protein or a domain thereof; a transmembrane domain; and an intracellular signaling domain. In some embodiments, the chimeric antigen receptor further includes an extracellular spacer domain or at least one co-stimulatory domain.

Modifications

An FN3 CAR of the present disclosure can be synthesized with modified linkers such that additional functional moieties may be attached to the FN3 CAR. Modified linkers allow for attachment of, e.g., any sulfhydryl-reactive moiety. In one embodiment, N-succinimidyl-S-acetylthioacetate (SATA) is attached to bis-maleimide to form bis-maleimido-acetylthioacetate (BMata). After deprotection of the masked thiol group, any functional group having a sulfhydryl-reactive (or thiol-reactive) moiety may be attached to the FN3 CARs.

Exemplary thiol-reactive reagents include a multifunctional linker reagent, a capture, i.e. an affinity label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). Such FN3 CARs having modified linkers may be further reacted with a drug moiety reagent or other label. Reaction of an FN3 CAR with a drug-linker intermediate may provide a FN3 CAR-drug conjugate.

An FN3 CAR of the present disclosure can further include one or more additional polypeptide domains, where such domains include, but are not limited to, a signal sequence; an epitope tag; an affinity domain; and a polypeptide that produces a detectable signal.

In some embodiments, a subject FN3 CAR may include a signal sequence. Signal sequences that are suitable for use in a subject FN3 CAR include any eukaryotic signal sequence, including a naturally-occurring signal sequence, a synthetic (e.g., man-made) signal sequence, etc.

In some embodiments, a subject FN3 CAR may include an epitope tag. Suitable epitope tags include, but are not limited to, hemagglutinin (HA; e.g., YPYDVPDYA (SEQ ID NO: 24); FLAG (e.g., DYKDDDDK (SEQ ID NO:25); c-myc (e.g., EQKLISEEDL; SEQ ID NO: 26), and the like.

In some embodiments, a subject FN3 CAR may include an affinity domain. Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:27), HisX6 (HHHHHH) (SEQ ID NO:28), C-myc (EQKLISEEDL) (SEQ ID NO:26), Flag (DYKDDDDK) (SEQ ID NO:25), StrepTag (WSHPQFEK) (SEQ ID NO: 29), hemagluttinin, e.g., HA Tag (YPYDVPDYA) (SEQ ID NO:24), GST, thioredoxin, cellulose binding domain, RYIRS (SEQ ID NO:30), Phe-His-His-Thr (SEQ ID NO:31), chitin binding domain, S-peptide, T7 peptide, SH2 domain, C-end RNA tag, WEAAAREACCRECCARA (SEQ ID NO:32), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein, and the like.

In some embodiments, a subject FN3 CAR may include a detectable signal-producing polypeptide. Suitable detectable signal-producing proteins include, e.g., fluorescent proteins; enzymes that catalyze a reaction that generates a detectable signal as a product; and the like. Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2 (12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, m Tangerine, mStrawberry, mCherry, mGrape1, mRaspberry, mGrape2, mPlum (Shaner et al., *Nature Methods* (2005) 2:905-909), and the like. Any of a variety of fluorescent and colored proteins from Anthozoan species, as described in, e.g., Matz et al., *Nature Biotechnol.* (1999) 17:969-973. Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Nucleic Acids

The present disclosure provides a nucleic acid encoding a chimeric antigen receptor for binding with a target antigen, comprising at least one antigen specific targeting region comprising a fibronectin type 3 domain polypeptide.

In some embodiments, a subject nucleic acid provides for production of an FN3 CAR of the present disclosure, e.g., in a mammalian cell. In some embodiments, a subject nucleic acid provides for amplification of the FN3 CAR-encoding nucleic acid.

In some embodiments, a subject nucleic acid encoding an FN3 CAR of the present disclosure can be operably linked to a transcriptional control element, e.g., a promoter, and enhancer, etc. Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *Proc. Natl. Acad. Sci. USA* (2000) 28: e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. *Annual Review of Biochemistry* (2006) 567-605; and Tropp, *Molecular Biology* (2012) (Jones & Bartlett Publishers, Sudbury, Mass.), the disclosures of which are incorporated herein by reference.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. *Proc. Natl. Acad. Sci. USA* (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. *Blood* (2011) 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.* (1991) 173 (1): 86-93; Alpuche-Aranda et al., *Proc. Natl. Acad. Sci. USA* (1992) 89 (21): 10079-83), a nirB promoter (Harborne et al. *Mol. Micro.* (1992) 6:2805-2813), and the like (see, e.g., Dunstan et al., *Infect. Immun.* (1999) 67:5133-5141; McKelvie et al., *Vaccine* (2004) 22:3243-3255; and Chatfield et al., *Biotechnol.* (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al., *Infect. Immun.* (2002) 70:1087-1096); an rpsM promoter (see, e.g., Valdivia and Falkow *Mol. Microbiol.* (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., *Nucl. Acids Res.* (1984) 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., *Proc. Natl. Acad. Sci. U.S.A.* (1983) 80:21-25).

In some embodiments, a polynucleotide sequence encoding a subject FN3 CAR further comprises a polynucleotide sequence encoding an FN3 CAR inducible expression cassette. In one embodiment, the FN3 CAR inducible expression cassette is for the production of a transgenic polypeptide product that is released upon CAR signaling. See, e.g., Chmielewski and Abken, *Expert Opin. Biol. Ther.* (2015) 15 (8): 1145-1154; and Abken, *Immunotherapy* (2015) 7 (5): 535-544. In some embodiments, a polynucleotide sequence encoding a subject FN3 CAR further comprises a polynucleotide sequence encoding a cytokine operably linked to a T-cell activation responsive promoter. In some embodiments, the cytokine operably linked to a T-cell activation responsive promoter is present on a separate polynucleotide sequence. In one embodiment, the cytokine is IL-12.

A nucleotide sequence encoding a subject FN3 CAR can be present in an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., *Invest. Opthalmol. Vis. Sci.* (1994) 35:2543-2549; Borras et al., *Gene Ther.* (1999) 6:515-524; Li and Davidson, *Proc. Natl. Acad. Sci. USA* (1995) 92:7700-7704; Sakamoto et al., *H. Gene Ther.* (1999) 5:1088-1097; WO 94/12649, WO 93/03769; WO 93/19191; WO 94/28938; WO 95/11984 and WO 95/00655); adeno-associated virus (see, e.g., Ali et al., *Hum. Gene Ther.* (1998) 9:81-86, Flannery et al., *Proc. Natl. Acad. Sci. USA* (1997) 94:6916-6921; Bennett et al., *Invest. Opthalmol. Vis. Sci.* (1997) 38:2857-2863; Jomary et al., *Gene Ther.* (1997) 4:683 690, Rolling et al., *Hum. Gene Ther.* (1999) 10:641-648; Ali et al., *Hum. Mol. Genet.* (1996) 5:591-594; Srivastava in WO 93/09239, Samulski et al., *J. Vir.* (1989) 63:3822-3828; Mendelson et al., *Virol.* (1988) 166:154-165; and Flotte et al., *Proc. Natl. Acad. Sci. USA* (1993) 90:10613-10617); SV40; herpes simplex virus; human immunodeficiency virus (see, e.g., Miyoshi et al., *Proc. Natl. Acad. Sci. USA* (1997) 94:10319-23; Takahashi et al., *J. Virol.* (1999) 73:7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like.

In some embodiments, a nucleic acid encoding a subject FN3 CAR of the present disclosure will in some embodiments be RNA, e.g., in vitro synthesized RNA. Methods for in vitro synthesis of RNA are known in the art; any known method can be used to synthesize RNA comprising a sequence encoding an FN3 CAR of the present disclosure. Methods for introducing RNA into a host cell are known in the art. See, e.g., Zhao et al. *Cancer Res.* (2010) 15:9053. Introducing RNA comprising a nucleotide sequence encoding an FN3 CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding an FN3 CAR of the present disclosure.

Engineering Cells

A chimeric antigen receptor of the present disclosure may be assembled by ligating the polynucleotide sequences encoding the individual domains to form a single polynucleotide sequence (the FN3 CAR gene, which encodes the FN3 CAR of the present disclosure). The individual domains include at least one ASTR comprising a fibronectin type 3 domain polypeptide, a TM, and an ISD. In some embodiments, other domains may also be introduced in the FN3 CARS, including an ESD and a CSD. If the FN3 CAR is a multispecific CAR, the FN3 CAR gene may be, for example, in the following configuration in the N-terminal to C-terminal direction: N-terminal signal sequence-ASTR 1-linker-ASTR 2-extracellular spacer domain-transmembrane domain-co-stimulatory domain-intracellular signaling domain. In one embodiment, such an FN3 CAR gene may include two or more co-stimulatory domains.

In some embodiments, the polynucleotide sequence encoding the FN3 CAR may be in the following configuration in the N-terminal to C-terminal direction: N-terminal signal sequence-ASTR 1-linker-ASTR 2-transmembrane domain-co-stimulatory domain-intracellular signaling domain. In one embodiment, such a FN3 CAR may include two or more co-stimulatory domains. If an FN3 CAR includes more than two ASTRs, the polynucleotide sequence encoding the FN3 CAR may be in the following configuration in the N-terminal to C-terminal direction: N-terminal signal sequence-ASTR 1-linker-ASTR 2-linker-(antigen-specific targeting region)$_n$-transmembrane domain-co-stimulatory domain-intracellular signaling domain, where n is an integer of at least one. Such an FN3 CAR may further include an extracellular spacer domain. Each ASTR may be separated by a linker. In an embodiment, such an FN3 CAR may include two or more co-stimulatory domains.

In some embodiments, the conditionally active FN3 CAR is introduced into a cell (e.g., a cytotoxic cell) by an expression vector. Expression vectors including a polynucleotide sequence encoding a conditionally active FN3 CAR of the invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HS V) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the FN3 CAR gene in the host cell. In some embodiments, the adenovirus genome is a 36 kb, linear, double stranded DNA, where a foreign DNA sequence (such as FN3 CAR genes) may be inserted to substitute large pieces of adenoviral DNA in order to make the expression vector of the present invention (see, e.g., Danthinne and Imperiale, *Gene Therapy* (2000) 7 (20): 1707-1714).

Another expression vector is based on an adeno associated virus, which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., one encoding the FN3 CAR) into the viral genome at certain locations to produce a virus that is replication defective. Though the retrovirus vectors are able to infect a broad variety of cell types, integration and stable expression of the FN3 CAR gene requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression of the FN3 CAR gene (see, e.g., U.S. Pat. No. 5,994,136).

Expression vectors including the conditionally active FN3 CAR gene can be introduced into a host cell by any means known to person skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is a T cell, NK cell or NKT cell.

The present invention also provides genetically engineered cells (e.g., cytotoxic cells) which include and stably express a chimeric antigen receptor of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Non-limiting examples of suitable T cells include CD4$^+$/CD8", CD47CD8$^+$, CD47CD8" or CD4$^+$/CD8$^+$ T cells. The T cells may be a mixed population, e.g., of CD4$^+$/CD8" and CD47CD8$^{-1}$" cells or a population of a single clone. CD4$^+$ T cells of the invention may also produce IL-2, IFN-gamma, TNF-alpha and other T cell effector cytokines when co-cultured in vitro with cells expressing the target antigens (for example CD20$^+$ and/or CD 19$^+$ tumor cells). CD8$^+$ T cells of the invention may lyse cells expressing the target antigen. In some embodiments, T cells may be any one or more of CD45RA$^+$ CD62L$^+$ naive cells, CD45RO CD6217 central memory cells, CD62L effector memory cells or a combination thereof (Berger et al., *Curr. Opin. Immunol.* (2009) 21 (2): 224-232).

Genetically engineered cytotoxic cells may be produced by stably transfecting host cells with an expression vector including the FN3 CAR gene of the invention. Additional methods to genetically engineer the cytotoxic cells using the expression vector include chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells demonstrating the presence of a single integrated un-rearranged vector and expressing an FN3 CAR may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), *Molecular Cloning: A Laboratory Manual*, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

In some embodiments, the expression vector comprising a polynucleotide sequence encoding a subject FN3 CAR further comprises a polynucleotide sequence encoding a CAR inducible expression cassette for a transgenic polypeptide product that is produced and released upon CAR signaling. In some embodiments, the expression vector comprising a polynucleotide sequence encoding a subject FN3 CAR further comprises a polynucleotide sequence encoding a cytokine operably linked to a T-cell activation responsive promoter. In some embodiments, an expression vector comprising a nucleic acid sequence encoding a cytokine operably linked to a T-cell activation responsive promoter is further introduced into an engineered cytotoxic cell (e.g., comprising a subject FN3 CAR molecule) of the present disclosure. In one embodiment, the cytokine is IL-12. In such embodiments, the engineered T-cell expressing an FN3 CAR of the present disclosure is capable of inducible or constitutive release of the cytokine (e.g., IL-12). In one embodiment, the T-cell activation responsive promoter is a nuclear factor of the activated T cell (NFAT) responsive promoter. In an engineered T-cell expressing an FN3 CAR of the present disclosure capable of inducible or constitutive release of IL-12, IL-12 may accumulate in, e.g., a tumor lesion where it promotes tumor destruction by at least: (a) induction of an innate immune cell response towards cancer cells which are invisible to redirected T-cells, and (b) triggering programmatic changes in immune-suppressive cells. This provides an additional layer of strategy involving the use of FN3 CAR engineered T-cells. See, e.g., Chmielewski and Abken, *Expert Opin. Biol. Ther.* (2015) 15 (8): 1145-1154; and Abken, *Immunotherapy* (2015) 7 (5): 535-544.

After the expression vector containing the FN3 CAR gene is introduced into the host cell, the FN3 CAR gene will be expressed thus producing an FN3 CAR molecule that can bind to the target antigen. The produced FN3 CAR molecule becomes a transmembrane protein at least by virtue of having a transmembrane domain. The host cells will then be converted to FN3 CAR cells such as FN3 CAR-T cells. The process for producing engineered cytotoxic cells with the FN3 CAR molecule, for example FN3 CAR-T cells, has been described in, for example, (Cartellieri et al., *J. Biomed. Biotechnol.* (2010) Article ID: 956304; and Ma et al., *Proc. Natl. Acad. Sci. USA* (2016) 113 (4): E450-458).

Whether prior to or after genetic modification of the cytotoxic cells to express a desirable FN3 CAR, the cells can be activated and expanded in number using methods as described, for example, in U.S. Pat. Nos. 6,352,694; 6,534, 055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) and these can be used in the invention, as can other methods known in the art (see, e.g., ten Berge et al., *Transplant Proc.* (1998) 30 (8): 3975-3977; Haanen et al., *J. Exp. Med.* (1999) 190 (9): 1319-1328; and Garland et al., *J. Immunol. Methods* (1999) 227 (1-2): 53-63).

Compositions

The present invention provides pharmaceutical compositions including a pharmaceutically acceptable excipient and a therapeutically effective amount of an FN3 CAR of the invention. The FN3 CAR in the composition may be any one or more of a polynucleotide encoding the FN3 CAR, a protein including the FN3 CAR or genetically modified cells expressing the FN3 CAR protein.

The pharmaceutically acceptable excipient may include any excipient that is useful in preparing a pharmaceutical composition that is generally safe, non-toxic, and desirable, and includes excipients that are acceptable for veterinary use as well as for human pharmaceutical use. One type of excipient includes pharmaceutically acceptable carriers, which may be added to enhance or stabilize the composition, or to facilitate preparation of the composition.

The pharmaceutically acceptable carriers are determined in part by the particular composition being administered, as well as by the particular method used to administer the composition. Accordingly, there are a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjustment agents and buffering agents, toxicity adjusting agents and the like, for example, sodium acetate, sodium chloride, potassium chloride, calcium chloride, sodium lactate and the like. The concentration of FN3 CAR in these formulations can vary widely, and will be selected primarily based on fluid volumes, viscosities, and body weight in accordance with the particular mode of administration selected and the patient's needs.

The pharmaceutical composition may be formulated for parenteral administration, such as, for example, by intra-articular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives, in the practice of this invention, compositions can be administered, for example, by intravenous infusion, orally, topically, intraperitoneally, intravesically or intrathecally. In one embodiment, parenteral modes of administration are preferred methods of administration for compositions including the FN3 CAR protein or genetically engineered cytotoxic cells. The compositions may conveniently be administered in unit dosage form and may be prepared by any of the methods well-known in the pharmaceutical art, for example as described in Remington's Pharmaceutical Sciences, Mack Publishing Co. Easton Pa., $18^{th}$ Ed., 1990. Formulations for intravenous administration may contain a pharmaceutically acceptable carrier such as sterile water or saline, polyalkylene glycols such as polyethylene glycol, oils of vegetable origin, hydrogenated naphthalenes and the like.

The pharmaceutical composition may be administered by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further include administering, prior to, concurrently, or after the subject CAR at least one composition including an effective amount of at least one compound or protein selected from at least one of a detectable label or reporter, a TNF antagonist, an antirheumatic, a muscle relaxant, a narcotic, a non-steroid anti-inflammatory drug (NSAK)), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, or an antiproliferative agent.

Methods of Treatment

An FN3 CAR of the present disclosure, when present in a T lymphocyte or an NK cell, can mediate cytotoxicity toward a target cell. An FN3 CAR of the present disclosure binds to an antigen present on a target cell, thereby mediating killing of a target cell by a T lymphocyte or an NK cell genetically modified to produce the FN3 CAR. The antigen-binding domain of the FN3 CAR binds to an antigen present on the surface of a target cell. Target cells include, but are not limited to, cancer cells, e.g., hematological cancer cells, solid tumor cells, etc. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject FN3 CAR, such that the T lymphocyte or NK cell recognizes an antigen present on the surface of a target cancer cell, and mediates killing of the target cell.

The present disclosure provides a method of treating cancer in a subject having a cancer, the method comprising: i) introducing a chimeric antigen receptor of the present disclosure, or introducing an expression vector of the present disclosure, into a cell, to produce an engineered cell; and ii) administering the engineered cell to the subject. In some embodiments, the cell is obtained from the subject, engineered ex vivo, and administered to the same subject. In some embodiments, the cell is obtained from one subject, engineered ex vivo, and administered to a second suitable subject.

In some embodiments, the present invention provides a method including retrieving cytotoxic cells from a subject, genetically engineering the cytotoxic cells by introducing an FN3 CAR gene of the present invention into the cytotoxic cells, and administering the genetically engineered cytotoxic cells to the subject. In some embodiments, the cytotoxic cells are selected from T cells, naive T cells, memory T cells, effector T cells, natural killer cells, and macrophages. In one embodiment, the cytotoxic cells are T cells.

In one embodiment, the T cells are obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art, may be used. In some embodiments of the present invention, T cells can be obtained from blood collected from a subject using any number of techniques known to the skilled artisan, such as Ficoll™ separation.

In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In one embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or another saline solution with or without buffer. In some embodiments, the undesirable components of the apheresis sample may be removed and the cells directly resuspended in culture media.

In one embodiment, T cells are isolated from peripheral blood by lysing the red blood cells and depleting the monocytes, for example, by centrifugation through a PERCOLL™ gradient or by counter-flow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. To enrich $CD4^+$ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, $CD62L^{hi}$, $GITR^+$, and $FoxP3^+$.

For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In one embodiment, the time period ranges from 30 minutes to 36 hours or longer and all integer values there between. In one embodiment, the time period is at least 1, 2, 3, 4, 5, or 6 hours. In one embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled person would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

The obtained cells are then genetically engineered as described herein. A polynucleotide encoding the FN3 CAR, typically located in an expression vector, is introduced into the cytotoxic cells such that the cytotoxic cells will express, preferably stably, the FN3 CAR. The polynucleotide encoding the FN3 CAR is typically integrated into the cytotoxic cell host genome. In some embodiments, the polynucleotide encoding the FN3 CAR also encodes an FN3 CAR inducible expression cassette for a transgenic polypeptide product that is produced and released upon CAR signaling. In some embodiments, the polynucleotide encoding the FN3 CAR also encodes a cytokine (e.g., IL-12) operably linked to a T-cell activation responsive promoter. In some embodiments, the expression vector comprises both the polynucleotide encoding the FN3 CAR and the polynucleotide encoding the cytokine operably linked to the T-cell activation responsive promoter. See, e.g., Chmielewski and Abken, *Expert Opin. Biol. Ther.* (2015) 15 (8): 1145-1154; and Abken, *Immunotherapy* (2015) 7 (5): 535-544. In some embodiments the cells are genetically engineered with an expression vector comprising the polynucleotide encoding the FN3 CAR and an expression vector comprising the polynucleotide encoding the cytokine (e.g., IL-12) operably linked to the T-cell activation responsive promoter. In some embodiments, the polynucleotide introduction need not result in integration but rather only transient maintenance of the polynucleotide introduced may be sufficient. In this way, one could have a short term effect, where cytotoxic cells could be introduced into the host and then turned on after a predetermined time, for example, after the cells have been able to migrate to a particular site for treatment.

Depending upon the nature of the cytotoxic cells and the diseases to be treated, the genetically engineered cytotoxic cells may be introduced into the subject, e.g. a mammal, in a wide variety of ways. The genetically engineered cytotoxic cells may be introduced at the site of the tumor. In one embodiment, the genetically engineered cytotoxic cells navigate to the cancer or are modified to navigate to the cancer. The number of genetically engineered cytotoxic cells that are employed will depend upon a number of factors such as the circumstances, the purpose for the introduction, the lifetime of the cells, the protocol to be used. For example, the number of administrations, the ability of the cells to multiply, and the stability of the recombinant construct. The genetically engineered cytotoxic cells may be applied as a dispersion injected at or near the site of interest. In one embodiment, the cells may be in a physiologically-acceptable medium.

It should be appreciated that the treatment method is subject to many variables, such as the cellular response to the FN3 CAR, the efficiency of expression of the FN3 CAR by the cytotoxic cells and, as appropriate, the level of secretion, the activity of the expressed FN3 CAR, the particular need of the subject, which may vary with time and circumstances, the rate of loss of the cellular activity as a result of loss of genetically engineered cytotoxic cells or the expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Non-limiting examples of current FN3 CAR targets for solid tumors that are also suitable as targets for an FN3 CAR of the present disclosure, include, EGFR (EGFR$^+$ solid tumors), EGFRvIII (glioblastoma), GD2 (neuroblastoma, Ewing's sarcoma, osteosarcoma, melanoma), IL13Rα2 (glioma), HER2 (HER2$^+$ solid tumors), Mesothelin (mesothelioma, pancreatic cancer, ovarian cancer), PSMA (prostate cancer), FAP (malignant pleural mesothelioma), GPC3 (hepatocellular carcinoma), MET (breast cancer), MUC16 (ovarian cancer), CEA (various solid tumors), Lewis-Y (solid tumors, myeloid malignancies), MUC1 (hepatocellular carcinoma, non-small cell lung carcinoma (NSCLC), pancreatic carcinoma, triple-negative invasive breast carcinoma). See, e.g., Fesnak et al., *Nature Rev. Cancer* (2016) 16:566-581.

Non-limiting examples of current FN3 CAR targets for hematological malignancies that are also suitable as targets for an FN3 CAR of the present disclosure, include, CD19 or CD20 (leukemia, lymphoma, multiple myeloma), CD22 (B cell malignancy), Igκ light chain (B cell malignancy), CD30 (lymphoma), CD138 (multiple myeloma), BCMA (multiple myeloma), CD33 (myeloid malignancies), CD123 (myeloid malignancies), NKG2D ligands (various hematological malignancies), ROR1 (leukemia). See, e.g., Fesnak et al., supra.

The types of cancers to be treated with the genetically engineered cytotoxic cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, the solid tumor is selected from the group consisting of a fibrosarcoma, a myxosarcoma, a liposarcoma, a chondrosarcoma, an osteosarcoma, and other sarcomas, a synovioma, a mesothelioma, an Ewing's tumor, a leiomyosarcoma, a rhabdomyosarcoma, a colon carcinoma, a lymphoid malignancy, a pancreatic cancer, a breast cancer, a lung cancer, an ovarian cancer, a prostate cancer, a hepatocellular carcinoma, a squamous cell carcinoma, a basal cell carcinoma, an adenocarcinoma, a sweat gland carcinoma, a medullary thyroid carcinoma, a papillary thyroid carcinoma, a pheochromocytomas sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a Wilms' tumor, a cervical cancer, a testicular tumor, a seminoma, a bladder carcinoma, a melanoma, a glioma, a glioblastoma, an astrocytoma, a CNS lymphoma, a germinoma, a medulloblastoma, a Schwannoma craniopharyogioma, an ependymoma, a pinealoma, a hemangioblastoma, an acoustic neuroma, an oligodendroglioma, a menangioma, a neuroblastoma, a retinoblastoma, and a brain metastasis.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the hematologic tumor is selected from the group consisting of a leukemia, a polycythemia vera, a lymphoma, a Hodgkin's lymphoma, a non-Hodgkin's lymphoma, a multiple myeloma, a Waldenstrom's macroglobulinemia, a heavy chain disease related tumor, a myelodysplastic syndrome related tumor, a hairy cell leukemia, and a myelodysplasia.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

A method of the present disclosure can also be used to treat inflammatory conditions and autoimmune disease. A subject FN3 CAR is expressed in a T-helper cell or a Tregs for use in an immunomodulatory method. Immunomodulatory methods include, e.g., enhancing an immune response in a mammalian subject toward a pathogen; enhancing an immune response in a subject who is immunocompromised; reducing an inflammatory response; reducing an immune response in a mammalian subject to an autoantigen, e.g., to treat an autoimmune disease; and reducing an immune response in a mammalian subject to a transplanted organ or tissue, to reduce organ or tissue rejection.

Where the method involves reducing an immune response to an autoantigen, the antigen used to activate the FN3 CAR is an autoantigen. Where the method involves reducing an immune response to a transplanted organ or tissue, the antigen used to activate the FN3 CAR is an antigen specific to the transplanted organ.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

Example 1: Identification of a BCMA-Specific FN3 Domain Polypeptide

Two FN3 domain libraries totaling 25 billion variants were expressed on the surface of M13 phage and stored as phage stocks in 1×PBS at 4° C. Each library stock had a titer of $1.5 \times 10^{13}$ cfu/ml.

The target protein BCMA-Fc Chimera (R&D Systems) was bound to Protein A Dynabeads (Invitrogen) at the following concentrations: Round 1: 500 nM; Round 2: 200 nM; and Round 3: 40 nM. IgG Fc protein (R&D Systems) was bound to protein A beads at 500 nM for all rounds as a subtractive screen. Each library was treated as separate reactions, thus three selections were performed. The supernatants containing the Fc cleared binders were transferred to the BCMA Protein A beads. For Round 1, $1 \times 10^{13}$ cfu/ml of phage for each library was added, and for each following round, $1 \times 10^{12}$ cfu/ml of phage was used. The beads were washed 6 times and the BCMA binding FN3 domain phage particles were eluted with a low pH buffer. The phage was titered on TG1 cells and amplified to make a Round 1 phage stock. Three rounds of phage selections were performed.

Round 2 and Round 3 phage were tested in a phage ELISA to test for functional display of FN3 domains on phage particles. Individual clones were picked into wells of a 96-well deep-well block and with the addition of M13K07 helper phage, FN3 domain phage particles were amplified. The phage was tested on BCMA and Fc only coated MaxiSorp plates. Clones with a high ratio of BCMA binding signal to Fc binding signal were sequenced.

Yeast display was used to sort out the highest BCMA affinity binders. The Round 3 BCMA binding FN3 domain phage was cloned into a modified pYD1 vector (Invitrogen) displaying the AGA2 protein as a C-terminus fusion protein. First, the phagemid DNA was amplified in TG1 and the DNA is maxi-prepped (Qiagen). The FN3 domain sequences was excised from the phagemid vector by BamHI and XhoI and was transformed into EBY100 yeast with linearized modified pYD1 vector the DNA by electroporation. The FN3 domains was expressed in galactose media. The first sort isolated the top 0.5%-1% binders to BCMA as a population. For Sort #2, eight 96-well plates of individual yeast cells was sorted for the top 0.1% of BCMA-binding phage. DNA was isolated by yeast mini-prep (ZymoResearch) and sequenced.

BCMA-binding FN3 domains were cloned into the pET-24a vector (Novagen) for soluble expression. The BCMA-binding FN3 domains was purified via the C-terminal 6X HIS-tag.

BCMA-specific FN3 domain binding affinities were determined using an Octet bio-layer interferometry system (Pall ForteBio). The BCMA-Fc Chimera target protein was immobilized on Protein A sensor tips at 25 μg/ml. BCMA-specific FN3 domain binding was tested at 10 μg/ml. Dissociation was monitored in 1× kinetic buffer only. The $k_a$, $k_d$ and $K_D$ values were determined by ForteBio software. BCMA-specific FN3 domains were ranked by highest to lowest binding affinity to BCMA.

An exemplary BCMA-binding FN3 domain sequence is shown below:

```
                                           (SEQ ID NO: 42)
N V S P P R R A R V T D A T E T T I T I P W A L A G

S P V V R F Q V D A V P A N G Q T P I Q R T I Q P S

K R G Y T I T G L Q P G T D Y K I Y L Y T L N G P V

V I D A S T
```

Example 2: Cloning of a Chimeric Antigen Receptor Specific for a Cancer Antigen

A natural variant combinatorial FN3 domain library will be generated as described in U.S. Pat. No. 8,680,019. The library of fibronectin binding domains will be constructed in phagemid vectors. Phage will be incubated with a biotinylated cancer antigen, e.g., VEGF (121), that will have been pre-bound to streptavidin-coated magnetic beads for 1 hr at room temperature in PBS-2.5% non-fat dry milk. Following washes with PBS-0.1% Tween-20, bound phage will be eluted with 0.1N HCl and propagated in TG1 cells for the next round of selection. In round 1 the VEGF concentration that will be used is 1 μM and this will be reduced 5-fold per round such that the final round of selection contains 20 nM VEGF. To measure relative enrichment, phage prepared from a non-displaying control phagemid (pBC), which confers chloramphenicol resistance, will also be included in the selection reactions. In each round, a 2 to 5-fold enrichment of library phage is expected as compared to the non-displaying control phage.

After the selections, individual clones will be screened for binding to VEGF by phage ELISA. Positive clones will be rescreened by phage ELISA for binding specificity against VEGF, TNFα or a blank plate, to identify VEGF-specific variants. VEGF-specific variants will be further developed into candidate VEGF-specific targeting regions comprising FN3 domain polypeptides.

Using standard molecular biology techniques known in the art, the VEGF-specific targeting region will be used to construct an FN3 CAR molecule. T cells will be transduced with the FN3 CAR molecule such that the T cells express the FN3 CAR molecule (FN3 CAR-T cells). CHO cells expressing the target VEGF or regular CHO cells that do not express the target VEGF will be separately treated with FN3 CAR-T cells. Non-transduced T cells (without the FN3 CAR molecule) will be used as a control.

Using similar experimental procedures, an AXL-specific targeting region can be used to construct an FN3 CAR molecule (i.e., a AXL-specific FN3 CAR molecule). Suitable AXL-specific FN3 domain polypeptides are described elsewhere herein.

Figure 2:
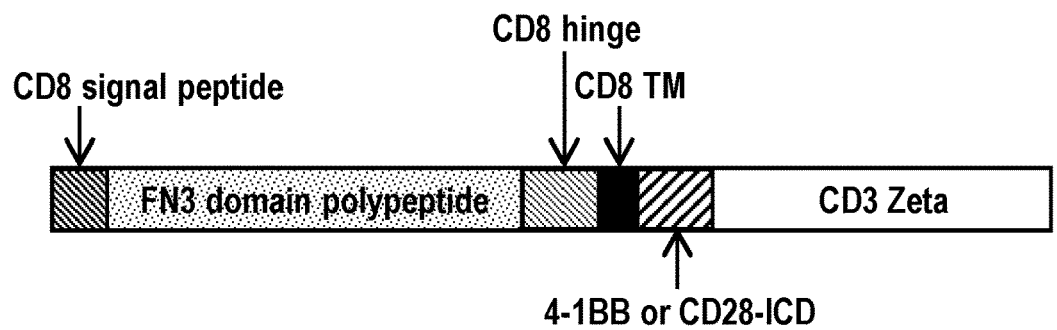
FIG. 2 depicts a schematic of the polynucleotide structure comprising a sequence encoding a subject FN3 CAR of the present disclosure.

FIG. 1 and FIG. 2 depict schematics showing the general structure of an FN3 CAR molecule.

Example 3: Bi-Functional FN3 Domain Polypeptide CAR-T

A bispecific CAR-T comprising an FN3 domain polypeptide can be built that expresses: i. a tumor antigen binding FN3 domain polypeptide, ii. a T-cell surface receptor binding FN3 domain polypeptide, and iii. a linker. Potential tumor antigen targets are BCMA and CD-19. BCMA is involved in blood cancers, such as multiple myeloma and leukemia and can cause cell survival and cell proliferation. CD19 is found on B-cell cancers. Two T-cell receptors that can be targeted with a FN3 domain polypeptide are PD-1 and CTLA-4. Both these receptors are expressed on activated T-cells and transmit both inhibitory and co-stimulatory signals.

Another example of a bispecific CAR-T comprising an FN3 domain polypeptide can be built that comprises: i. an AXL binding FN3 domain polypeptide, ii. a T-cell surface receptor binding FN3 domain polypeptide or a T-cell surface receptor binding scFv (e.g., anti-CD3 scFv), and iii. a linker. Suitable AXL binding FN3 domain polypeptide sequences are described elsewhere herein.

Using standard molecular biology techniques known in the art, the bispecific targeting region will be used to construct an FN3 CAR molecule. T cells will be transduced with the FN3 CAR or FN3/scFv CAR molecule such that the T cells express the FN3 CAR or FN3/scFv CAR molecule (FN3 CAR-T cells, or FN3/scFv CAR-T cells). CHO cells expressing the target antigen or regular CHO cells that do not express the target antigen will be separately treated with FN3 CAR-T or FN3/scFv CAR-T cells. Non-transduced T cells (without the FN3 CAR or FN3/scFv CAR molecule) will be used as a control.

Figure 3:
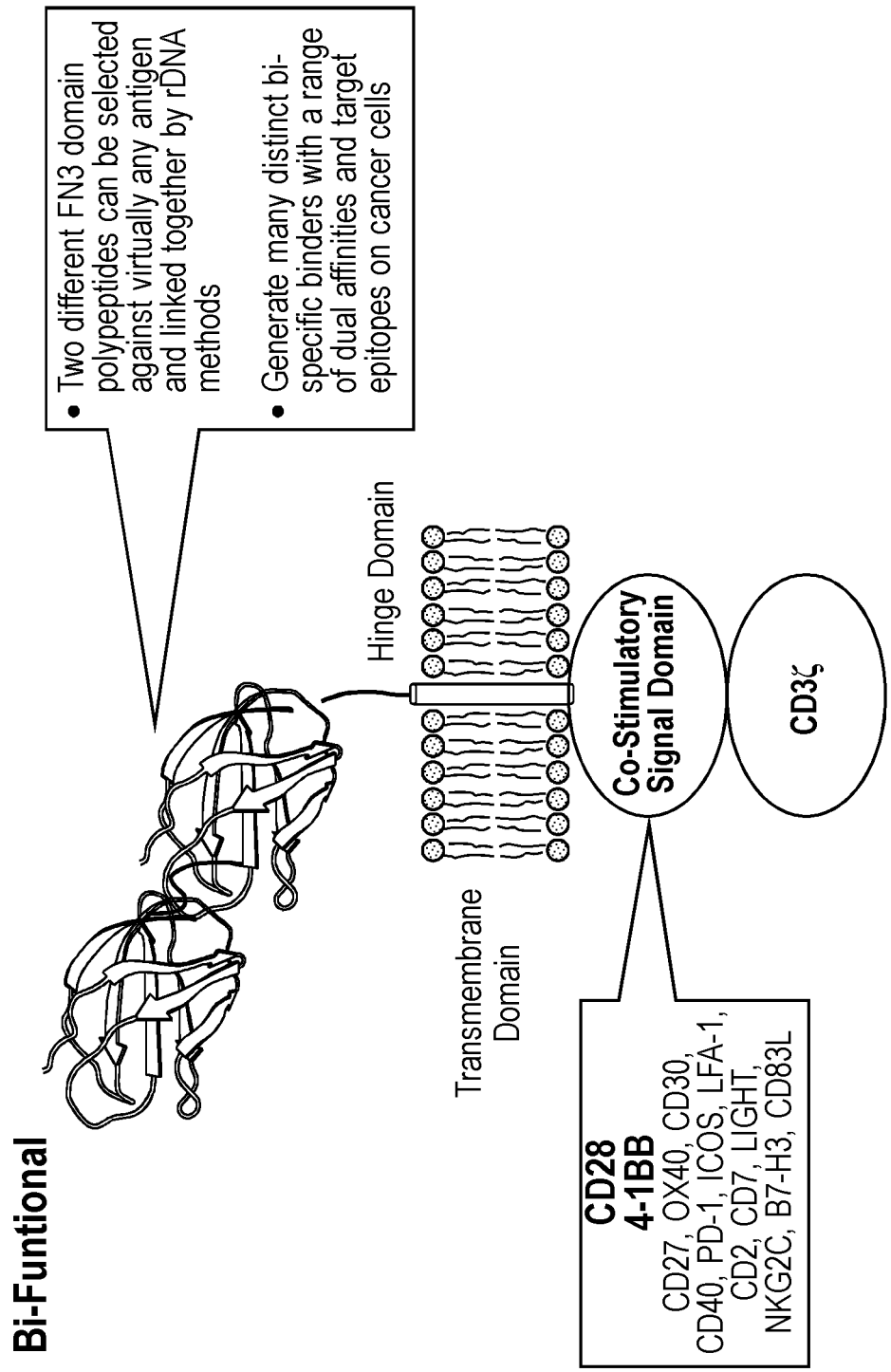
FIG. 3 depicts a schematic of a subject multispecific FN3 CAR of the present disclosure.

FIG. 3 depicts a schematic showing the general structure of a bispecific FN3 CAR molecule.

The linker between the two FN3 domain polypeptides (of i. and ii.) can be a 20-base pair or a 14-base pair sequence derived from a natural fibronectin sequence. Exemplary 20-base pair and 14-base pair linkers are shown below: 20 base pair linker: AIDAPSNLRFLATTPNSLLV (SEQ ID NO:21) 14 base pair linker: AIDAPSNLRFLATT (SEQ ID NO:22)

This linker sequence is derived from the natural fibronectin sequence between the end of the 14$^{th}$ FN3 domain and the BC loops of the 15$^{th}$ FN3 domain. Using this endogenous sequence will lessen the likelihood of an immune response to the linker sequence.

An exemplary sequence between the 14$^{th}$ FN3 domain and the 15$^{th}$ FN3 domain of a natural fibronectin is show below:

(SEQ ID NO: 23)
NVSPPRRARVTDATETTITISWRTKTETITGFQVDAVPANGQTPIQRTIKP

DVRSYTITGLQPGTDYKIYLYTLNDNARSSPVVIDASTAIDAPSNLRFLAT

TPNSLLVSWQPPRARITGYIIKYEKPGSPPREVVPRPRPGVTEATITGLEP

GTEYTIYVIALKNNQKSEPLIGRKKT.

Example 4: FN3 Domain Bispecific T Cell Engager

Screening

Phage Display: FN3 domain libraries were screened by phage display to discover FN3 domain polypeptides that bind to the tyrosine kinase receptor, AXL (R&D Systems cat #154-AL). Three rounds of selection were completed with the target concentration of: round 1: 500 nM and phage library 10$^{13}$; round 2: 200 nM and phage library 10$^{12}$; and round 3: 40 nM and phage library 10$^{12}$.

Phage Screening and Analysis of FN3 Libraries for AXL Binding Activity: Individual clones (1732) were validated by phage ELISA and 576 were sequenced, resulting in 157 unique clones.

Yeast Display: The round 3 phage stocks were cloned into the yeast display vector, pYD1, and two rounds of sorting were completed. The first yeast sort used 25 nM of AXL target protein and the top 0.1-0.5% of binders were sorted as an enriched population. The second yeast sort used 2.5 nM of the soluble target protein and resulted in 192 individual clones representing 67 unique sequences.

Figure 4:
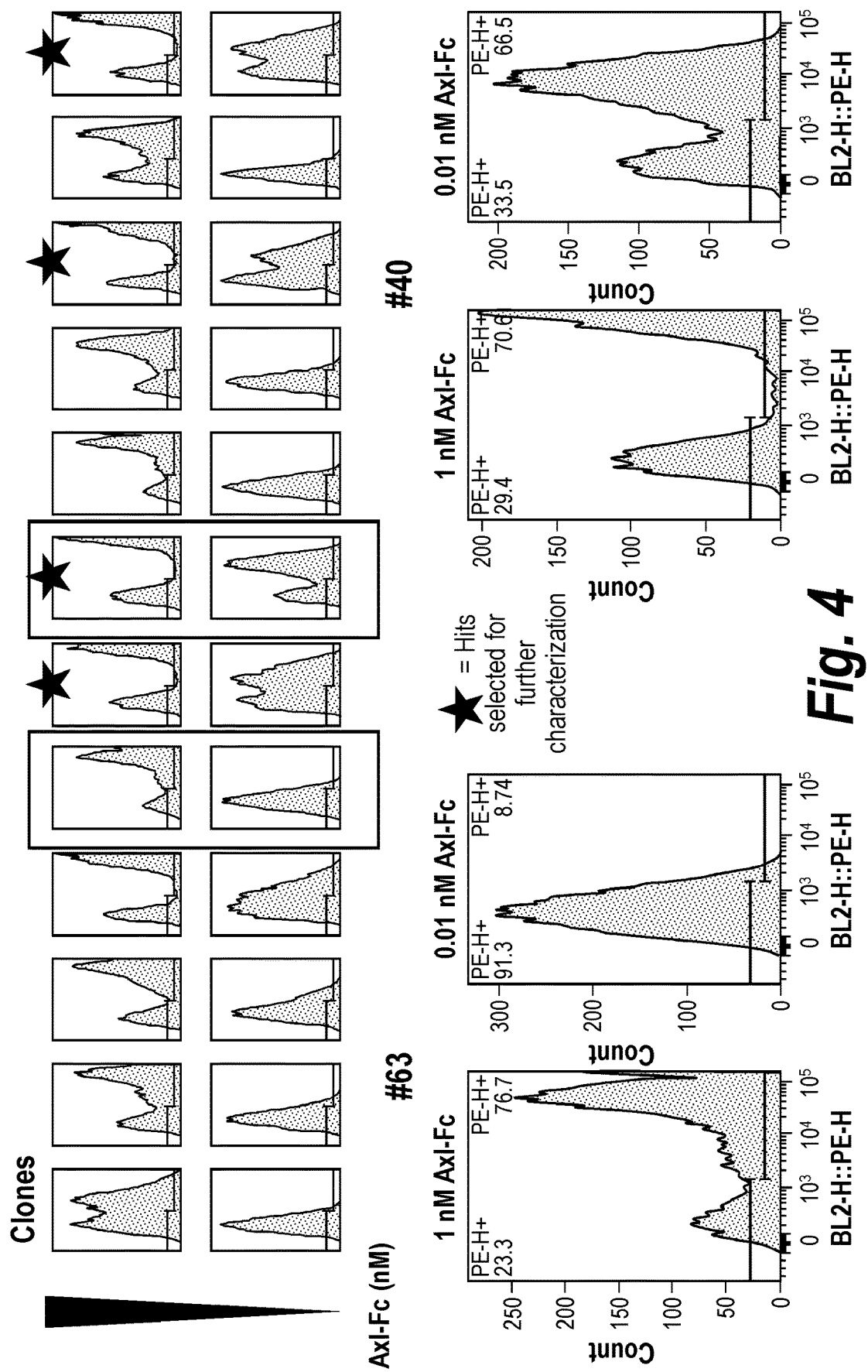
FIG. 4 depicts FACS analysis of affinity screening.

Yeast Screening and Analysis of FN3 Libraries for AXL Binding Activity Using FACS: Yeast binding affinity screening of single clones using Axl soluble target was performed according to the following: Yeast single clones (10 µl OD=0.1-0.2) have been tested against 1 and 0.01 nM of Axl-Fc and stained using 1:25 anti Fc-PE (109116098 Jackson Immunoresearch) in FACS staining media (PBS-BSA 0.1%) (FIG. 4).

Yeast specificity screening of single clones using MDA-MB-231 cancer cell lines and KO MDA-MB-231 cell line using FACS was performed according to the following: Adherent Target cells (Axl expressing and Axl KO cells) were sided on 6wp the day before the experiment. Cells were labelled with Vybrant™ DiD Cell-Labeling Solution (Thermofischer Scientific Catalog number: V22887) following suggested protocols. Cells were successively incubated with 100 µl of yeast FN3 domain single clone. After extensive washing yeast binding to the cells was detected using anti HisTag (R&D ref) 3 µl per 6wp (30 min at 4° C.). After washing, cells were scraped from the plate and analyzed via FACS. Specific clones were identified if a double color population (DiD-red and 488-green) only in MDA231 cells line and not in the KO was observed (FIG. 5).

Cloning AXL-Specific FN3Domains

In total, 59 FN3 domains specific for AXL discovered by phage display and yeast display were cloned into the E. coli vector pET-24a, for soluble protein expression. The AXL FN3 domains were tested for AXL binding by protein ELISA and by SPR on an Octet (Forte Biosystems). Binding affinities were observed to be as low as 2 nM (FIG. 6). Specificity on MDA-MB-231

Figures 7A, 7B:
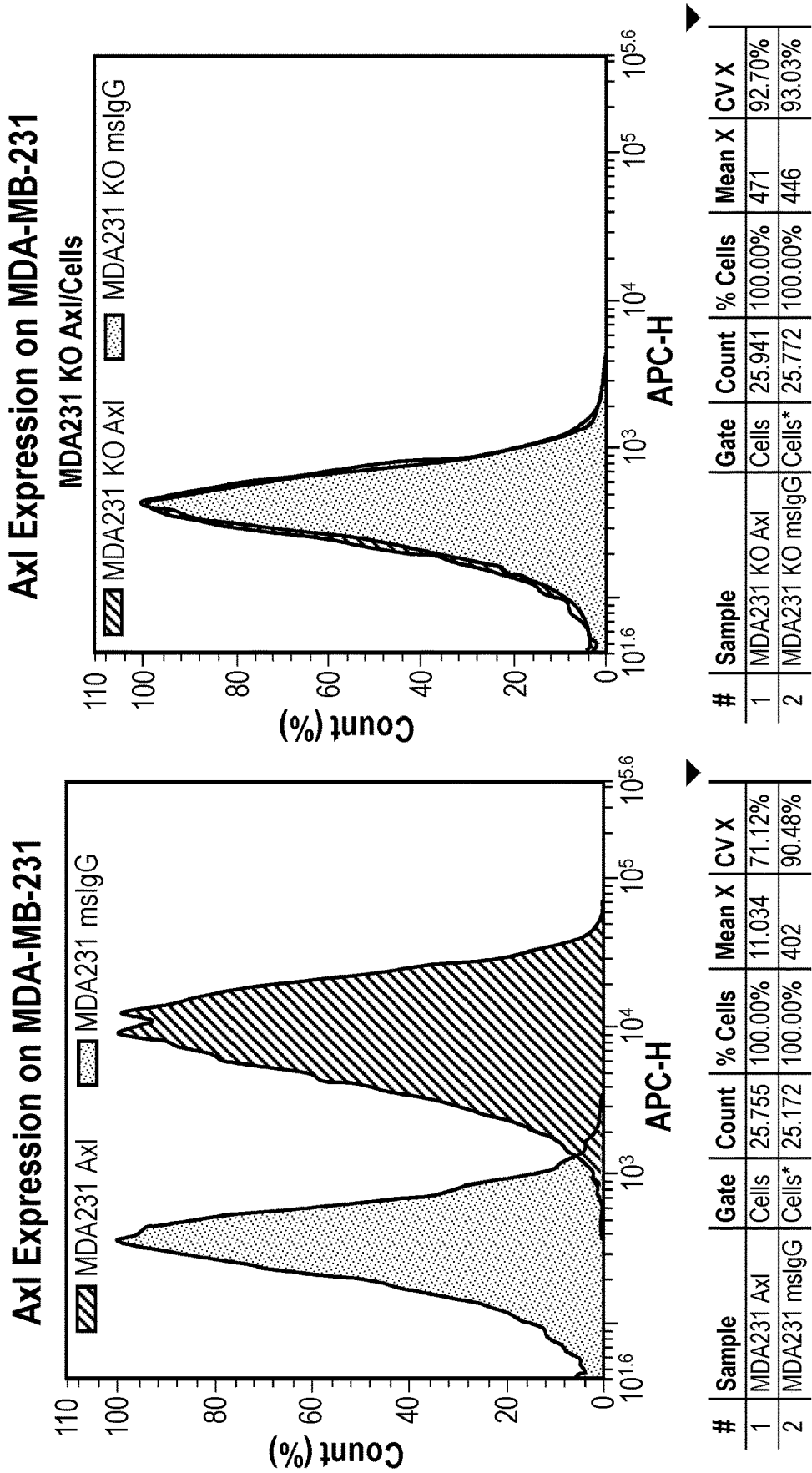
FIGS. 7A and 7B depict FACS analysis of specificity screening.
Figure 9:
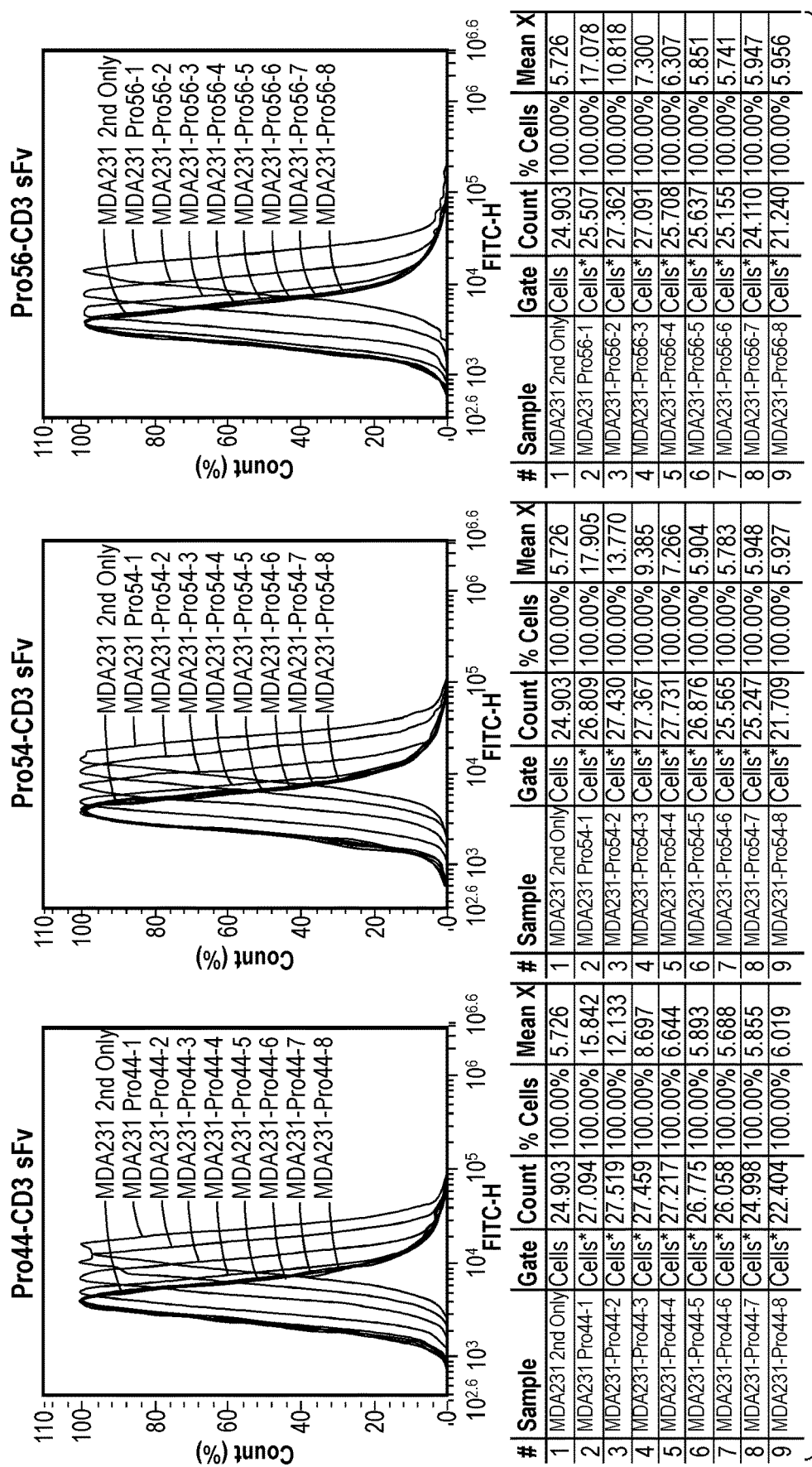
FIG. 9 depicts FACS analysis of FN3 domain-scFv fusions.

The AXL FN3 domain binders were screened against MDA-MB-231 cells, which have high expression of the AXL receptor, and an AXL Knock Out (KO) MDA-MB-231 cell line (FIGS. 7A and 7B). Four FN3 domains (AXL #44, AXL #53, AXL #54, and AXL #56) showed no non-specific binding. They bound to the MDA-MB-231 cells with high affinity and had no binding to the knockout cells (FIGS. 9A and 9B).

AXL #44

(SEQ ID NO: 33)
N V S P P R R A R V T D A T E T T I T I R W E G R G

V I G F Q V D A V P A N G Q T P I Q R T I K P D V R

S Y T I T G L Q P G T D Y K I Y L Y T L P N I G T G

H F S S S P V V I D A S T.

AXL #53

(SEQ ID NO: 34)
N V S P P R R A R V T D A T E T T I T I S W E G S P

S T F I G F Q V D A V P A N G Q T P I Q R T I K P D

V R S Y T I T G L Q P G T D Y K I Y L Y T L P D F G

R G H F T S S P V V I D A S T.

AXL #54

(SEQ ID NO: 35)
N V S P P R R A R V T D A T E T T I T I R W E G R G

V I G F Q V D A V P A N G Q T P I Q R T I K P D V R

S Y T I T G L Q P G T D Y K I Y L Y T L P D F G R G

H F T S S P V V I D A S T.

AXL #56

(SEQ ID NO: 36)
N V S P P R R A R V T D A T E T T I T I S W R V S P

S T V V G L Q V D A V P A N G Q T P I Q R T I K P D

V R S Y T I T G L Q P G T D Y K I Y L Y T L N V I G

G S A H A S S P V V I D A S T.

AXL-CD3 Pronectins

Figure 8:
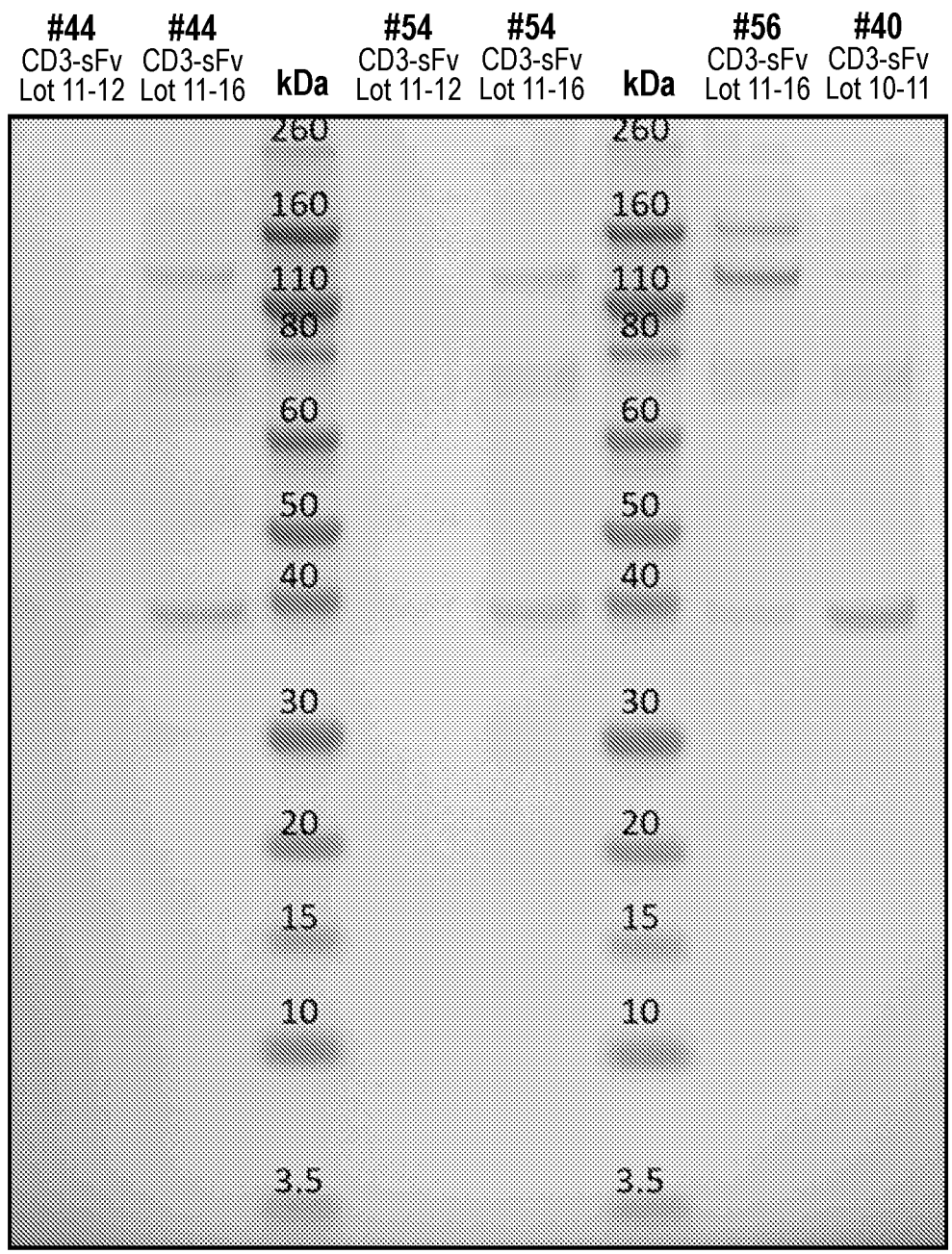
FIG. 8 depicts a Coomassie stained gel of various proteins according to the present disclosure.

FN3 domain AXL #54 and the scFV SP34 CD3 was cloned into the vector pmaxCloning (LONZA) through the EcoRV site. The FN3 domain was cloned as a G-BLOCK (IDT) by Gibson Assembly and sequenced verified. Plasmid DNA was transfected into 293-T by PEI and supernatant containing the AXL #54-CD3 FN3 domain-scFv fusion was harvested. Protein was purified by HIS-gravity column (GE Healthcare). FN3 domains AXL #44 and AXL #56 were also cloned as fusions to the scFV SP34 CD3. The predicted size is 37.3 kDa (FIG. 8).

44 CD3

(SEQ ID NO: 37)
MDMRVPAQLLGLLLLWLSGARCNVSPPRRARVTDATETTITIRWEGRGVIG

FQVDAVPANGQTPIQRTIKPDVRSYTITGLQPGTDYKIYLYTLPNIGTGHF

-continued

SSSPVVIDASTGGGGSELVVTQEPSLTVSPGGTVTLTCRSSTGAVTTSNYA

NWVQQKPGQAPRGLIGGTNKRAPGTPARFSGSLLGGKAALTLSGVQPEDEA

EYYCALWYSNLWVFGGGTKLTVLGGGGSGGGGSGGGGSEVQLLESGGGLVQ

PGGSLKLSCAASGFTFNTYAMNWVRQAPGKGLEWVARIRSKYNNYATYYAD

SVKDRFTISRDDSKNTAYLQMNNLKTEDTAVYYCVRHGNFGNSYVSWFAYW

GQGTLVTVSSHHHHHH.

54 CD3

(SEQ ID NO: 38)
MDMRVPAQLLGLLLLWLSGARCNVSPPRRARVTDATETTITIRWEGRGVIG

FQVDAVPANGQTPIQRTIKPDVRSYTITGLQPGTDYKIYLYTLPDFGRGHF

TSSPVVIDASTGGGGSELVVTQEPSLTVSPGGTVTLTCRSSTGAVTTSNYA

NWVQQKPGQAPRGLIGGTNKRAPGTPARFSGSLLGGKAALTLSGVQPEDEA

EYYCALWYSNLWVFGGGTKLTVLGGGGSGGGGSGGGGSEVQLLESGGGLVQ

PGGSLKLSCAASGFTFNTYAMNWVRQAPGKGLEWVARIRSKYNNYATYYAD

SVKDRFTISRDDSKNTAYLQMNNLKTEDTAVYYCVRHGNFGNSYVSWFAYW

GQGTLVTVSSHHHHHH.

56 CD3

(SEQ ID NO: 39)
MDMRVPAQLLGLLLLWLSGARCNVSPPRRARVTDATETTITISWRVSPSTV

VGLQVDAVPANGQTPIQRTIKPDVRSYTITGLQPGTDYKIYLYTLNVIGGS

AHASSPVVIDASTGGGGSELVVTQEPSLTVSPGGTVTLTCRSSTGAVTTSN

YANWVQQKPGQAPRGLIGGTNKRAPGTPARFSGSLLGGKAALTLSGVQPED

EAEYYCALWYSNLWVFGGGTKLTVLGGGGSGGGGSGGGGSEVQLLESGGGL

VQPGGSLKLSCAASGFTFNTYAMNWVRQAPGKGLEWVARIRSKYNNYATYY

ADSVKDRFTISRDDSKNTAYLQMNNLKTEDTAVYYCVRHGNFGNSYVSWFA

YWGQGTLVTVSSHHHHHH.

T Cell Dependent Cellular Toxicity (TDCC) Assay

The AXL-CD3 FN3 domain-scFv fusions were titrated 1:4 starting at 500 nM on the MDA-MB-231 and MDA-MB-231 KO cell lines and the results showed they are specific binders to AXL. The AXL-CD3 FN3 domain-scFv fusions were tested in a Caspace-Glo 3/7 cytotoxicity assay (Promega). The starting concentration of the AXL-CD3 FN3 domain-scFv fusions were 500 nM and the titration was 1:4 for 8 points. The MDA-MB-231 cells were seeded at 10,000 cells/well and the PBMCs, isolated from blood containing greater than 70% lymphocytes, and were added at 100,000 cells/well. Thus, the Target: Effector ratio was 1:10. After 48 hours of incubation the Caspace-Glo reagent was added and luminescence measured (FIG. 10).

Figures 10A, 10B:
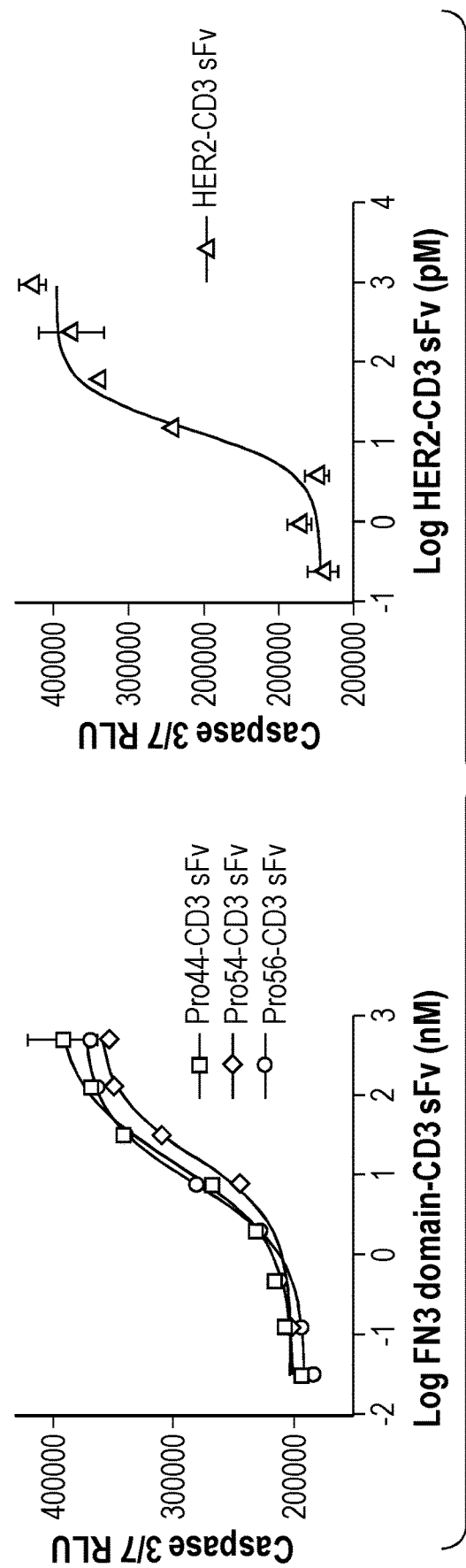
FIGS. 10A and 10B depict T-cell dependent cellular toxicity (TDCC) assay killing curves for FN3 domain-scFv fusions, and EC50 values, respectively.

The killing curves were graphed and EC50 were calculated (FIGS. 10A and 10B).

T Cell Activation Assay

Figure 11A:
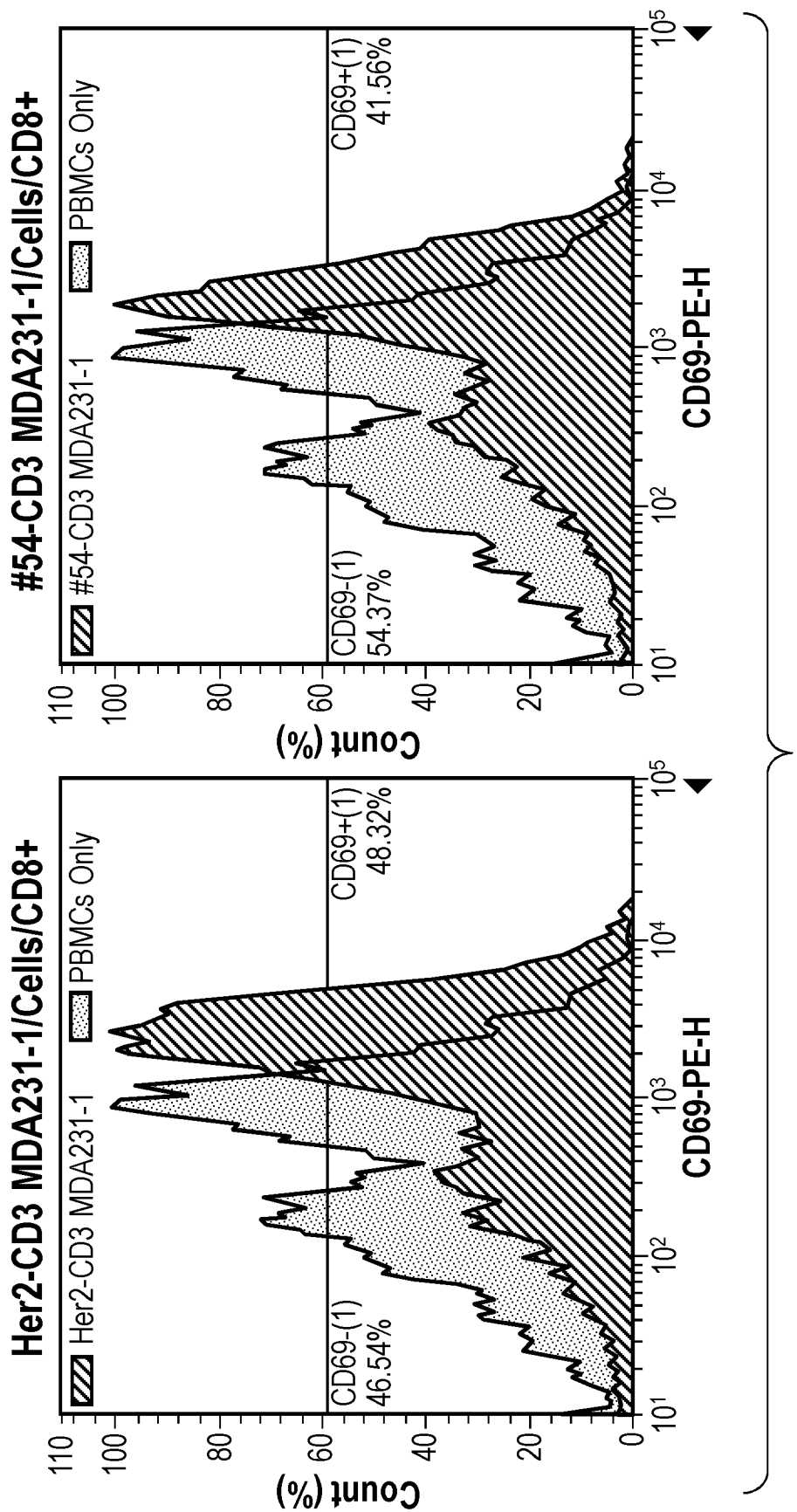
FIGS. 11A and 11B depicts FACS analysis showing T cell activation, and quantification of the same, respectively.
Figure 11B:
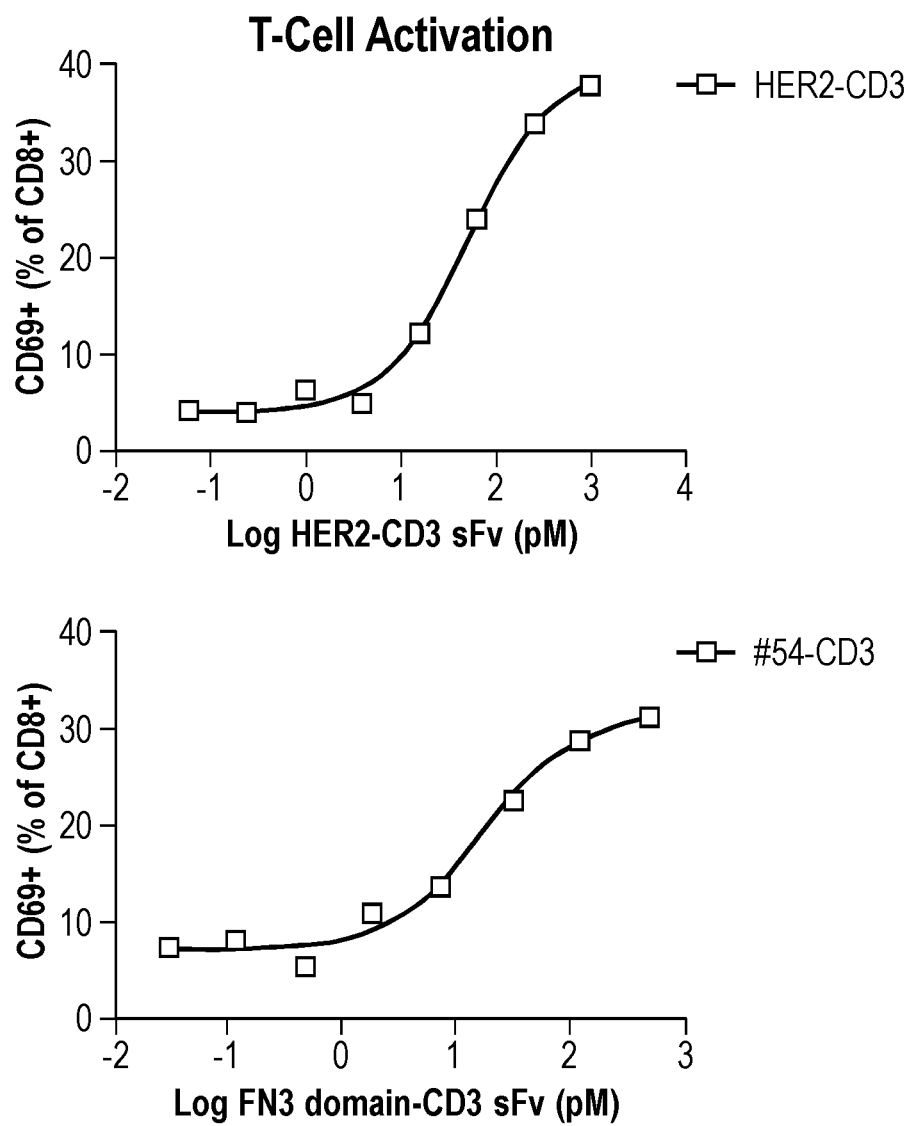

T-cell Activation was confirmed by the increased expression of CD69 in the presence of the AXL-CD3 FN3 domain-scFv fusion and target cell expressing the AXL receptor. FN3 domain-scFv fusion AXL #54-CD3 was titrated (0.03-500 nM) on MDA-MB-231 cells and PBMC (CD8+). Cells were stained with CD8 and CD69 antibodies and the increase in the CD69 expression in the CD8+ population was measured as a 41% increase in CD69 compared to PBMCs only. The scFV CD3 was found to be functional (FIGS. 11A and 11B).

AXL-Fc Competition/TDCC Assay

Figure 12:
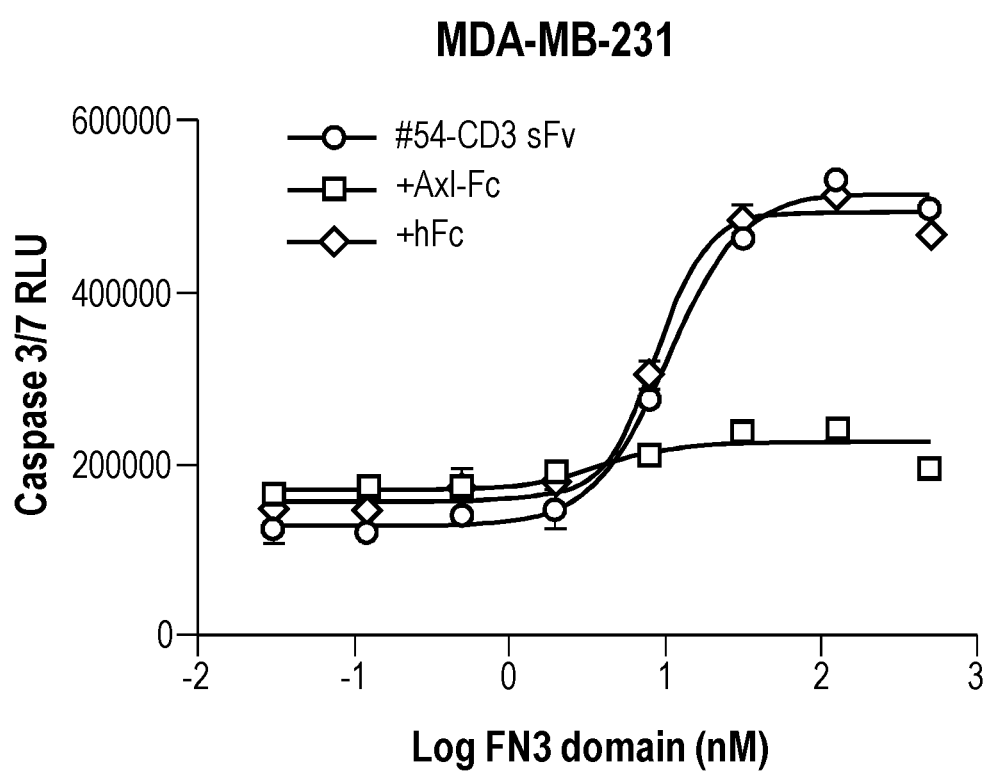
FIG. 12 depicts a graph showing the specificity of an AXL-CD3 FN3 domain-scFv fusion measured with competition from AXL-Fc protein in TDCC assay.

To test the target specificity of the AXL-CD3 FN3 domain-scFv fusions, a cytotoxicity assay with AXL-Fc competition was performed. The assay was set up with the AXL-Fc concentration set at 500 nM and control human Fc at 500 nM. The same assay was run with PBMCs, MDA-MB-231 cells and the titration of AXL #54-CD3. AXL-Fc decreased cytotoxicity in the assay due to binding competition with the AXL-CD3 FN3 domain-scFv fusion. The AXL #54 was found to be target specific in the cytotoxicity assay (FIG. 12).

Example 5: AXL Dimer and Trimer Bispecific T Cell Engager

A dimer construct and one trimer construct were cloned by Gibson Assembly using G-Blocks in to the pmaxCloning vector. The dimer fusion construct was AXL #44-AXL54-CD3 and the trimer fusion construct was AXL #44-AXL54-AXL56-CD3. Both constructs were expressed in 293-T cells and purified using the 6XHIS-tag.

AXL#44-AXL#54-CD3

(SEQ ID NO: 40)
M D M R V P A Q L L G L L L L W L S G A R C N V S P
P R R A R V T D A T E T T I T I R W E G R G V I G F
Q V D A V P A N G Q T P I Q R T I K P D V R S Y T I
T G L Q P G T D Y K I Y L Y T L P N I G T G H F S S
S P V V I D A S T G G G G S G G G G S G G G G S N V
S P P R R A R V T D A T E T T I T I R W E G R G V I
G F Q V D A V P A N G Q T P I Q R T I K P D V R S Y
T I T G L Q P G T D Y K I Y L Y T L P D F G R G H F
T S S P V V I D A S T G G G G S E L V V T Q E P S L
T V S P G G T V T L T C R S S T G A V T T S N Y A N
W V Q Q K P G Q A P R G L I G G T N K R A P G T P A
R F S G S L L G G K A A L T L S G V Q P E D E A E Y
Y C A L W Y S N L W V F G G G T K L T V L G G G G S
G G G G S G G G G S E V Q L L E S G G G L V Q P G G
S L K L S C A A S G F T F N T Y A M N W V R Q A P G
K G L E W V A R I R S K Y N N Y A T Y Y A D S V K D
R F T I S R D D S K N T A Y L Q M N N L K T E D T A
V Y Y C V R H G N F G N S Y V S W F A Y W G Q G T L
V T V S S H H H H H H

AXL#44-AXL#54-AXL#56-CD3

(SEQ ID NO: 41)
MDMRVPAQLLGLLLLWLSGARCNVSPPRRARVTDATETTITIRWEGRGVIG

FQVDAVPANGQTPIQRTIKPDVRSYTITGLQPGTDYKIYLYTLPNIGTGHF

SSSPVVIDASTGGGSGGGGSGGGGSNVSPPRRARVTDATETTITIRWEGR

GVIGFQVDAVPANGQTPIQRTIKPDVRSYTITGLQPGTDYKIYLYTLPDFG

RGHFTSSPVVIDASTGGGGSGGGGSGGGGNVSPPRRARVTDATETTITISW

RVSPSTVVGLQVDAVPANGQTPIQRTIKPDVRSYTITGLQPGTDYKIYLYT

LNVIGGSAHASSPVVIDASTGGGGSELVVTQEPSLTVSPGGTVTLTCRSST
GAVTTSNYANWVQQKPGQAPRGLIGGTNKRAPGTPARFSGSLLGGKAALTL
SGVQPEDEAEYYCALWYSNLWVFGGGTKLTVLGGGGSGGGGSGGGGSEVQL

LESGGGLVQPGGSLKLSCAASGFTFNTYAMNWVRQAPGKGLEWVARIRSKY
NNYATYYADSVKDRFTISRDDSKNTAYLQMNNLKTEDTAVYYCVRHGNFGN
SYVSWFAYWGQGTLVTVSSHHHHHH

What is claimed is:

1. A chimeric antigen receptor (CAR) comprising:
   i) at least one antigen specific targeting region comprising a fibronectin type 3 (FN3) domain polypeptide;
   ii) a transmembrane domain; and
   iii) an intracellular signaling domain,
   wherein the CAR further comprises an extracellular spacer domain
   wherein the least one antigen specific targeting region comprises an amino acid sequence set forth in SEQ ID NO: 33.

2. The chimeric antigen receptor of claim 1, wherein the extracellular spacer domain is selected from the group consisting of an Fc fragment of an antibody, a hinge region of an antibody, a CH2 region of an antibody, a CH3 region of an antibody, an artificial spacer sequence, a hinge consisting of an amino acid sequence of CD8, and any combination thereof.

3. The chimeric antigen receptor of claim 1, wherein the chimeric antigen receptor further comprises at least one co-stimulatory domain.

4. The chimeric antigen receptor of claim 1, wherein the transmembrane domain is selected from the group consisting of an artificial hydrophobic sequence and transmembrane domains of a type I transmembrane protein, an alpha, beta, or zeta chain of a T cell receptor, a cluster of differentiation 28 (CD28), a CD3 epsilon, a CD45, a CD4, a CD5, a CD8, a CD9, a CD16, a CD22, a CD33, a CD37, a CD64, a CD80, a CD86, a CD134, a CD137, and a CD154.

5. The chimeric antigen receptor of claim 1, wherein the intracellular signaling domain is selected from the group consisting of cytoplasmic signaling domains of a human CD3 zeta chain, a FcyRIII, a FcsRI, a cytoplasmic tail of an Fc receptor, an immunoreceptor tyrosine-based activation motif (ITAM) bearing cytoplasmic receptors, a TCR zeta, a FcR gamma, a FcR beta, a CD3 gamma, a CD3 delta, a CD3 epsilon, a CD5, a CD22, a CD79a, a CD79b, and a CD66d.

* * * * *

SEQUENCE LISTING

```
<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: Residues 1-5 are may be repeated more than one
      time.

<400> SEQUENCE: 1

Gly Ser Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(4)
<223> OTHER INFORMATION: Residues 1-4 may be repeated more than one
      time.

<400> SEQUENCE: 2

Gly Gly Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: Synthetic sequence

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence

<400> SEQUENCE: 4

Gly Gly Ser Gly Gly
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Synthetic sequence

<400> SEQUENCE: 5

Gly Ser Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Gly Ser Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic sequence

<400> SEQUENCE: 7

Gly Gly Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic sequence

<400> SEQUENCE: 8

Gly Ser Ser Ser Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Asp Lys Thr His Thr
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic sequence

<400> SEQUENCE: 10

Cys Pro Pro Cys
1

<210> SEQ ID NO 11
<211> LENGTH: 15
<212> TYPE: PRT
<213> ORGANISM: Artificial Sequence
<220> FEATURE:
```

<223> OTHER INFORMATION: Synthetic sequence

<400> SEQUENCE: 11

Cys Pro Glu Pro Lys Ser Cys Asp Thr Pro Pro Cys Pro Arg
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Synthetic sequence

<400> SEQUENCE: 12

Glu Leu Lys Thr Pro Leu Gly Asp Thr Thr His Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic sequence

<400> SEQUENCE: 13

Lys Ser Cys Asp Lys Thr His Thr Cys Pro
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic sequence

<400> SEQUENCE: 14

Lys Cys Cys Val Asp Cys Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic sequence

<400> SEQUENCE: 15

Lys Tyr Gly Pro Pro Cys Pro
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic sequence

<400> SEQUENCE: 16

Glu Pro Lys Ser Cys Asp Lys Thr His Thr Cys Pro Pro Cys Pro
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Synthetic sequence

```
<400> SEQUENCE: 17

Glu Arg Lys Cys Cys Val Glu Cys Pro Pro Cys Pro
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic sequence

<400> SEQUENCE: 18

Glu Leu Lys Thr Pro Leu Gly Asp Thr Thr His Thr Cys Pro Arg Cys
1               5                   10                  15

Pro

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence

<400> SEQUENCE: 19

Ser Pro Asn Met Val Pro His Ala His His Ala Gln
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic sequence

<400> SEQUENCE: 20

Glu Pro Lys Ser Cys Asp Lys Thr Tyr Thr Cys Pro Pro Cys Pro
1               5                   10                  15

<210> SEQ ID NO 21
<211> LENGTH: 20
<212> TYPE: PRT
<213> ORGANISM: Artificial Sequence
<220> FEATURE:
<223> OTHER INFORMATION: Synthetic sequence

<400> SEQUENCE: 21

Ala Ile Asp Ala Pro Ser Asn Leu Arg Phe Leu Ala Thr Thr Pro Asn
1               5                   10                  15

Ser Leu Leu Val
            20

<210> SEQ ID NO 22
<211> LENGTH: 14
<212> TYPE: PRT
<213> ORGANISM: Artificial Sequence
<220> FEATURE:
<223> OTHER INFORMATION: Synthetic sequence

<400> SEQUENCE: 22

Ala Ile Asp Ala Pro Ser Asn Leu Arg Phe Leu Ala Thr Thr
1               5                   10

<210> SEQ ID NO 23
<211> LENGTH: 179
```

```
<212> TYPE: PRT
<213> ORGANISM: Artificial Sequence
<220> FEATURE:
<223> OTHER INFORMATION: Synthetic sequence

<400> SEQUENCE: 23

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr Ala Ile Asp Ala Pro Ser Asn
                85                  90                  95

Leu Arg Phe Leu Ala Thr Thr Pro Asn Ser Leu Leu Val Ser Trp Gln
            100                 105                 110

Pro Pro Arg Ala Arg Ile Thr Gly Tyr Ile Ile Lys Tyr Glu Lys Pro
        115                 120                 125

Gly Ser Pro Pro Arg Glu Val Val Pro Arg Pro Arg Pro Gly Val Thr
    130                 135                 140

Glu Ala Thr Ile Thr Gly Leu Glu Pro Gly Thr Glu Tyr Thr Ile Tyr
145                 150                 155                 160

Val Ile Ala Leu Lys Asn Asn Gln Lys Ser Pro Leu Ile Gly Arg
                165                 170                 175

Lys Lys Thr

<210> SEQ ID NO 24
<211> LENGTH: 9
<212> TYPE: PRT
<213> ORGANISM: Artificial Sequence
<220> FEATURE:
<223> OTHER INFORMATION: Synthetic sequence

<400> SEQUENCE: 24

Tyr Pro Tyr Asp Val Pro Asp Tyr Ala
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic sequence

<400> SEQUENCE: 25

Asp Tyr Lys Asp Asp Asp Asp Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic sequence

<400> SEQUENCE: 26

Glu Gln Lys Leu Ile Ser Glu Glu Asp Leu
```

<210> SEQ ID NO 27
<211> LENGTH: 5
<212> TYPE: PRT
<213> ORGANISM: Artificial Sequence
<220> FEATURE:
<223> OTHER INFORMATION: Synthetic sequence

<400> SEQUENCE: 27

His His His His His
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic sequence

<400> SEQUENCE: 28

His His His His His His
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic sequence

<400> SEQUENCE: 29

Trp Ser His Pro Gln Phe Glu Lys
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic sequence

<400> SEQUENCE: 30

Arg Tyr Ile Arg Ser
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic sequence

<400> SEQUENCE: 31

Pro His His Thr
1

<210> SEQ ID NO 32
<211> LENGTH: 17
<212> TYPE: PRT
<213> ORGANISM: Artificial Sequence
<220> FEATURE:
<223> OTHER INFORMATION: Synthetic sequence

<400> SEQUENCE: 32

Trp Glu Ala Ala Ala Arg Glu Ala Cys Cys Arg Glu Cys Cys Ala Arg
1               5                   10                  15

Ala

<210> SEQ ID NO 33
<211> LENGTH: 91
<212> TYPE: PRT
<213> ORGANISM: Artificial Sequence
<220> FEATURE:
<223> OTHER INFORMATION: Synthetic sequence

<400> SEQUENCE: 33

```
Asn Val Ser Pro Pro Arg Arg Ala Arg Val Thr Asp Ala Thr Glu Thr
1               5                   10                  15

Thr Ile Thr Ile Arg Trp Glu Gly Arg Gly Val Ile Gly Phe Gln Val
            20                  25                  30

Asp Ala Val Pro Ala Asn Gly Gln Thr Pro Ile Gln Arg Thr Ile Lys
        35                  40                  45

Pro Asp Val Arg Ser Tyr Thr Ile Thr Gly Leu Gln Pro Gly Thr Asp
    50                  55                  60

Tyr Lys Ile Tyr Leu Tyr Thr Leu Pro Asn Ile Gly Thr Gly His Phe
65                  70                  75                  80

Ser Ser Ser Pro Val Val Ile Asp Ala Ser Thr
                85                  90
```

<210> SEQ ID NO 34
<211> LENGTH: 93
<212> TYPE: PRT
<213> ORGANISM: Artificial Sequence
<220> FEATURE:
<223> OTHER INFORMATION: Synthetic sequence

<400> SEQUENCE: 34

```
Asn Val Ser Pro Pro Arg Arg Ala Arg Val Thr Asp Ala Thr Glu Thr
1               5                   10                  15

Thr Ile Thr Ile Ser Trp Glu Gly Ser Pro Ser Thr Phe Ile Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Pro Asp Phe Gly Arg Gly
65                  70                  75                  80

His Phe Thr Ser Ser Pro Val Val Ile Asp Ala Ser Thr
                85                  90
```

<210> SEQ ID NO 35
<211> LENGTH: 91
<212> TYPE: PRT
<213> ORGANISM: Artificial Sequence
<220> FEATURE:
<223> OTHER INFORMATION: Synthetic sequence

<400> SEQUENCE: 35

```
Asn Val Ser Pro Pro Arg Arg Ala Arg Val Thr Asp Ala Thr Glu Thr
1               5                   10                  15

Thr Ile Thr Ile Arg Trp Glu Gly Arg Gly Val Ile Gly Phe Gln Val
            20                  25                  30

Asp Ala Val Pro Ala Asn Gly Gln Thr Pro Ile Gln Arg Thr Ile Lys
        35                  40                  45

Pro Asp Val Arg Ser Tyr Thr Ile Thr Gly Leu Gln Pro Gly Thr Asp
```

```
                 50                  55                  60

Tyr Lys Ile Tyr Leu Tyr Thr Leu Pro Asp Phe Gly Arg Gly His Phe
 65                  70                  75                  80

Thr Ser Ser Pro Val Val Ile Asp Ala Ser Thr
                 85                  90

<210> SEQ ID NO 36
<211> LENGTH: 93
<212> TYPE: PRT
<213> ORGANISM: Artificial Sequence
<220> FEATURE:
<223> OTHER INFORMATION: Synthetic sequence

<400> SEQUENCE: 36

Asn Val Ser Pro Pro Arg Arg Ala Arg Val Thr Asp Ala Thr Glu Thr
 1               5                  10                  15

Thr Ile Thr Ile Ser Trp Arg Val Ser Pro Ser Thr Val Val Gly Leu
                 20                  25                  30

Gln Val Asp Ala Val Pro Ala Asn Gly Gln Thr Pro Ile Gln Arg Thr
             35                  40                  45

Ile Lys Pro Asp Val Arg Ser Tyr Thr Ile Thr Gly Leu Gln Pro Gly
     50                  55                  60

Thr Asp Tyr Lys Ile Tyr Leu Tyr Thr Leu Asn Val Ile Gly Gly Ser
 65                  70                  75                  80

Ala His Ala Ser Ser Pro Val Val Ile Asp Ala Ser Thr
                 85                  90

<210> SEQ ID NO 37
<211> LENGTH: 373
<212> TYPE: PRT
<213> ORGANISM: Artificial Sequence
<220> FEATURE:
<223> OTHER INFORMATION: Synthetic sequence

<400> SEQUENCE: 37

Met Asp Met Arg Val Pro Ala Gln Leu Leu Gly Leu Leu Leu Leu Trp
 1               5                  10                  15

Leu Ser Gly Ala Arg Cys Asn Val Ser Pro Pro Arg Arg Ala Arg Val
                 20                  25                  30

Thr Asp Ala Thr Glu Thr Thr Ile Thr Ile Arg Trp Glu Gly Arg Gly
             35                  40                  45

Val Ile Gly Phe Gln Val Asp Ala Val Pro Ala Asn Gly Gln Thr Pro
     50                  55                  60

Ile Gln Arg Thr Ile Lys Pro Asp Val Arg Ser Tyr Thr Ile Thr Gly
 65                  70                  75                  80

Leu Gln Pro Gly Thr Asp Tyr Lys Ile Tyr Leu Tyr Thr Leu Pro Asn
                 85                  90                  95

Ile Gly Thr Gly His Phe Ser Ser Pro Val Val Ile Asp Ala Ser
                100                 105                 110

Thr Gly Gly Gly Gly Ser Glu Leu Val Val Thr Gln Glu Pro Ser Leu
            115                 120                 125

Thr Val Ser Pro Gly Gly Thr Val Thr Leu Thr Cys Arg Ser Ser Thr
    130                 135                 140

Gly Ala Val Thr Thr Ser Asn Tyr Ala Asn Trp Val Gln Gln Lys Pro
145                 150                 155                 160

Gly Gln Ala Pro Arg Gly Leu Ile Gly Gly Thr Asn Lys Arg Ala Pro
                165                 170                 175
```

```
Gly Thr Pro Ala Arg Phe Ser Gly Ser Leu Gly Gly Lys Ala Ala
            180                 185                 190

Leu Thr Leu Ser Gly Val Gln Pro Glu Asp Glu Ala Glu Tyr Tyr Cys
        195                 200                 205

Ala Leu Trp Tyr Ser Asn Leu Trp Val Phe Gly Gly Gly Thr Lys Leu
    210                 215                 220

Thr Val Leu Gly Gly Gly Ser Gly Gly Gly Ser Gly Gly Gly
225                 230                 235                 240

Gly Ser Glu Val Gln Leu Leu Glu Ser Gly Gly Leu Val Gln Pro
                245                 250                 255

Gly Gly Ser Leu Lys Leu Ser Cys Ala Ala Ser Gly Phe Thr Phe Asn
            260                 265                 270

Thr Tyr Ala Met Asn Trp Val Arg Gln Ala Pro Gly Lys Gly Leu Glu
        275                 280                 285

Trp Val Ala Arg Ile Arg Ser Lys Tyr Asn Asn Tyr Ala Thr Tyr Tyr
    290                 295                 300

Ala Asp Ser Val Lys Asp Arg Phe Thr Ile Ser Arg Asp Asp Ser Lys
305                 310                 315                 320

Asn Thr Ala Tyr Leu Gln Met Asn Asn Leu Lys Thr Glu Asp Thr Ala
                325                 330                 335

Val Tyr Tyr Cys Val Arg His Gly Asn Phe Gly Asn Ser Tyr Val Ser
            340                 345                 350

Trp Phe Ala Tyr Trp Gly Gln Gly Thr Leu Val Thr Val Ser Ser His
        355                 360                 365

His His His His His
    370

<210> SEQ ID NO 38
<211> LENGTH: 373
<212> TYPE: PRT
<213> ORGANISM: Artificial Sequence
<220> FEATURE:
<223> OTHER INFORMATION: Synthetic sequence

<400> SEQUENCE: 38

Met Asp Met Arg Val Pro Ala Gln Leu Leu Gly Leu Leu Leu Leu Trp
1               5                   10                  15

Leu Ser Gly Ala Arg Cys Asn Val Ser Pro Pro Arg Ala Arg Val
        20                  25                  30

Thr Asp Ala Thr Glu Thr Thr Ile Thr Ile Arg Trp Glu Gly Arg Gly
        35                  40                  45

Val Ile Gly Phe Gln Val Asp Ala Val Pro Ala Asn Gly Gln Thr Pro
    50                  55                  60

Ile Gln Arg Thr Ile Lys Pro Asp Val Arg Ser Tyr Thr Ile Thr Gly
65                  70                  75                  80

Leu Gln Pro Gly Thr Asp Tyr Lys Ile Tyr Leu Tyr Thr Leu Pro Asp
                85                  90                  95

Phe Gly Arg Gly His Phe Thr Ser Ser Pro Val Val Ile Asp Ala Ser
            100                 105                 110

Thr Gly Gly Gly Gly Ser Glu Leu Val Val Thr Gln Glu Pro Ser Leu
        115                 120                 125

Thr Val Ser Pro Gly Gly Thr Val Thr Leu Thr Cys Arg Ser Ser Thr
    130                 135                 140

Gly Ala Val Thr Thr Ser Asn Tyr Ala Asn Trp Val Gln Gln Lys Pro
145                 150                 155                 160
```

Gly Gln Ala Pro Arg Gly Leu Ile Gly Gly Thr Asn Lys Arg Ala Pro
            165                 170                 175

Gly Thr Pro Ala Arg Phe Ser Gly Ser Leu Leu Gly Gly Lys Ala Ala
            180                 185                 190

Leu Thr Leu Ser Gly Val Gln Pro Glu Asp Glu Ala Glu Tyr Tyr Cys
            195                 200                 205

Ala Leu Trp Tyr Ser Asn Leu Trp Val Phe Gly Gly Thr Lys Leu
            210                 215                 220

Thr Val Leu Gly Gly Gly Gly Ser Gly Gly Gly Gly Ser Gly Gly Gly
225                 230                 235                 240

Gly Ser Glu Val Gln Leu Leu Glu Ser Gly Gly Gly Leu Val Gln Pro
            245                 250                 255

Gly Gly Ser Leu Lys Leu Ser Cys Ala Ala Ser Gly Phe Thr Phe Asn
            260                 265                 270

Thr Tyr Ala Met Asn Trp Val Arg Gln Ala Pro Gly Lys Gly Leu Glu
            275                 280                 285

Trp Val Ala Arg Ile Arg Ser Lys Tyr Asn Asn Tyr Ala Thr Tyr Tyr
            290                 295                 300

Ala Asp Ser Val Lys Asp Arg Phe Thr Ile Ser Arg Asp Asp Ser Lys
305                 310                 315                 320

Asn Thr Ala Tyr Leu Gln Met Asn Asn Leu Lys Thr Glu Asp Thr Ala
            325                 330                 335

Val Tyr Tyr Cys Val Arg His Gly Asn Phe Gly Asn Ser Tyr Val Ser
            340                 345                 350

Trp Phe Ala Tyr Trp Gly Gln Gly Thr Leu Val Thr Val Ser Ser His
            355                 360                 365

His His His His His
    370

<210> SEQ ID NO 39
<211> LENGTH: 375
<212> TYPE: PRT
<213> ORGANISM: Artificial Sequence
<220> FEATURE:
<223> OTHER INFORMATION: Synthetic sequence

<400> SEQUENCE: 39

Met Asp Met Arg Val Pro Ala Gln Leu Leu Gly Leu Leu Leu Leu Trp
1               5                   10                  15

Leu Ser Gly Ala Arg Cys Asn Val Ser Pro Pro Arg Arg Ala Arg Val
            20                  25                  30

Thr Asp Ala Thr Glu Thr Thr Ile Thr Ile Ser Trp Arg Val Ser Pro
            35                  40                  45

Ser Thr Val Val Gly Leu Gln Val Asp Ala Val Pro Ala Asn Gly Gln
            50                  55                  60

Thr Pro Ile Gln Arg Thr Ile Lys Pro Asp Val Arg Ser Tyr Thr Ile
65                  70                  75                  80

Thr Gly Leu Gln Pro Gly Thr Asp Tyr Lys Ile Tyr Leu Tyr Thr Leu
            85                  90                  95

Asn Val Ile Gly Gly Ser Ala His Ala Ser Ser Pro Val Val Ile Asp
            100                 105                 110

Ala Ser Thr Gly Gly Gly Gly Ser Glu Leu Val Val Thr Gln Glu Pro
            115                 120                 125

Ser Leu Thr Val Ser Pro Gly Gly Thr Val Thr Leu Thr Cys Arg Ser
            130                 135                 140

Ser Thr Gly Ala Val Thr Thr Ser Asn Tyr Ala Asn Trp Val Gln Gln
145                 150                 155                 160

Lys Pro Gly Gln Ala Pro Arg Gly Leu Ile Gly Gly Thr Asn Lys Arg
            165                 170                 175

Ala Pro Gly Thr Pro Ala Arg Phe Ser Gly Ser Leu Leu Gly Gly Lys
            180                 185                 190

Ala Ala Leu Thr Leu Ser Gly Val Gln Pro Glu Asp Glu Ala Glu Tyr
        195                 200                 205

Tyr Cys Ala Leu Trp Tyr Ser Asn Leu Trp Val Phe Gly Gly Gly Thr
    210                 215                 220

Lys Leu Thr Val Leu Gly Gly Gly Gly Ser Gly Gly Gly Gly Ser Gly
225                 230                 235                 240

Gly Gly Gly Ser Glu Val Gln Leu Leu Glu Ser Gly Gly Gly Leu Val
            245                 250                 255

Gln Pro Gly Gly Ser Leu Lys Leu Ser Cys Ala Ala Ser Gly Phe Thr
            260                 265                 270

Phe Asn Thr Tyr Ala Met Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Gly Asn Phe Gly Asn Ser Tyr
            340                 345                 350

Val Ser Trp Phe Ala Tyr Trp Gly Gln Gly Thr Leu Val Thr Val Ser
        355                 360                 365

Ser His His His His His His
    370                 375

<210> SEQ ID NO 40
<211> LENGTH: 479
<212> TYPE: PRT
<213> ORGANISM: Artificial Sequence
<220> FEATURE:
<223> OTHER INFORMATION: Synthetic sequence

<400> SEQUENCE: 40

Met Asp Met Arg Val Pro Ala Gln Leu Leu Gly Leu Leu Leu Leu Trp
1               5                   10                  15

Leu Ser Gly Ala Arg Cys Asn Val Ser Pro Pro Arg Ala Arg Val
            20                  25                  30

Thr Asp Ala Thr Glu Thr Thr Ile Thr Ile Arg Trp Glu Gly Arg Gly
        35                  40                  45

Val Ile Gly Phe Gln Val Asp Ala Val Pro Ala Asn Gly Gln Thr Pro
    50                  55                  60

Ile Gln Arg Thr Ile Lys Pro Asp Val Arg Ser Tyr Thr Ile Thr Gly
65                  70                  75                  80

Leu Gln Pro Gly Thr Asp Tyr Lys Ile Tyr Leu Tyr Thr Leu Pro Asn
            85                  90                  95

Ile Gly Thr Gly His Phe Ser Ser Pro Val Val Ile Asp Ala Ser
        100                 105                 110

Thr Gly Gly Gly Gly Ser Gly Gly Gly Ser Gly Gly Gly Ser
        115                 120                 125

```
                    -continued

Asn Val Ser Pro Pro Arg Arg Ala Arg Val Thr Asp Ala Thr Glu Thr
    130                 135                 140

Thr Ile Thr Ile Arg Trp Glu Gly Arg Gly Val Ile Gly Phe Gln Val
145                 150                 155                 160

Asp Ala Val Pro Ala Asn Gly Gln Thr Pro Ile Gln Arg Thr Ile Lys
                165                 170                 175

Pro Asp Val Arg Ser Tyr Thr Ile Thr Gly Leu Gln Pro Gly Thr Asp
            180                 185                 190

Tyr Lys Ile Tyr Leu Tyr Thr Leu Pro Asp Phe Gly Arg Gly His Phe
        195                 200                 205

Thr Ser Ser Pro Val Val Ile Asp Ala Ser Thr Gly Gly Gly Ser
210                 215                 220

Glu Leu Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
            260                 265                 270

Leu Ile Gly Gly Thr Asn Lys Arg Ala Pro Gly Thr Pro Ala Arg Phe
        275                 280                 285

Ser Gly Ser Leu Leu Gly Gly Lys Ala Ala Leu Thr Leu Ser Gly Val
    290                 295                 300

Gln Pro Glu Asp Glu Ala Glu Tyr Tyr Cys Ala Leu Trp Tyr Ser Asn
305                 310                 315                 320

Leu Trp Val Phe Gly Gly Gly Thr Lys Leu Thr Val Leu Gly Gly Gly
                325                 330                 335

Gly Ser Gly Gly Gly Gly Ser Gly Gly Gly Ser Glu Val Gln Leu
            340                 345                 350

Leu Glu Ser Gly Gly Gly Leu Val Gln Pro Gly Gly Ser Leu Lys Leu
        355                 360                 365

Ser Cys Ala Ala Ser Gly Phe Thr Phe Asn Thr Tyr Ala Met Asn Trp
    370                 375                 380

Val Arg Gln Ala Pro Gly Lys Gly Leu Glu Trp Val Ala Arg Ile Arg
385                 390                 395                 400

Ser Lys Tyr Asn Asn Tyr Ala Thr Tyr Ala Asp Ser Val Lys Asp
                405                 410                 415

Arg Phe Thr Ile Ser Arg Asp Asp Ser Lys Asn Thr Ala Tyr Leu Gln
            420                 425                 430

Met Asn Asn Leu Lys Thr Glu Asp Thr Ala Val Tyr Tyr Cys Val Arg
        435                 440                 445

His Gly Asn Phe Gly Asn Ser Tyr Val Ser Trp Phe Ala Tyr Trp Gly
    450                 455                 460

Gln Gly Thr Leu Val Thr Val Ser Ser His His His His His
465                 470                 475

<210> SEQ ID NO 41
<211> LENGTH: 586
<212> TYPE: PRT
<213> ORGANISM: Artificial Sequence
<220> FEATURE:
<223> OTHER INFORMATION: Synthetic sequence

<400> SEQUENCE: 41

Met Asp Met Arg Val Pro Ala Gln Leu Leu Gly Leu Leu Leu Leu Trp
1               5                   10                  15
```

-continued

```
Leu Ser Gly Ala Arg Cys Asn Val Ser Pro Pro Arg Ala Arg Val
                 20                  25                  30

Thr Asp Ala Thr Glu Thr Thr Ile Thr Ile Arg Trp Glu Gly Arg Gly
             35                  40                  45

Val Ile Gly Phe Gln Val Asp Ala Val Pro Ala Asn Gly Gln Thr Pro
         50                  55                  60

Ile Gln Arg Thr Ile Lys Pro Asp Val Arg Ser Tyr Thr Ile Thr Gly
 65                  70                  75                  80

Leu Gln Pro Gly Thr Asp Tyr Lys Ile Tyr Leu Tyr Thr Leu Pro Asn
                 85                  90                  95

Ile Gly Thr Gly His Phe Ser Ser Pro Val Val Ile Asp Ala Ser
             100                 105                 110

Thr Gly Gly Gly Gly Ser Gly Gly Gly Gly Ser Gly Gly Gly Gly Ser
         115                 120                 125

Asn Val Ser Pro Pro Arg Arg Ala Arg Val Thr Asp Ala Thr Glu Thr
     130                 135                 140

Thr Ile Thr Ile Arg Trp Glu Gly Arg Gly Val Ile Gly Phe Gln Val
145                 150                 155                 160

Asp Ala Val Pro Ala Asn Gly Gln Thr Pro Ile Gln Arg Thr Ile Lys
                 165                 170                 175

Pro Asp Val Arg Ser Tyr Thr Ile Thr Gly Leu Gln Pro Gly Thr Asp
             180                 185                 190

Tyr Lys Ile Tyr Leu Tyr Thr Leu Pro Asp Phe Gly Arg Gly His Phe
         195                 200                 205

Thr Ser Ser Pro Val Val Ile Asp Ala Ser Thr Gly Gly Gly Gly Ser
     210                 215                 220

Gly Gly Gly Gly Ser Gly Gly Gly Gly Asn Val Ser Pro Pro Arg Arg
225                 230                 235                 240

Ala Arg Val Thr Asp Ala Thr Glu Thr Thr Ile Thr Ile Ser Trp Arg
                 245                 250                 255

Val Ser Pro Ser Thr Val Val Gly Leu Gln Val Asp Ala Val Pro Ala
             260                 265                 270

Asn Gly Gln Thr Pro Ile Gln Arg Thr Ile Lys Pro Asp Val Arg Ser
         275                 280                 285

Tyr Thr Ile Thr Gly Leu Gln Pro Gly Thr Asp Tyr Lys Ile Tyr Leu
     290                 295                 300

Tyr Thr Leu Asn Val Ile Gly Gly Ser Ala His Ala Ser Ser Pro Val
305                 310                 315                 320

Val Ile Asp Ala Ser Thr Gly Gly Gly Gly Ser Glu Leu Val Val Thr
                 325                 330                 335

Gln Glu Pro Ser Leu Thr Val Ser Pro Gly Gly Thr Val Thr Leu Thr
             340                 345                 350

Cys Arg Ser Ser Thr Gly Ala Val Thr Thr Ser Asn Tyr Ala Asn Trp
         355                 360                 365

Val Gln Gln Lys Pro Gly Gln Ala Pro Arg Gly Leu Ile Gly Gly Thr
     370                 375                 380

Asn Lys Arg Ala Pro Gly Thr Pro Ala Arg Phe Ser Gly Ser Leu Leu
385                 390                 395                 400

Gly Gly Lys Ala Ala Leu Thr Leu Ser Gly Val Gln Pro Glu Asp Glu
                 405                 410                 415
```

```
Ala Glu Tyr Tyr Cys Ala Leu Trp Tyr Ser Asn Leu Trp Val Phe Gly
            420                 425                 430

Gly Gly Thr Lys Leu Thr Val Leu Gly Gly Gly Ser Gly Gly Gly
        435             440             445

Gly Ser Gly Gly Gly Ser Glu Val Gln Leu Leu Glu Ser Gly Gly
    450             455             460

Gly Leu Val Gln Pro Gly Gly Ser Leu Lys Leu Ser Cys Ala Ala Ser
465             470             475             480

Gly Phe Thr Phe Asn Thr Tyr Ala Met Asn Trp Val Arg Gln Ala Pro
                485             490             495

Gly Lys Gly Leu Glu Trp Val Ala Arg Ile Arg Ser Lys Tyr Asn Asn
            500             505             510

Tyr Ala Thr Tyr Tyr Ala Asp Ser Val Lys Asp Arg Phe Thr Ile Ser
        515             520             525

Arg Asp Asp Ser Lys Asn Thr Ala Tyr Leu Gln Met Asn Asn Leu Lys
530             535             540

Thr Glu Asp Thr Ala Val Tyr Tyr Cys Val Arg His Gly Asn Phe Gly
545             550             555             560

Asn Ser Tyr Val Ser Trp Phe Ala Tyr Trp Gly Gln Gly Thr Leu Val
            565             570             575

Thr Val Ser Ser His His His His His His
            580             585

<210> SEQ ID NO 42
<211> LENGTH: 84
<212> TYPE: PRT
<213> ORGANISM: Artificial Sequence
<220> FEATURE:
<223> OTHER INFORMATION: Synthetic sequence

<400> SEQUENCE: 42

Asn Val Ser Pro Pro Arg Arg Ala Arg Val Thr Asp Ala Thr Glu Thr
1               5                   10                  15

Thr Ile Thr Ile Pro Trp Ala Leu Ala Gly Ser Pro Val Val Arg Phe
            20                  25                  30

Gln Val Asp Ala Val Pro Ala Asn Gly Gln Thr Pro Ile Gln Arg Thr
        35                  40                  45

Ile Gln Pro Ser Lys Arg Gly Tyr Thr Ile Thr Gly Leu Gln Pro Gly
    50                  55                  60

Thr Asp Tyr Lys Ile Tyr Leu Tyr Thr Leu Asn Gly Pro Val Val Ile
65                  70                  75                  80

Asp Ala Ser Thr
```